United States Patent
Lu et al.

(10) Patent No.: US 10,793,609 B2
(45) Date of Patent: Oct. 6, 2020

(54) COMPRESSED PATHWAYS FOR NONRIBOSOMAL MOLECULAR BIOSYNTHESIS

(71) Applicant: Massachusetts Institute of Technology, Cambridge, MA (US)

(72) Inventors: Timothy Kuan-Ta Lu, Cambridge, MA (US); Sara da Luz Areosa Cleto, Quincy, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 134 days.

(21) Appl. No.: 15/579,631

(22) PCT Filed: Jun. 3, 2016

(86) PCT No.: PCT/US2016/035728
§ 371 (c)(1),
(2) Date: Dec. 5, 2017

(87) PCT Pub. No.: WO2016/196940
PCT Pub. Date: Dec. 8, 2016

(65) Prior Publication Data
US 2018/0155400 A1    Jun. 7, 2018

Related U.S. Application Data

(60) Provisional application No. 62/171,651, filed on Jun. 5, 2015.

(51) Int. Cl.
| | | |
|---|---|---|
| *C07K 14/245* | (2006.01) | |
| *C12N 15/52* | (2006.01) | |
| *C12P 21/00* | (2006.01) | |
| *C40B 40/06* | (2006.01) | |
| *C12N 9/52* | (2006.01) | |

(52) U.S. Cl.
CPC ............ *C07K 14/245* (2013.01); *C12N 9/52* (2013.01); *C12N 15/52* (2013.01); *C12P 21/00* (2013.01); *C40B 40/06* (2013.01)

(58) Field of Classification Search
None
See application file for complete search history.

(56) References Cited

U.S. PATENT DOCUMENTS

| | | |
|---|---|---|
| 5,554,507 A | 9/1996 | Grossman et al. |
| 7,291,490 B2 | 11/2007 | Farnet et al. |
| 2010/0048422 A1 | 2/2010 | Walsh et al. |
| 2014/0243286 A1 | 8/2014 | Arnold et al. |

FOREIGN PATENT DOCUMENTS

| | | |
|---|---|---|
| WO | WO 2008/073148 A2 | 6/2008 |
| WO | WO 2011/073956 A2 | 6/2011 |

OTHER PUBLICATIONS

Kizer L et al. Application of Functional Genomics to Pathway Optimization for Increased Isoprenoid Production. 2008. Applied and Envifonrmental Microbiology. vol. 74, No. 10. p. 3229-3241.*
Prather KLJ et al. De novo biosynthetic pathways: rational design of microbial chemical factories. 2008. Current Opinion in Biotechnology. 19:468-474.*
Velkov et al., Non-ribosomal peptide synthetases as technological platforms for the synthesis of highly modified peptide bioeffectors—Cyclosporin synthetase as a complex example. Biotechnol Annu Rev. 2003;9:151-97.
Fischbach et al., Assembly-line enzymology for polyketide and nonribosomal Peptide antibiotics: logic, machinery, and mechanisms. Chem Rev. Aug. 2006;106(8):3468-96.
Gehring et al., Enterobactin biosynthesis in *Escherichia coli*: isochorismate lyase (EntB) is a bifunctional enzyme that is phosphopantetheinylated by EntD and then acylated by EntE using ATP and 2,3-dihydroxybenzoate. Biochemistry. Jul. 15, 1997;36(28):8495-503.
Gobin et al., Characterization of exochelins of the *Mycobacterium bovis* type strain and BCG substrains. Infect Immun. Apr. 1999;67(4):2035-9.
Hopwood et al., Production of 'hybrid' antibiotics by genetic engineering. Nature. Apr. 18-24, 1985;314(6012):642-4.
Katsuyama et al., Synthesis of unnatural flavonoids and stilbenes by exploiting the plant biosynthetic pathway in *Escherichia coli*. Chem Biol. Jun. 2007;14(6):613-21.
Keating et al., Reconstitution and characterization of the Vibrio cholerae vibriobactin synthetase from VibB, VibE, VibF, and VibH. Biochemistry. Dec. 19, 2000;39(50):15522-30.
Keating et al., Vibriobactin biosynthesis in Vibrio cholerae: VibH is an amide synthase homologous to nonribosomal peptide synthetase condensation domains. Biochemistry. Dec. 19, 2000;39(50):15513-21.
Snow, Mycobactins: iron-chelating growth factors from mycobacteria. Bacteriol Rev. Jun. 1970;34(2):99-125.

(Continued)

*Primary Examiner* — Paul J Holland
(74) *Attorney, Agent, or Firm* — Wolf, Greenfield & Sacks, P.C.

(57) ABSTRACT

Provided herein are synthetic pathways from *Escherichia coli* and *Vibrio cholerae* genes for the production of new, synthetic nonribosomal peptides, and methods and compositions comprising the same. Some aspects of the present disclosure are directed to modified bacterial cells comprising a compressed biosynthetic pathway that comprises (a) biosynthetic genes obtained from one species encoding enzymes active in the bioassembly of a nonribosomal molecule, (b) biosynthetic genes obtained from another species encoding enzymes active in the bioassembly of a nonribosomal molecule that is different from the nonribosomal molecule of (a). In some embodiments, the biosynthetic genes of (a) are *Escherichia coli* biosynthetic genes and may include entD gene, an entC gene, an entE gene, an entB gene and an entA gene. In some embodiments, the biosynthetic genes of (b) are *Vibrio cholera* biosynthetic genes and may include a vibH gene and a vibF gene.

12 Claims, 21 Drawing Sheets

Specification includes a Sequence Listing.

(56) References Cited

OTHER PUBLICATIONS

Strieker et al., Nonribosomal peptide synthetases: structures and dynamics. Curr Opin Struct Biol. Apr. 2010;20(2):234-40. doi: 10.1016/j.sbi.2010.01.009. Epub Feb. 10, 2010.

Voss et al., Iron acquisition and metabolism by mycobacteria. J Bacteriol. Aug. 1999;181(15):4443-51.

Weissman, The structural biology of biosynthetic megaenzymes. Nat Chem Biol. Sep. 2015;11(9):660-70. doi: 10.1038/nchembio. 1883.

Wyckoff et al., Cloning of a Vibrio cholerae vibriobactin gene cluster: identification of genes required for early steps in siderophore biosynthesis. J Bacteriol. Nov. 1997;179(22):7055-62.

Wyckoff et al., VibD and VibH are required for late steps in vibriobactin biosynthesis in Vibrio cholerae. J Bacteriol. Mar. 2001;183(5):1830-4.

\* cited by examiner

Enterobactin

[M+H]$^+$
670.1515 calc
670.1509 obs

Linear enterobactin

[M+H]$^+$
688.1621 calc
688.1613 obs

Enterobactin dimer

[M+H]+
465.1140 calc
465.1133 obs

Enterobactin monomer

[M+H]+
242.0659 calc
242.0653 obs

Linear thr-enterobactin

[M+H]⁺
730.2090 calc
730.2097 obs

Thr-enterobactin dimer

[M+H]⁺
493.1453 calc
493.1448 obs m/z
137.0239 calc
137.0231 obs

Thr-enterobactin monomer

[M+H]⁺
256.0816 calc
256.0811 obs

M1

[M+H]⁺
211.1077 calc
211.1073 obs

M1Tc

[M+H]⁺
430.1609 calc
430.1601 obs

M2

[M+H]⁺
282.1812 calc
282.1810 obs

M2Tc

[M+H]⁺
501.2344 calc
501.2342 obs

M2So

[M+H]⁺
505.2293 calc
505.2316 obs

M2To

[M+H]⁺
519.2449 calc
519.2439 obs

M3Tc

[M+H]⁺
544.2768 calc
544.2758 obs

M3Sc

[M+H]⁺
530.2609 calc
530.2601 obs

M3So

[M+H]⁺
548.2715 calc
548.2712 obs

M4

[M+H]⁺
239.1390 calc
239.1389 obs

M5Tc

[M+H]⁺
444.1765 calc
444.1764 obs

M5To

[M+H]⁺
462.1871 calc
462.1861 obs

M6

[M+H]⁺

268.1656 calc

268.1654 obs

M6Tc

[M+H]⁺

487.2187 calc

487.2187 obs

M6To

[M+H]⁺

505.2293 calc

505.2290 obs

M7

[M+H]+
273.1234 calc
273.1228 obs

M9

[M+H]+
287.1390 calc
287.1389 obs

M9Tc

[M+H]+
506.1922 calc
506.1923 obs

M9Sc

[M+H]⁺
492.1765 calc
492.1754 obs

M9To

[M+H]⁺
524.2027 calc
524.2033 obs

M10

[M+H]⁺
259.1077 calc
259.1076 obs

M12

[M+H]+
337.1183 calc
337.1180 obs

M21

[M+H]+
281.1860 calc
281.1857 obs

SEQUENCE LISTING

<160> NUMBER OF SEQ ID NOS: 11

<210> SEQ ID NO 1
<211> LENGTH: 747
<212> TYPE: DNA
<213> ORGANISM: Escherichia coli

<400> SEQUENCE: 1

```
atggatttca gcggtaaaaa tgtctgggta accggcgcag gtaaaggtat cggctacgcc      60
acggcgctgg cgtttgttga ggcgggagcg aaagttacag gttttgatca agcgttcact     120
caggagcaat atccctttgc gaccgaagtg atggatgttg ccgacgctgc gcaggtcgcg     180
caagtgtgtc agcgactgtt agctgaaacg gagcgactgg acgcgctggt caatgcggcg     240
ggaattttac gcatgggcgc gaccgatcag ctcagtaaag aggactggca gcagactttt     300
gcggttaacg tcggcggtgc gtttaacctg ttccagcaaa ccatgaacca gtttcgccgt     360
cagcggggcg gggcgattgt cactgtggcg tccgacgccg cgcacacgcc gcgtattggc     420
atgagtgctt atggcgcatc gaaagcggcg ctgaaaagcc tggcgttgag cgtcgggctg     480
gaactggcgg gtagcggcgt gcgctgtaat gtggtttcgc ctggctccac cgacaccgat     540
atgcaacgca cgctgtgggt gagcgatgac gccgaagaac agcgtattcg cggctttggc     600
gagcagttta aactcggcat tccgctgggg aaaatcgccc gtccacaaga gatcgccaac     660
acgattttgt tcctcgcctc tgacctcgcc agccatatta ccctacagga tattgtggtc     720
gatggcggct caacgctggg ggcataa                                          747
```

<210> SEQ ID NO 2
<211> LENGTH: 858
<212> TYPE: DNA
<213> ORGANISM: Escherichia coli

<400> SEQUENCE: 2

```
atggctattc caaaattaca ggcttacgca ctgccggagt ctcacgatat tccgcagaat      60
aaagttgact gggcctttga accgcaacgt gccgcgttgt taatccatga tatgcaggac     120
tattttgtca gcttctgggg cgagaactgc ccgatgatga agcaggtgat cgcgaatatt     180
gctgcgctgc gcgactactg caaacagcac aatatcccgg tttattacac cgcccagccg     240
aaagagcaga gcgatgaaga tcgggcgctg ttgaatgata tgtgggggcc gggcctgacc     300
cgctcgccgg aacagcaaaa ggtggtggat cgcctgacgc cagatgccga cgacacggtg     360
ctggtgaagt ggcgctacag cgcgtttcat cgttctccgc tggagcaaat gctgaaagag     420
agtggacgta accagctgat tattaccggg gtatatgccc acattggctg tatgaccacc     480
gcaaccgacg catttatgcg cgatattaaa ccgtttatgt ggcggatgc gctggccgat     540
ttcagccgtg acgagcattt gatgtcgctg aaatatgtgg ccggacgttc tggccgggtg     600
gtgatgactg aagaattact gccagcacct atccccgcca gcaaagcggc gctgcgtgag     660
gtgatcctgc cgttgctgga cgagtccgat gaaccgttcg atgacgacaa cctgatcgac     720
tacggtctgg attcggtgcg catgatggcg ctggcggcgc gctggcgcaa agtgcatggt     780
gatatcgact ttgtcatgct ggcgaaaaac ccgaccatcg acgcctggtg gaagctactc     840
```

```
tcccgcgagg tgaaataa                                                 858
```

<210> SEQ ID NO 3
<211> LENGTH: 1176
<212> TYPE: DNA
<213> ORGANISM: Escherichia coli

<400> SEQUENCE: 3

```
atggatacgt cactggctga ggaagtacag cagaccatgg caacacttgc gcccaatcgc    60
tttttcttta tgtcgccgta ccgcagtttt acgacgtcag gatgtttcgc ccgcttcgat   120
gaaccggctg tgaacgggga ttcgcccgac agtcccttcc agcaaaaact cgccgcgctg   180
tttgccgatg ccaaagcgca gggcatcaaa atccggtga tggtcggggc gattcccttc    240
gatccacgtc agccttcgtc gctgtatatt cctgaatcct ggcagtcgtt ctcccgtcag   300
gaaaaacaag cttccgcacg ccgtttcacc cgcagccagt cgctgaatgt ggtggaacgc   360
caggcaattc cggagcaaac cacgtttgaa cagatggttg cccgcgccgc cgcacttacc   420
gccacgccgc aggtcgacaa agtggtgttg tcacggttga ttgatatcac cactgacgcc   480
gccattgata gtggcgtatt gctggaacgg ttgattgcgc aaaacccggt tagttacaac   540
ttccatgttc cgctggctga tggtggcgtc ctgctggggg ccagcccgga actgctgcta   600
cgtaaagacg cgagcgttt tagctccatt ccgttagccg gttccgcgcg tcgtcagccg   660
gatgaagtgc tcgatcgcga agcaggtaat cgtctgctgg cgtcagaaaa agatcgccat   720
gaacatgaac tggtgactca ggcgatgaaa gaggtactgc gcgaacgcag tagtgagtta   780
cacgttcctt cttctccaca gctgatcacc acgccgacgc tgtggcatct cgcaactccc   840
tttgaaggta aagcgaattc gcaagaaaac gcactgactc tggcctgtct gctgcatccg   900
accccgcgc tgagcggttt cccgcatcag gccgcgaccc aggttattgc tgaactggaa   960
ccgttcgacc gcgaactgtt tggcggcatt gtgggttggt gtgacagcga aggtaacggc  1020
gaatgggtgg tgaccatccg ctgcgcgaag ctgcgggaaa tcaggtgcg tctgtttgcc   1080
ggagcgggga ttgtgcctgc gtcgtcaccg ttgggtgagt ggcgcgaaac aggcgtcaaa  1140
ctttctacca tgttgaacgt ttttggattg cattaa                            1176
```

<210> SEQ ID NO 4
<211> LENGTH: 621
<212> TYPE: DNA
<213> ORGANISM: Escherichia coli

<400> SEQUENCE: 4

```
atgaaaacta cgcatacctc cctcccctttt gccggacata cgctgcattt tgttgagttc    60
gatccggcga ttttttgtga gcaggattta ctctggctgc cgcactacgc acaactgcaa   120
cacgctggac gtaaacgtaa aacagagcat ttagccggac ggatcgctgc tgtttatgct   180
ttgcgggaat atggctataa atgtgtgccc gcaatcggcg agctacgcca acctgtctgg   240
cctgcggagg tatacggcag tattagccac tgtgggacta cggcattagc cgtggtatct   300
cgtcaaccga ttggcattga tatagaagaa attttttctg tacaaaccgc aagagaattg   360
acagacaaca ttattacacc agcggaacac gagcgactcg cagactgcgg tttagccttt   420
tctctggcgc tgacactggc attttccgcc aaagagagcg catttaaggc aagtgagatc   480
caaactgatg caggtttcct ggactatcag ataattagct ggaataaaca gcaggtcatc   540
attcatcgtg agaatgagat gtttgctgtg cactggcaga taaaagaaaa gatagtcata   600
```

```
acgctgtgcc aacacgatta a                                      621
```

<210> SEQ ID NO 5
<211> LENGTH: 1611
<212> TYPE: DNA
<213> ORGANISM: Escherichia coli

<400> SEQUENCE: 5

```
atgagcattc cattcacccg ctggccggaa gagtttgccc gtcgctatcg ggaaaaaggc    60
tactggcagg atttgccgct gaccgacatt ctgacgcgac atgctgcgag tgacagcatc   120
gcggttatcg acggcgagcg acagttgagt tatcgggagc tgaatcaggc ggcggataac   180
ctcgcgtgta gtttacgccg tcagggcatt aaacctggtg aaaccgcgct ggtacaactg   240
ggtaacgtcg ctgaattgta tattaccttt ttcgcgctgc tgaaactggg cgttgcgccg   300
gtgctggcgt tgttcagcca tcagcgtagt gaactgaacg cctatgccag ccagattgaa   360
cccgcattgc tgattgccga tgccaacat gcgctgttta gcggggatga tttcctcaat   420
actttcgtca cagaacattc ctccattcgc gtggtgcaac tgctcaacga cagcggtgag   480
cataacttgc aggatgcgat taaccatccg gctgaggatt ttactgccac gccatcacct   540
gctgatgaag tggcctattt ccagcttttcc ggtggcacca ccggcacacc gaaactgatc   600
ccgcgcactc ataacgacta ctactacagc gtgcgtcgta gcgtcgagat ttgtcagttc   660
acacaacaga cacgctacct gtgcgcgatc ccggcggctc ataactacgc catgagttcg   720
ccaggatcgc tgggcgtctt tcttgccgga ggaacggttg ttctggcggc cgatcccagc   780
gccacgctct gtttcccatt gattgaaaaa catcaggtta acgttaccgc gctggtgcca   840
cccgcagtca gcctgtggtt gcaggcgctg atcgaaggcg aaagccgggc gcagcttgcc   900
tcgctgaaac tgttacaggt cggcggcgca cgtctttctg ccaccccttgc ggcgcgtatt   960
cccgctgaga ttggctgtca gttgcagcag gtgtttggca tggcggaagg ctggtgaac   1020
tacacccgac ttgatgatag cgcggagaaa attatccata cccagggta cccaatgtgt   1080
ccggatgacg aagtatgggt tgccgatgcc gaaggaaatc cactgccgca aggggaagtc   1140
ggacgcctga tgacgcgcgg gccgtacacc ttccgcggct attacaaaag tccacagcac   1200
aatgccagcg cctttgatgc caacggtttt tactgttccg gcgatctgat ctctattgat   1260
ccagagggtt acatcaccgt gcaggggcgc gagaaagatc agattaaccg tggcggcgag   1320
aagatcgctg ccgaagagat cgaaaacctg ctgctgcgcc acccggcggt gatctacgcc   1380
gcactggtga gcatggaaga tgagctgatg ggcgaaaaaa gctgcgctta tctggtggta   1440
aaagagccgc tgcgcgcggt gcaggtgcgt cgtttcctgc gtgaacaggg tattgccgaa   1500
tttaaattac cggatcgcgt ggagtgtgtg gattcacttc cgctgacggc ggtcgggaaa   1560
gtcgataaaa acaattacg tcagtggctg gcgtcacgcg catcagcctg a              1611
```

<210> SEQ ID NO 6
<211> LENGTH: 7241
<212> TYPE: DNA
<213> ORGANISM: Vibrio cholera

<400> SEQUENCE: 6

```
atgaaagaaa tgacagcaat gcaagcggct tattggctag ggcgtcaaca cgactgcttg    60
ctcgatggtg tggccgcgca tctctacgcc gaatttgatg gtcaagcatt aaatcgacag   120
gcgctaacgg aagcggtacg tgcgctgtac gcgaaacatc ccatgttacg tttagcgatc   180
accaaggatg gacagcagaa gatcttgccg ctctcaactt tccatcagct taaagtggat   240
```

```
gacctatcac aatggaagcc agatgaggtg gagtcttttg tgcatactaa gcgccagcga      300
atgacccacc agatgctcga tttaactcag ggaaacccga ttgagatcag cttgactctg      360
ttgcctgagg gcaaacaccg attacacatt gatgcggata tgattgcgtg tgatgcacaa      420
agttttcggc tgttggtgga cgatctcacc tcactctatt tagaggccat agagcatcga      480
ttagagatca ttgagtctga tgtggtgact ttttttccaat atcttgatgc tcagcaagcc      540
gatcgtgctt tggcaaaacg caaagaggtg gataagaaat ggtggcaaga gcgtcttgcg      600
acgattcccg ccgagccaag tttgccttat caacccgtac caaccgacgc cgttagcgca      660
aacagccaaa ggtttgcaca ctggttcact ccagtggagc gcaaagggtt ggcggaggtt      720
gcgcggcaac atcatctcac actgacccaa ctgacattgg cactcttttc acaagtgatt      780
gccaatgctt gccaagagag acaatttcga ctcaatgtac ctacattcca tcgcggcaat      840
cgctctttgg atattgaaca cacgatcggc gattttcca atttgctgat ttttagcgcc        900
gatgtgggaa cgactcagac cctgttaagc ctgtgtcagc aaacggctaa ccaactgcat      960
caattacttc gccatgaaag ctattcaggg gttagcgtga tgcgcgattt atcgcggaaa     1020
cagggtgggg tgcagcgttc accgatagtc tttacctcag gcatggaaat gcgagacgag     1080
gagatctttt ccgatcatgt cactcagcat ttagggcgta tgaattgggt gatttcgcag     1140
ggagcgcagg tgactctcga tgcgcaaatt gctccggctt atgaagggat tttgctcaat     1200
tgggatgtgc gaatggaaaa cttcgctgat aaggacatca cagcgctttt cgcgcattac     1260
gttgatttga tccgctgtgt ggcgctgcat cctgagatga tgcagcaaag cgtacaacag     1320
attgacgcgc aactcggtta tgctcgccgc gagtcgattc aggagatgcc actgacccct     1380
ttacaacaag cttacttgct aggtcgctca acccaaattg ccttaggcgg cgtcgcgatg     1440
catgagtttc gtgagtatcg aggtcacatc gacactcagt cactgcatag ccgtctgctc     1500
tatctcgttg agcatattcc tgccttgaga actcgcattg atcaagagaa atggattcag     1560
tgggtctctc cttgcatagc gttaaattgg caagccatcg atttacagca tctttcccgc     1620
gaacaagcct tattagcggt tgagccagtc aggcagcaat atcagcagcg gatgcatgat     1680
ttaacgcgct cgccctggca aatctgtgtg gtgcaactgc aatagaaga gcaagaggag      1740 ttcagctcca tcgtattgac cagctttgat gctttgattg tcgatggtcg cacccatgca     1800
ctcattcttg ctgcactact aggaagcgaa gaacccgata taactcaggt ggtgcaaaat     1860
gctcgtgata ctcagtccat ctcgccgcaa ttcgcctcca aaaagcgca agatgaagcg      1920 tattggaaaa gcaaacttca tcctgattgc ccgccgccag cactgccttg gaacaagca      1980 ttagagacga tcactacgtc tcgttatgct cgtgaaagtt tgcaaatacc caagagagt      2040 gtcggtaagc tcaatcgatg cggcattgaa aatggcttat ttctcaattc cttgctgaca     2100
gcaaccatct ggacgtgctc tcctattgg acaaccgaaa tcgggatgcg agtgggtttt       2160
ccggtattaa ttccaagcag taatgcgatt gatggcaatg agtcatcctt tgtgatctta     2220
gagcatgaaa atccaccct gagtttgctg agccaagcga gcaagctaca gcgtgagatg      2280
ctagaggctc ttgagcatct tgctttttct ggcgtcgatc ttaaccgtct gttgatgaat     2340
caagcgccgc aagctctggt gctgccggtt gtgttaacca atggtttgtc ttggaaaacc     2400
ctgaatccag aggacgctgt cactctgttc gatggggtaa cgcaaactcc gcagtggctt     2460
tagatattcg cttaacttac gacgagcaga aaaacctcat catcagcttt gattatgctt     2520
tagcggtttt agagactgag cttatccgcg agatgttaag tgccttacat catcgcttga     2580
```

```
gtcagatcac ttcgtcagca tcattggccg cgccgcttga gccatgtatc gacctttcac    2640
actaccgttt taatagcgat gagtcggcca gtcacgattg cgattttctt gccaagttag    2700
cgcagcaatt gtttgtccgc acagaggata aaccgctgt gatctgcggt gaacaaaccc     2760
tttcttatgc tcaattgggt gagcaggttc agcgcgtgag gtggcagctc aaagcgcgag    2820
ggttgaccac aggaaatgtg ctcgccattt gcttgccacg cagtgttgaa catatcgtca    2880
tcagtttggc ttctgcactt tcggggatta tctgggtacc tattgatgct gcgtctccca    2940
aagagcgtct gaattacctt ttagaaaatt gtcacgccga tctggtggtg atggataagc    3000
cctgtgagtt tggcaatgtg atcgcttttg atgccttgat tgagcctgtc ttattcgccg    3060
atggagtacc tgacgttaca ccactcgatc aattaagccg attaagccaa agccaacaaa    3120
cggcttatta tctttatacc tctggcacta cgggcaaacc taagtgcgtg gtggtcaata    3180
atcaggcgac ctcgaatgtg attggtcaaa ctggccaagc gtggcatctc accagtgagg    3240
atgtggtgat gtcagtgacg ccattgcatc atgatatgtc ggtgtttgat ctctttgcca    3300
ccttgagctt cggagcgacg ttagttcttc ccgctgggca tgaagaaaaa gatgcgttgc    3360
aatggaatcg cttaattgag cggcatcaag tgacgatttg gtctccgtc cccgctatct     3420 tggagatgtt gctctcttgc actcaagcag gcaattaca ctcacttcgt ctgattgccc      3480
aaggggggga ttacatcaaa cctgccacca tcgcccaatt acgcgctggt tcaaatccgc    3540
cgcggttgat ctctttgggc ggtcctaccg agacgacgat ttggagcatc tggcatgagc    3600
tgacggcaga tgatgtcagc gtgatcccat atggtcggcc gttggcggga accgttatt     3660 tcattatgga tgagatacaa cgccatgtac cgcaaggtgt ggtcggccgt atcttcacct    3720
ctggggtcaa tttagcgcaa ggttatcttg aagacggcga actgaaacaa accgattttg    3780
tcaccgtatt ggatgagcat ggccaccctg tgcgcgcgtt tcgaacgggc gatcaaggct    3840
actaccgcgc ggacggcaat atcatttttg ctagccgcat caatggttat gtgaaagttc    3900
gtggggtacg agtgtcactg ccggatatcg aaaagcagct gcaaactcat ccggcgctcg    3960
cgagcgtggt ggtggtcgat tatgcggata ctaatggaga taccgcttta gccgcattat    4020
ttagcgttaa acctcagcaa tcagcatcga gtcaggcgtt acgagagttt gccaaacaat    4080
cgctaccgtc ttcgcatatt ccgagtcggt ttattgcttt agaggcttta ccgctttctg    4140
cgaatggtaa agtggatcgc aaacagtgcc aagcgcatgt tcagcgacaa tcgatctctg    4200
ttgaaccagt aggtcaaccg aatcaaagtc aacctctctc accacctacc ttgtcatcgg    4260
cttccttgag tgagtttgaa cagcgagtct ggcgacagca tcaacgacat ggtgacggac    4320
gcaatcaata tgcgaccgct tatcgattga gcggaaaagt gaatatcgcg cgcttaatca    4380
cagcgctcag tcagttgccc aatcatttc cagtgttaaa ccgacgctat gtgcttgatg     4440
aggcatccgg cttaaccttg tactcggcga agccaacacc gcttgagatc cattttgagc    4500
atgttgagtc aatggatgag gcgtttgaac atcttgtgcg atggcaaaat cagccgatgg    4560
atttagccaa gcaagccaca ctaagttttt gcttgttgag tttggggagc gaagagcgag    4620
tgcttggggt gataagccat caaattatca gcgagcaatg ggattggcgg cgcgtatttg    4680
agtgcgtaac caatgggtat aaccaaatcg cctgtgacat cgatcctgtg atggagggg     4740 aggatctttc cctcggcttt acccctgtga tgccgcaaac gccattatcc caagcgttgt    4800
tgccgtggtt acagcctgcg agccacgcta catggattga gcagagcttg ccgagcgcaa    4860
atagcgccat caatacgctt tgcagtcgta aatatcggat tgcccatacac agcagcgtac   4920 tggcggagca tggtttagcg cagccggata agcaggaagt gcttgcactg atcgccgcgt    4980
```

```
tatttgctcg ctaccttgcc gcaagtgcga aacttggcca atttgagctt tacgttccgc    5040
atgatgtgga gcgcaaaacg cgtgagttga atggttctat gattgaaagc cagttggtgc    5100
atatcgccct taaaggcttt gagcgtccgc tttcgcaact gagccaagag atcttagacg    5160
ctatgcgcca gccgttaacg gggggagtcg ctagcgaaac tcacgcctct gccgcagcct    5220
tggtgacttg gttagtggat ccttcagtgc atctacaatt ggagggcttg cgctgcgaaa    5280
aattactttt tgcagccatg caccccaaat ttgaagtcgc cttgggggtt gggcttaatt    5340
gccaaggtgc cctagtactt gagctggcgt tagatgccac ggtttccccc catgtcggag    5400
cctacttgct tgagcaattt gtcgctgcga taggtgggcg aacaatgcct tcttcgacaa    5460
cctcatcctc tcatgtctca gccattgagt tgacgtcaaa caatccgccg acctcaaaca    5520
atgcgcatgc ggcgttggca gagtctgagc ttgaattgag cgctgtaaat tcctctgcgg    5580
ttgaagagtg cattttggct gagtttcgct cagcacttgg tgttgccgag atgacggcag    5640
aggatgattt ctttgatttt ggcggacatt ccctgatcgc aacgcgagtc attggtcgct    5700
tgttgagcga gcaaggtatt gaactgcaca tcaatgatat gtttagtttc cctaatgcca    5760
agcaactggc gcagcaagcc gtacttcacc gtaaacccac cagcacatca ttcgcagtga    5820
gtgaggtggt cgagtcgtcc aaagcgcctt tgtcgttagc acaagcctct ttatggaagg    5880
cgatgagcaa atacgccaag tttggtttga cccacatctt caatcttccg tttgcgctta    5940
aatttttaga tgaggtcaat gagcaagcat ttggtgaggc ttttcactgg cttttactgc    6000
gtcatgctgg gttacgaacc cactttggcc tagaagatgg gcagccttac cagcacgtga    6060
tcgcagccag caacatagaa cattaccagt ggttctggac gtctaaagat aacgccgccc    6120
aatccgtggc cagactactg gcgcaagagg ccgagcacac ctttgacctg agccaagaat    6180
tgccacttcg actcaatttc gtacgtgatg aacagacggg gacgcaatat cttTcacttc    6240
tgttccacca tattgtgttg gatgagtggt cgatcaatat tttgatggat gaattagcac    6300
aggtgtatca acacagtgtg caaggtactc gtccacagtg gcaaacggaa cccttacctt    6360
tccatgagtt tgctcgcaag cagcgttctt cggcattcaa tcaaacgcat cttaactatt    6420
ggttaaccaa gtttgccggt gtgccttggg cacagcctct gtttgctgcg gatcatcctt    6480
taagtaacag cactggcgtc gatcttggag aaggcggctg ggtcgaaata aaattgccga    6540
aatcaaccat ggtatcgctg tatcaattgg ctaaagcacg ccatgcttcg ttgtttaacg    6600
tgatgtatgc ggcgatttct gcgtcggtac attgtctcgg cgcaccagaa aagctgctgg    6660
ttggcacacc tgcttccggt cggctggatg ccgagttttt cgacacagtc ggttatttca    6720
ctaccatggg cgttcagttg gtggatttca cgaaagtaca aacggtgtgg caactcatcg    6780
agcaagtgaa aaacagcatt aaccagtcga tgccatacac agatattccg attgacctga    6840
ttgaagaagg gctcaaaggt gttgagcatg agacggaagg tcacatgttt gaggtcttta    6900
tacaactgca tgcaaaaaat aagctgcatg gagagctact gttgacagaa gggcatgcga    6960
tccgcttcca acaagtcgat cccgataaaa gtgaatccgg cttaggttta cagtttgaaa    7020
ttttagaaga gaggatcgag caaaagcaga cgttgagagt catgatgagt tatatgtcga    7080
aacactatag cccagctcaa gtcgctctgt tgaccaaggt aaccagtggc atgtttgagc    7140
ggttttccga ttgtattgca caagatattg cactgccgac gctgaaaaag caggtgaggc    7200
agcttgaaga tgaagcttgt cgctctccgt ccatgggggta g                        7241
```

<210> SEQ ID NO 7

<211> LENGTH: 1317
<212> TYPE: DNA
<213> ORGANISM: Vibrio cholera

<400> SEQUENCE: 7

```
gtgtctatgt tattggctca aaagcctttt tggcagcgcc atctggctta tcctcacatt    60
aatctcgaca ccgttgccca ttcgctacgc ctgacagggc ctttagatac cacactttg    120
ctgcgcgcat tgcatttaac cgtcagtgag atagatctgt tccgtgctcg ctttctgcg    180
caaggtgagc tgtattggca cccatttttct ccgcctatcg actatcaaga cctcagcatc    240
cacctttgaag cagaaccttt agcttggcgg caaatagagc aggatttaca gcgctcaagc    300
acactgattg acgcgccaat aacgagccat caagtgtatc gtttgtcaca cagtgagcac    360
cttatctata cccgtgcgca ccacattgtg ctggacggtt atggcatgat gctgtttgag    420
cagcgcctca gccaacatta ccaatccttg ctcagtgggc agacgccaac tgccgcgttt    480
aaaccttatc aatcctatct ggaagaagag gcggcttatc ttaccagcca tcgctactgg    540
caagataagc agttttggca aggctattta cgcgaagctc ccgacttaac gctcacctct    600
gcaacctatg atcctcaact tagtcatgcc gtgagcctct cttacacact caatagccaa    660
ctcaaccatt tgttactcaa gctcgctaac gcgaatcaga ttggctggcc tgatgccta    720
gtcgcgctgt gcgcgctcta tttggaatcg gctgaacctg atgcgccttg gctgtggctg    780
cccttatga accgatgggg cagcgtggcc gctaatgtgc ccggtttaat ggttaactcg    840
ctgcccttgc tgcgtctttc tgcgcagcaa acctcgctcg gcaactacct aaacagtca    900
gggcaagcga tacgctcact ctatttgcat ggccgctatc gaattgaaca atcgaacaa    960
gatcaagggc taaatgctga gcaaagttat tttatgagcc catttatcaa tattttgcct   1020
tttgaatccc cacactttgc tgattgccag actgagctca aggtgctggc ttcaggctct   1080
gcagaaggga ttaattttac ctttcgtggc tcaccccagc atgaactctg tctagacatc   1140
accgcagatt tagccagcta cccgcaatcc cactggcaaa gtcattgcga gcggtttcca   1200
cgttttttcg agcagttact cgcccgtttc caacaggtgg agcaagatgt tgcacgccta   1260
ctcgcagagc ctgcggcatt ggcagccacc acctccacac gggctatcgc cagttga     1317
```

<210> SEQ ID NO 8
<211> LENGTH: 8
<212> TYPE: PRT
<213> ORGANISM: Vibrio cholera

<400> SEQUENCE: 8

Asp Met Phe Val Ala Gly Leu Ile
1               5

<210> SEQ ID NO 9
<211> LENGTH: 8
<212> TYPE: PRT
<213> ORGANISM: Serratia plymuthica

<400> SEQUENCE: 9

Asp Met Phe Cys Ala Gly Leu Ile
1               5

<210> SEQ ID NO 10
<211> LENGTH: 8
<212> TYPE: PRT
<213> ORGANISM: Escherichia coli

<400> SEQUENCE: 10

```
Asp Val Trp His Phe Ser Leu Val
1               5

<210> SEQ ID NO 11
<211> LENGTH: 8
<212> TYPE: PRT
<213> ORGANISM: Mycobacterium tuberculosis

<400> SEQUENCE: 11

Asp Met Leu Asn Ala Gly Leu Val
1               5
```

COMPRESSED PATHWAYS FOR NONRIBOSOMAL MOLECULAR BIOSYNTHESIS

RELATED APPLICATIONS

This application is a national stage filing under 35 U.S.C. § 371 of international application number PCT/US2016/035728, filed Jun. 3, 2016, which was published under PCT Article 21(2) in English and claims the benefit under 35 U.S.C. § 119(e) of U.S. provisional application Ser. No. 62/171,651, filed Jun. 5, 2015, each of which is incorporated by reference herein in its entirety.

FEDERALLY SPONSORED RESEARCH

This invention was made with government support under Grant No. HDTRA1-14-1-0007 awarded by the Defense Threat Reduction Agency. The government has certain rights in the invention.

FIELD OF THE INVENTION

Aspects of the present disclosure relate to the general field of biotechnology and, more particularly, to the biosynthesis of compounds.

BACKGROUND OF THE INVENTION

Nonribosomal peptides (NRP) are a class of peptide secondary metabolites, often produced by microorganisms such as bacteria and fungi. Nonribosomal peptides are synthesized by nonribosomal peptide synthetases, which, unlike ribosomal peptides, are independent of messenger RNA. Each nonribosomal peptide synthetase can typically synthesize only one type of peptide, although the synthesis of most nonribosomal peptides requires more than one nonribosomal peptide synthetase. Nonribosomal peptides often have a cyclic and/or branched structures, can contain non-proteinogenic amino acids including D-amino acids, carry modifications such as N-methyl and N-formyl groups, and/or are glycosylated, acylated, halogenated or hydroxylated. Nonribosomal peptides are a diverse family of products with a broad range of biological activities and pharmacological properties. Examples of nonribosomal peptides include siderophores, and certain toxins, pigments, antibiotics, cytostatics and immunosuppressants.

SUMMARY OF THE INVENTION

Dihydroxybenzoate, synthesized from chorismate, is the precursor in the biosynthesis of several nonribosomal peptides, such as siderophores, including enterobactin (*Escherichia coli*) and vibriobactin (*Vibrio cholera*). The present disclosure is based, at least in part, on surprising results showing that a library of functionally and structurally diverse molecules (e.g., nonribosomal, iron-chelating proteins) can be produced by combining in a single bacterial cell a compressed pathway comprising select biosynthetic genes obtained from the *E. coli*. enterobactin gene cluster and select biosynthetic genes obtained from the *V. cholera* vibriobactin gene cluster, and then feeding the cells various amine or polyamine (e.g., diamine) linker precursors.

Peptides synthesized independently of the ribosome in plants, fungi and bacteria are clinically relevant molecules. They display anticancer, anti-hemochromatosis, and antiviral activity, among many others. Despite their natural origin, there is an increased difficulty in finding new molecules, as many niches, species and genomes get tapped. Thus, expanding the chemical diversity of libraries to include new entities can be challenging.

Provided herein are compressed synthetic pathways from *Escherichia coli* and *Vibrio cholerae* genes, capable of being programmed for the production of new, synthetic nonribosomal peptides. These molecules are analogs of the iron chelators, serratiochelins. While initially unable to be produced using the native biosynthetic genes, these molecules were successfully produced using ancestral homologs obtained from *Escherichia coli* and *Vibrio cholerae*. By expressing the ancestral homologs in *E. coli* and feeding the organism with different precursors, more than 30 molecules were produced, more than 20 of which are new and display high degrees of drug-likeness.

This new approach to the engineering of biosynthetic pathways, where ancestral genes from different pathways enable heterologous expression of nonribosomal peptides, allows for the bioproduction of many intractable molecules.

Some aspects of the present disclosure are directed to modified bacterial cells comprising a compressed biosynthetic pathway that comprises (a) biosynthetic genes obtained from one species encoding enzymes active in the bioassembly of a nonribosomal molecule, (b) biosynthetic genes obtained from another species encoding enzymes active in the bioassembly of a nonribosomal molecule that is different from the nonribosomal molecule of (a), and (c) a gene encoding an amide synthase.

Some aspects of the present disclosure are directed to modified bacterial cells comprising a compressed biosynthetic pathway that comprises (a) biosynthetic genes obtained from one species encoding enzymes active in the bioassembly of a nonribosomal molecule, (b) biosynthetic genes obtained from at least one other (e.g., at least two other) species encoding enzymes active in the bioassembly of at least one nonribosomal molecule that is different from the nonribosomal molecule of (a), and (c) a gene encoding an amide synthase.

In some embodiments, the biosynthetic genes of (a) are *Escherichia coli* biosynthetic genes. For example, the *Escherichia coli* biosynthetic genes may include entD gene, an entC gene, an entE gene, an entB gene and an entA gene.

In some embodiments, the biosynthetic genes of (b) are *Vibrio cholera* biosynthetic genes. For example, the *Vibrio cholera* biosynthetic genes may include a vibH gene and a vibF gene.

In some embodiments, the amide synthase is a vibH gene.

In some embodiments, the modified bacterial cell is a modified *Escherichia coli* cell. In some embodiments, endogenous entD, entC, entE, entB, entA and entF genes are deleted from the cell.

In some embodiments, the nonribosomal molecule is a nonribosomal peptide.

Some aspects of the present disclosure are directed to methods of producing a nonribosomal molecule, the method comprising culturing at least one of the modified bacterial cell provided herein, in the presence of an exogenous diamine linker precursor, under conditions that result in the production of a nonribosomal molecule that is different from the nonribosomal molecules of (a) and (b).

Some aspects of the present disclosure are directed to engineered vectors comprising a promoter operably linked to nucleic acid comprising an entD gene, an entC gene, an entE gene, an entB gene, an entA gene, a vibH gene and a vibF gene.

In some embodiments, the promoter is inducible.

The present disclosure also provides bacterial cells comprising the engineered vector as described herein.

Some aspects of the present disclosure are directed to methods of producing a nonribosomal molecule, the methods comprising culturing, in the presence of a diamine linker precursor at least one bacterial cell as described herein under conditions that result in the production of a nonribosomal molecule.

The present disclosure also provides nonribosomal molecules produced by the method as described herein.

Also provided herein are compounds of any one of formula (I)-(XXXVI) or (XXXVII)-(LV), or chemical analogs thereof (see Table 2).

Further provided herein are modified *Escherichia coli* (*E. coli*) cells that comprise an entA gene, an entB gene, an entC gene, an entD gene, a vibF gene, a vibH gene, and a deletion in an entF gene.

Some aspects provide methods comprising culturing a modified *E. coli* cell that comprises an entA gene, an entB gene, an entC gene, an entD gene, a vibF gene, a vibH gene, and a deletion in an entF gene in the presence of a polyamine linker precursor to produce a nonribosomal molecule.

Some aspects provide methods comprising culturing a modified *E. coli* cell that comprises an entA gene, an entB gene, an entC gene, an entD gene, a vibF gene, a vibH gene, and a deletion in an entF gene in the presence of an amine linker precursor to produce a nonribosomal molecule precuror.

Further provided herein are modified *Escherichia coli* (*E. coli*) cells that comprise an entB gene, an entD gene and an entE gene, a vibF gene, a vibH gene, a deletion in an entA gene, a deletion in an entC gene and a deletion in an entF gene.

The present disclosure also provides methods of culturing a modified *E. coli* cell that comprises a deletion in an entA gene, an entC gene and an entF gene, an entB gene, an entD gene and an entE gene, and a vibF gene and a vibH gene in the presence of a polyamine linker precursor and a polyhydroxybenzoate to produce a nonribosomal molecule.

In some embodiments, the polyhydroxybenzoate is 2,5-Dihydroxybenzoic acid (DHB). In some embodiments, the polyhydroxybenzoate is vanillic acid, gallic acid, caffeic acid, 5-Bromo-2,4-Dihydroxybenzoic acid or 3,4-Dihydroxy-5-methoxybenzoic acid.

In some embodiments, the modified *E. coli* cell is cultured in iron-deficient media (media that is free of iron, or media that contains less than 10% iron).

In some embodiments, the polyamine linker precursor is selected from the group consisting of: 1,3-Diaminopropane, N-(3-Aminopropyl)-1,4-diaminobutane, N,N'-Bis(3-aminopropyl)-1,4-diaminobutane, 1,5-Diaminopentane, 1,4-Butanediamine dihydrochloride, Bis(3-aminopropyl)amine, m-Xylylenediamine, N,N'-Bis(2-aminoethyl)-1,3-propanediamine, N-Benzylethylenediamine, 4-Aminobenzylamine, 4-(2-Aminoethyl)aniline, 4,4'-Oxydianiline, 4,4'-Diaminodiphenylmethane, 1,5-Diaminonaphthalene, 2,2'-Thiobisacetamide, Sulfaguanidine, p-Aminobenzenesulfonamide, Urea, N-Phenylthiourea, 3,3'-Diamino-N-methyldipropylamine, and 1, 8-Diaminooctane.

In some embodiments, the nonribosomal molecule is selected from the group consisting of: N-(4-(2,3-dihydroxybenzamido)butyl)-2-(2,3-dihydroxyphenyl)-5-methyl-4,5-dihydrooxazole-4-carboxamide; (2R,3S)-3-amino-4-((4-(2,3-dihydroxybenzamido)butyl)amino)-4-oxobutan-2-yl 2,3-dihydroxybenzoate; N-(5-(2,3-dihydroxybenzamido)pentyl)-2-(2,3-dihydroxyphenyl)-5-methyl-4,5-dihydrooxazole-4-carboxamide; (2R,3S)-3-amino-4-((5-(2,3-dihydroxybenzamido)pentyl)amino)-4-oxobutan-2-yl 2,3-dihydroxybenzoate; (4S)—N-(4-((3-(2,3-dihydroxybenzamido)propyl)amino)butyl)-2-(2,3-dihydroxyphenyl)-5-methyl-4,5-dihydrooxazole-4-carboxamide; N-(3-((4-((2S,3R)-2-(2,3-dihydroxybenzamido)-3-hydroxybutanamido)butyl)amino)propyl)-2,3-dihydroxybenzamide; N-(3-(2,3-dihydroxybenzamido)propyl)-2-(2,3-dihydroxyphenyl)-5-methyl-4,5-dihydrooxazole-4-carboxamide; (2R,3S)-3-amino-4-((3-(2,3-dihydroxybenzamido)propyl)amino)-4-oxobutan-2-yl 2,3-dihydroxybenzoate; N-(3-((2,3 dihydroxybenzamido)methyl)benzyl)-2-(2,3-dihydroxyphenyl)-5-methyl-4,5-dihydrooxazole-4-carboxamide; (2R,3S)-3-amino-4-((3-((2,3-dihydroxybenzamido)methyl)benzyl)amino)-4-oxobutan-2-yl 2,3-dihydroxybenzoate; N-(2-((3-((2-(2,3-dihydroxybenzamido)ethyl)amino)propyl)amino)ethyl)-2-(2,3-dihydroxyphenyl)-5-methyl-4,5-dihydrooxazole-4-carboxamide; (14S,15R)-14-amino-1-(2,3-dihydroxyphenyl)-1,13-dioxo-2,5,9,12-tetraazahexadecan-15-yl 2,3-; dihydroxybenzoate; N,N'-Bis (2-aminoethyl)-1,3-propanediamineN-(2-(N-benzyl-2,3-dihydroxybenzamido)ethyl)-2-(2,3-dihydroxyphenyl)-5-methyl-4,5-dihydrooxazole-4-carboxamide; (2R,3S)-3-amino-4-(benzyl(2-(2,3-dihydroxybenzamido)ethyl) amino)-4-oxobutan-2-yl 2,3-dihydroxybenzoate; N-(4-(2,3-dihydroxybenzamido)phenethyl)-2-(2,3-dihydroxyphenyl)-5-methyl-4,5-dihydrooxazole-4-carboxamide; (2R,3S)-3-amino-4-((4-(2-(2,3-dihydroxybenzamido)ethyl)phenyl)amino)-4-oxobutan-2-yl 2,3-dihydroxybenzoate; N-(4-(4-(2,3-dihydroxybenzamido)phenoxy)phenyl)-2-(2,3-dihydroxyphenyl)-5-methyl-4,5-dihydrooxazole-4-carboxamide; (2R,3S)-3-amino-4-((4-(4-(2,3-dihydroxybenzamido)phenoxy)phenyl)amino)-4-oxobutan-2-yl 2,3-dihydroxybenzoate; N-(4-(4-(2,3-dihydroxybenzamido)benzyl)phenyl)-2-(2,3-dihydroxyphenyl)-5-methyl-4,5-dihydrooxazole-4-carboxamide; (2R,3S)-3-amino-4-((4-(4-(2,3-dihydroxybenzamido)benzyl)phenyl)amino)-4-oxobutan-2-yl 2,3-dihydroxybenzoate; (4S)—N-(3-((4-((2-(2,3-dihydroxybenzamido)ethyl)amino)butyl)amino)propyl)-2-(2,3-dihydroxyphenyl)-5-methyl-4,5-dihydrooxazole-4-carboxamide; N-((16S,17R)-1-(2,3-dihydroxyphenyl)-17-hydroxy-1,15-dioxo-2,6,11,14-tetraazaoctadecan-16-yl)-2,3-dihydroxybenzamide; N-(5-(2,3-dihydroxybenzamido) naphthalen-1-yl)-2-(2,3-dihydroxyphenyl)-5-methyl-4,5-dihydrooxazole-4-carboxamide; (2R,3S)-3-amino-4-((5-(2,3-dihydroxybenzamido)naphthalen-1-yl)amino)-4-oxobutan-2-yl 2,3-dihydroxybenzoate; N-(2-((2-(2,3-dihydroxybenzamido)-2-oxoethyl)thio)acetyl)-2-(2,3-dihydroxyphenyl)-5-methyl-4,5-dihydrooxazole-4-carboxamide; (2R,3S)-3-amino-4-(2-((2-(2,3-dihydroxybenzamido)-2-oxoethyl)thio)acetamido)-4-oxobutan-2-yl 2,3-dihydroxybenzoate; N—(N-((4-(2,3-dihydroxybenzamido)phenyl)sulfonyl)carbamimidoyl)-2-2,3-dihydroxyphenyl)-5-methyl-4,5-dihydrooxazole-4-carboxamide; (2R,3S)-3-amino-4-((4-(N—((Z)—N'-(2,3-dihydroxybenzoyl)carbamimidoyl)sulfamoyl)phenyl); amino)-4-oxobutan-2-yl 2,3-dihydroxybenzoate; N-((4-(2, 3-dihydroxybenzamido)phenyl)sulfonyl)-2-(2,3-dihydroxyphenyl)-5-methyl-4,5-dihydrooxazole-4-carboxamide; (2R, 3S)-3-amino-4-((4-(N-(2,3-dihydroxybenzoyl)sulfamoyl) phenyl)amino)-4-oxobutan-2-yl 2,3-dihydroxybenzoate; N-((2,3-dihydroxybenzoyl)carbamoyl)-2-(2,3-dihydroxyphenyl)-5-methyl-4,5-dihydrooxazole-4-carboxamide; (2R, 3S)-3-amino-4-(3-(2,3-dihydroxybenzoyl)ureido)-4-oxobutan-2-yl 2,3-dihydroxybenzoate; N-((2,3-dihydroxybenzoyl)

(phenyl)carbamothioyl)-2-(2,3-dihydroxyphenyl)-5-methyl-4,5-dihydrooxazole-4-carboxamide; (2R,3S)-3-amino-4-(3-(2,3-dihydroxybenzoyl)-1-phenylthioureido)-4-oxobutan-2-yl 2,3-dihydroxybenzoate; N-(4-(2,3-dihydroxybenzamido)butyl)-2-(2,3-dihydroxyphenyl)-5-methyl-4,5-dihydrooxazole-4-carboxamide; (2R,3S)-3-amino-4-((4-(2,3-dihydroxybenzamido)butyl)amino)-4-oxobutan-2-yl 2,3-dihydroxybenzoate; (2R)-2-(2,3-dihydroxybenzamido)-3-(((2R)-2-(2,3-dihydroxybenzamido)-3-(((2R)-2-(2,3-dihydroxybenzamido)-3-hydroxybutanoyl)oxy)butanoyl)oxy)butanoic acid; (2R)-2-(2,3-dihydroxybenzamido)-3-(((2R)-2-(2,3-dihydroxybenzamido)-3-hydroxybutanoyl)oxy)butanoic acid; (2R)-2-(2,3-dihydroxybenzamido)-3-hydroxybutanoic acid; N-(3-aminopropyl)-2,3-dihydroxybenzamide; N-(3-((4-aminobutyl)amino)propyl)-2,3-dihydroxybenzamide; (S)—N-(3-((4-(2-(2,3-dihydroxybenzamido)-3-hydroxypropanamido)butyl)amino)propyl)-2,3-dihydroxybenzamide; (S)—N-(2-((4-((3-(2,3-dihydroxybenzamido)propyl)amino)butyl)amino)ethyl)-2-(2,3-dihydroxyphenyl)-4,5-dihydrooxazole-4-carboxamide; (S)—N-(1-(2,3-dihydroxyphenyl)-17-hydroxy-1,15-dioxo-2,6,11,14-tetraazaheptadecan-16-yl)-2,3-dihydroxybenzamide; N-(5-aminopentyl)-2,3-dihydroxybenzamide; N-(4-aminobutyl)-2,3-dihydroxybenzamide (Aminochelin); N-(3-((3-aminopropyl)amino)propyl)-2,3-dihydroxybenzamide; N-(3-(aminomethyl)benzyl)-2,3-dihydroxybenzamide; N-(2-(benzylamino)ethyl)-2,3-dihydroxybenzamide; (S)—N-benzyl-N-(2-(2,3-dihydroxybenzamido)ethyl)-2-(2,3-dihydroxyphenyl)-4,5-dihydrooxazole-4-carboxamide; N-(4-(aminomethyl)phenyl)-2,3-dihydroxybenzamide; N-(4-(2-aminoethyl)phenyl)-2,3-dihydroxybenzamide; N-(4-(4-aminophenoxy)phenyl)-2,3-dihydroxybenzamide; and N-(8-aminooctyl)-2,3-dihydroxybenzamide (or any one of the molecules listed in Table II or depicted in FIGS. 9A-9W).

Also provided herein are any of the foregoing nonribosomal molecules

The invention is not limited in its application to the details of construction and the arrangement of components set forth in the following description or illustrated in the drawings. The invention is capable of other embodiments and of being practiced or of being carried out in various ways. Each of the above embodiments and aspects may be linked to any other embodiment or aspect. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF THE DRAWINGS

The accompanying drawings are not intended to be drawn to scale. For purposes of clarity, not every component may be labeled in every drawing.

DETAILED DESCRIPTION OF THE INVENTION

Figure 1A:
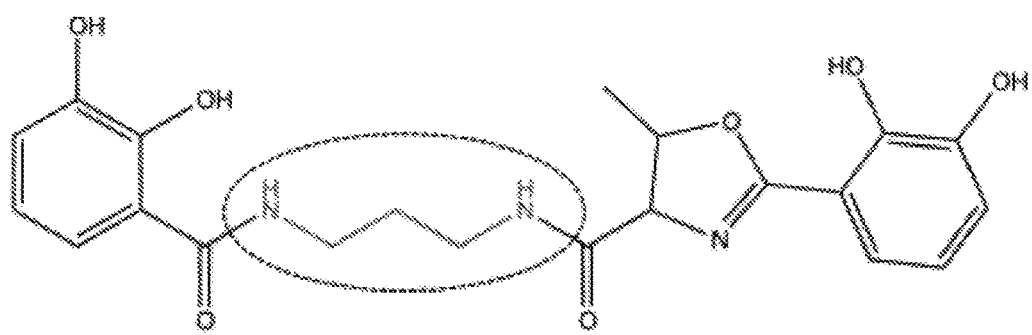
FIG. 1A shows the closed-ring chemical structure of a nonribosomal siderophore, serratiochelin, produced by *Serratia plymuthica*. The diamine linker is circled (dotted circle).

Provided herein, in some aspects, is a platform for producing structurally and functionally diverse nonribosomal molecules (e.g., nonribosomal peptides, for example, iron-chelating nonribosomal peptides, such as siderophores). This is achieved, in some embodiments, by expressing in modified bacterial cells "compressed" biosynthetic pathways that include clusters of biosynthetic genes obtained from heterologous organisms (e.g., two different species of bacteria, such as *Escherichia coli* and *Vibrio cholera*), that encode enzymes active in the bioassembly of nonribosomal molecules. Generally, by combining genes obtained from two different organisms, each organism capable of producing a single specific nonribosomal molecule, the platform provided herein can be used to produce non-naturally-occurring nonribosomal molecules, which differ structurally and functionally from the nonribosomal molecules produced naturally by each of the two organisms from which the biosynthetic genes were obtained. It should be understood that the platform provided herein, in some embodiments, may also be used to produce naturally-occurring NRPs (e.g., serratiochelin).

A prolific collection of metabolites, which have extended life expectancy and bettered quality of life, are naturally produced by plants, fungi and bacteria. Such metabolites are used in therapeutics capable of treating some of the most daunting pathologies, such as cancer and bacterial infections. These natural products have the particularity of not being a direct result of gene translation. Instead, they are assembled by very large enzymes. Depending on whether these enzymes catalyze reactions where an amino acid or a α-carboxyacyl-CoA is activated and condensed into nascent molecules, they are classified as nonribosomal peptides (NRP) or polyketides (PK), respectively. Less commonly, mixed-gene operons or hybrid genes can also generate hybrid molecules, with both NRP and PK character. The biosynthetic genes are composed of units (modules), each of which can be further divided into catalytic domains.

Described herein are combinations of precursor-directed biosynthesis, combinatorial genetics and heterologous expression of biosynthetic genes towards the assembly of new, unnatural molecules (e.g., nonribosomal peptides), in a programmable fashion and on demand. As an example, to demonstrate the capability of the methods of the present disclosure, iron-chelating nonribosomal peptides referred to as siderophores were produced. These molecules are key for cell survival under low-soluble iron availability. By linking the production of new molecules to survival, the organism used herein was driven to produce new molecules or otherwise perish. As discussed in the Examples, the *Serratia plymuthica* serratiochelin biosynthetic pathway was deconstructed and a simple and reduced pathway, incorporating only biosynthetic genes, was reconstructed. An equivalent pathway was also constructed, using homologous genes from *E. coli* and *V. cholerae*, which are responsible for the biosynthesis of enterobactin and vibriobactin, respectively. This homologous pathway was capable of generating both natural (e.g., serratiochelin and enterobactin) and non-natural molecules on demand, using exogenous supplementation of precursors, which were incorporated into the molecule. A "natural" or "naturally-occurring" molecule is one that is normally produced by an unmodified organism (in nature). It should be understood, however, that the modified organism and biosynthetic pathways described herein may be used to synthetically produce molecules that are found in nature.

Serratiochelin and enterobactin are examples of molecules that are produced synthetically using the methods provided herein and are also produced naturally by unmodified (e.g., not genetically modified or manipulated) organisms. The new, synthetic molecules assembled by the multi-enzymatic pathway were subsequently analyzed in silico to determine their usefulness at the clinical level.

Thus, the present disclosure provides, in some embodiments, for the use of ancestral, homologous genes, coupled with a lethal selective pressure, for successful heterologous expression of an assortment of new and unnatural/synthetic molecules (e.g., nonribosomal peptides).

Nonribosomal Molecules

Nonribosomal molecules—secondary metabolites generally produced by microorganism—are a diverse family of compounds with a broad range of biological activities and pharmacological properties. Nonribosomal peptides, for example, are synthesized independently of mRNA by non-ribosomal peptide-synthetases (NRPS). Generally, NRPS genes for specific peptides are contained in a single operon in bacteria and contain an initiation or starting module, elongation or extending modules, and a termination or releasing module. The initiation module may contain the following domains: F-domain (formylation), NMT-domain (N-methylation), A-domain (adenylation), and PCP-domain (thiolation and peptide carrier protein with attached 4'-phosphopantetheine). The elongation module may contain the following domains: condensation domain (forms amide bonds), cyclization domain (into thiazolines or oxazolines to thizolidines or oxazolidines), NMT-domain (N-methylation), A-domain (adenylation), PCP-domain (thiolation and peptide carrier protein), and E-domain (epimerization into D-amino acids). The termination module may contain the following domains: TE-domain (termination by a thioesterase) and R-domain (reduction to terminal aldehyde or alcohol).

Biosynthesis of nonribosomal peptides typically commences with a loading stage, during which the first amino acid is activated with ATP as a mixed acyl-phosphoric acid anhydride with AMP by the A-domain and is loaded onto the serine-attached 4'-phosphopantethine sidechain of the PCP-domain, resulting in thiolation. The newly-bound amino group may be formylated by an F-domain or methylated by an NMT-domain at this stage. During elongation, each module loads its specific amino acid onto its respective PCP-domain, and the C-domain catalyzes amide bond formation between the thioester group of the growing chain with the amino group of the current module, which attaches to the current PCP-domain. The C-domain may be replaced by the Cy-domain, which catalyzes the reaction of a serine, threonine, or cysteine sidechain with amides, forming oxazolidines and thiazolidine, respectively, in addition to the amide bond. An E-domain may be present, which epimerizes the innermost amino acid of the peptide chain to its D-configuration. The elongation cycle repeats for each elongation module present. During the termination stage, the TE-domain hydrolyzes the completed polypeptide chain from the ACP-domain of the final elongation module, often forming cyclic amides (lactams) or cyclic esters (lactones). Alternatively, the polypeptide may be released by an R-domain, which reduces the terminal aldehyde or alcohol's thioester bond. The released polypeptide may be further modified via glycosylation, acylation, halogenation, or hydroxylation due to the actions of enzymes usually associated with the synthetase complex. The polypeptide becomes functional after priming (attachment of the 4'-phosphopantetheine sidechain of acyl-CoA to the PCP-domain by 4'PP transferases) and deblocking (removal of the S-attached acyl group by specialized associated thioesterases).

There are several classes of nonribosomal molecules, any of which may be produced by the methods of the present disclosure, including, without limitation, pigments, antibiotics, such as actinomycin, bacitracin, calcium-dependent antibiotic, daptomycin, vancomycin, teixobactin, tyrocidine, gramicidin, zwittermicin A, antibiotic precursors, such as ACV-tripeptide, toxins, such as microcystins and nodularins, phytotoxins, such as HC-toxin, AM-toxin, and victorin, and immunosuppressants, such as ciclosporin. Cytostatics, which inhibit cell growth and multiplication, including epothilone and bleomycin, are also contemplated herein.

Some siderophores, which are small, high-affinity iron-chelating compounds, are also a result of nonribosomal peptide synthetases. Siderophores are secreted by microorganisms, including bacteria, fungi, and grasses, in response to environmental iron deficiencies. The molecules are excreted into the extracellular environment where they generally form a stable, hexadentate, octahedral complex preferentially with the $Fe^{3+}$ ion. The siderophores are then recognized by cell-specific receptors on the outer membrane and are transported across the cell membrane. Microbes usually reduce the ion to $Fe^{2+}$ internally, releasing it from the siderophore which has low affinity for the reduced ion.

There are three major groups of siderophores encompassing over 250 different structures: catecholates (including, enterobactin, from *E. coli*, bacillibactin, from *Bacillus subtillis* and *B. anthracis*, vibriobactin, from *Vibrio cholera*, and serratiochelin from *Serratia* sp.), hydroxamates (including ferrichrome, from *Ustilago sphaerogena*, Desferrioxamine B, from *Streptomyces pilosus*, Desferrioxamine E, from *Streptomyces coelicolor*, fusarinine C, from *Fusarium roseum*, ornibactin, from *Burkholderia cepacia*, and rhodotorulic acid, from *Rhodotorula pillmanae*), and carboxylates (derivatives of citric acid).

Compressed Biosynthetic Pathways

Figure 3:
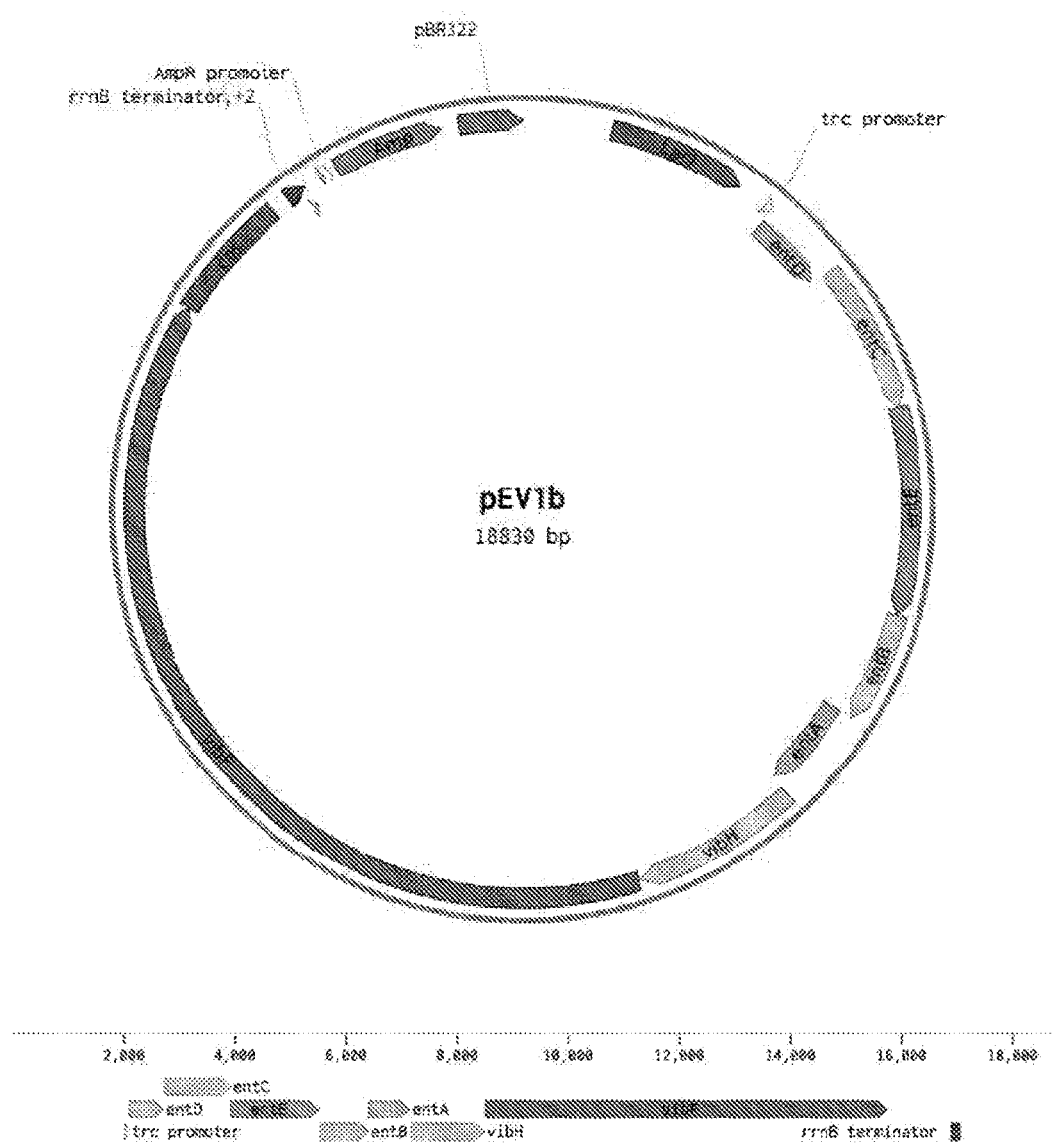
FIG. 3 depicts a plasmid map of the compressed pathway containing the following genes: entD, entC, entE, entB, entA, vibH and vibF, which was used to produce a library of functionally and structurally diverse nonribosomal peptides.

A "compressed biosynthetic pathway," as used herein, refers to a biosynthetic pathway (e.g., genes located on a single vector or on multiple vectors) that contains primarily (e.g., all) biosynthetic genes, which are genes actively involved in the bioassembly of a nonribosomal molecule (e.g., enterobactin, vibriobactin or serratiochelin). A biosynthetic pathway is considered to contain "primarily" biosynthetic genes if at least 80%, at least 85%, at least 95%, at least 98%, or at least 100% of the genes in the biosynthetic pathway are biosynthetic genes (as opposed to regulatory genes). For example, FIG. 3 depicts an example of a plasmid containing a compressed biosynthetic pathway of the present disclosure, whereby the genes of the pathway are primarily biosynthetic genes, including entD, entC, entE, entB, entA, vibH, and vibF (see Table 1).

TABLE 1

| Source | Gene | ID |
| --- | --- | --- |
| *Escherichia coli* str. K-12 substr. MG1655 (NC_000913.3) | entA | 945284 |
| | entB | 946178 |
| | entC | 945511 |
| | entD | 945194 |
| | entE | 947426 |
| *Vibrio cholera* E1 Tor A1552 (N16961) | vibH | 2615318 |
| | vibF | 2614958 |

Thus, examples of bioactive genes include, without limitation, entD, entF, entC, entE, entB, and entA of the *Escherichia coli* enterobactin gene cluster; vibH and vibF of the *Vibrio cholera* vibriobactin gene cluster; and schG, schF0, schC, schE, schB, schA, schH, schF2, schF1 and schF3 of the *Serratia plymuthica* V4 serratiochelin gene cluster. Other bioactive genes actively involved in the biosynthesis of nonribosomal proteins are contemplated herein.

Compressed biosynthetic pathways of the present disclosure typically contain genes obtained from at least two (e.g., 2, 3, 4 or more) different gene clusters obtained from at least two different organisms. A "cluster" of biosynthetic genes, as used herein, refers to a group of two or more biosynthetic genes found within an organism's genome that encode for similar molecules (e.g., polypeptides, or proteins), which collectively share a generalized function and are often located within a few thousand base pairs of each other. For example, entD, entF, entC, entE, entB, and entA are components of the *Escherichia coli* enterobactin gene cluster. As another example, vibH and vibF are components of the *Vibrio cholera* vibriobactin gene cluster. As yet another example schG, schF0, schC, schE, schB, schA, schH, schF2, schF1 and schF3 are components of the *S. plymuthica* V4 serratiochelin gene cluster. Thus, a compressed biosynthetic pathway may contain at least one (e.g., 1, 2, 3, 4, 5, or more) gene from the *Escherichia coli* enterobactin gene cluster and at least one gene from the *Vibrio cholera* vibriobactin gene cluster.

Nonribosomal molecules, such as nonribosomal peptides, are typically "bioassembled" from two or more compounds. For example, for the production of serratiochelin, an amide synthase (SchH) condenses diaminopropane with an acylated dihydroxybenzoyl intermediate, and SchF3 completes the synthesis of serratiochelin. Thus, serratiochelin is considered "bioassembled" from diaminopropane and acylated dihydroxybenzoyl. "Enzymes active in the bioassembly of a nonribosomal molecule" are enzymes that catalyze the bioassembly of a nonribosomal molecule. Such enzymes, in some embodiments, may be referred to as nonribosomal peptide synthetases (e.g., Strieker et al. Current Opinion in Structural Biology, 2010, 20, 2, 234-240, incorporated by reference herein).

An "amide synthase," as used herein, refers to an enzyme that catalyze the joining of either ammonia or an amide with another molecule, in which the linkage is in the form of a carbon-nitrogen bond (e.g., EC 6.3.1). Examples of amide synthases for use as provided herein include, without limitation, VibH and SchH.

Enterobactin Pathway

In some embodiments, genes of a compressed biosynthetic pathway are obtained from the *E. coli* enterobactin gene cluster (e.g., *Escherichia coli* MG1655). Enterobactin, N,N,N''-((3S,7S,11S)-2,6,10-trioxo-1,5,9-trioxacyclododecane-3,7,11-triyl)tris(2,3-dihydroxybenzamide), is a high affinity siderophore mainly found in Gram-negative bacteria, including *Escherichia coli* and *Salmonella typhimurium*. It is secreted from bacterial cells in response to iron deficiency, resulting in the formation of FeEnt, a coordination complex consisting of a ferric ion chelated to the conjugate base of enterobactin. In *E. coli*, FepA in the bacterial outer membrane permits entrance of FeEnt to the bacterial periplasm. Using an ATP-binding cassette transporter, FepB, C, D, and G all participate in the transportation of FeEnt through the inner membrane. Ferrienterobactin esterase then cleaves FeEnt to remove the iron, yielding three 2,3-dihydroxybenzoyl-L-serine units.

Enterobactin is created from chorismic acid, an aromatic amino acid precursor. Chorismic acid is converted to 2,3-dihydroxybenzoic acid (DHB) by a series of enzymes, EntA, EntB, and EntC. DHB forms an amide link to L-serine through reactions catalyzed by EntD, EntE, EntF, and EntB. Three molecules of DHB-Ser undergo intermolecular cyclization, resulting in the formation of enterobactin.

Several protein-coding genes are found in *E. coli* and are necessary for the formation of enterobactin. EntA, 2,3-dihydro-2,3-dihydroxybenzoate dehydrogenase, is a protein-coding gene found in *E. coli*. It catalyzes the formation of DHB. EntB, 2,3-dihydro-2,3-dihydroxybenzoate synthase, is an aryl carrier protein that is converted into its holo-form by EntD and then activates DHB. EntC, isochorismate synthase, catalyzes the reversible conversion of chorismate to isochorismate during the formation of enterobactin. EntD encodes an Sfp-type phosphopantetheinyl transferase (PPTase) and catalyzes the transfer of the 4'-phosphopantetheine (Ppant) moiety from coenzyme A to the apo-domains of EntB and EntF, resulting in their respective holo-forms. The holo-forms of EntB and EntF then activate DHB and L-serine, respectively. EntE, 2,3-dihydroxybenzoate-AMP ligase, catalyzes the formation of an amide link between DHB and L-serine. EntF, a four domain (condensation-adenylation-peptidyl carrier protein-thioesterase) nonribosomal peptide synthase, cyclotrimerizes lactone synthase and catalyzes an elongation to permit the ester-bond formation between covalently tethered DHB-serine moieties.

Vibriobactin Pathway

In some embodiments, genes of a compressed biosynthetic pathway are obtained from the *V. cholera* vibriobactin gene cluster (e.g., *Vibrio cholera* El Tor A1552). Vibriobactin, N(1)-(2,3-dihydroxybenzoyl)-N(5),N(9)-bis[2-(2,3-dihydroxyphenyl)-5-methyloxazolinyl-4-carboxamido]norspermidine, is a siderophore synthesized in *Vibrio cholerae*. It is biosynthezied from three molecules of 2,3-dihydroxybenzoate (DHB), two molecules of L-threonine, and one molecule of norspermidine. The reactions leading to functional mature vibriobactin require several nonribosomal peptide synthases, in a process analogous to that described for enterobactin above. VibE and VibB are homologous to EntE and EntB, respectively, from *Escherichia coli* enterobactin synthetase; VibE, a 2,3-dihydroxybenzoate-adenosyl monophosphate ligase, activates DHB as the acyl adenylate and then transfers it to the free thiol of the phosphopantetheine arm of VibB's aryl carrier protein domain. VibB is a bifunctional isochorismate lyase-aryl carrier protein (ArCP). VibH, a novel amide synthase that acts as a free-standing condensation (C) domain, condenses the resulting DHB thioester (the donor) with the small molecule norspermidine (the acceptor), forming N(1)-(2,3-dihydroxybenzoyl)norspermidine (DHB-NSPD). VibH acts upon an upstream carrier-protein-bound donor and a downstream amine, resulting in a soluble amide product, in contrast to an archetypal NRPS-embedded C domain that condenses two carrier protein thioesters. VibF contains a rare NRPS domain organization: cyclization-cyclization-adenylation-condensation-peptidyl carrier protein-condensation. It activates and covalently loads its PCP with L-threonine, and together with VibE and VibB, it condenses and heterocyclizes 2,3-dihydroxybenzoyl-VibB with L-Thr to 2-dihydroxyphenyl-5-methyloxazolinyl-4-carboxy-VibF, an oxazoline. The enzyme-bound aryl oxazoline can be transferred by VibF to various amine acceptors, but it is transferred most efficiently to N(1)-(2,3-dihydroxybenzoyl)norspermidine), the product of 2,3-dihydroxybenzoyl-VibB, norspermidine, and VibH. The diacylated product then undergoes a second aryl oxazoline acylation on its remaining secondary amine, also catalyzed by VibF, and yields vibriobactin.

Serratiochelin Pathway

In some embodiments, genes of a compressed biosynthetic pathway are obtained from the Serrati asp. or *S. plymuthica* V4 serratiochelin gene clusters (which include two clusters located at different loci). Serratiochelins, biscatecholate siderophores, may be tetra- or hexadentate in structure. They contain a propane-1,3-diamine linker and are found in *Serratia* species. One of the serratiochelin gene clusters (ca. 21 kb) contains genes schCEBAGF0 and the other (ca. 15 kb) contains genes schF1F2F3H. Some of the serratiochelin genes are involved in siderophore export or ferric-siderophore uptake and utilization. The remaining six genes are involved in serratiochelin synthesis. SchG, homologous to acetolactate synthase, catalyzes the first step in branched-chain amino acid synthesis. The remaining five genes show high sequence identity with the corresponding enterobactin-synthesizing genes. SchC, similar to EntC, is a putative isochorismate synthase, and catalyzes the reaction of chorismate to isochorismate. SchB, similar to EntB, is a bifunctional isochorismate lyase-aryl carrier protein (ArCP), which generates the next intermediate. SchA, similar to EntA, is a dehydrogenase, which converts the intermediate to 2,3-dihydroxybenzoate. SchE, like EntE, adenylates 2,3-dyhydroxybenzoate and transfers it to the ArCP domain of SchB. SchF0 may incorporate L-threonine into serratiochelin. SchH, with a 45% sequence similarity to VibH, is also required for the biosynthesis of serratiochelin. It is a free-standing amide synthase and condenses a diamine with the acylated dihydroxybenzoyl intermediate. SchF1, SchF2, and SchF3 match the domain architecture of VibF completely; SchF1 is a putative free-standing NRPS cyclization domain, SchF2 is a putative Cy-A domain, where the A domain codes for L-threonine, and SchF3 matches the C-terminal domain of VibF, containing a C-T-C domain arrangement and finishing the biosynthesis of the serratiochelin.

Nucleic Acids

A "nucleic acid" is at least two nucleotides covalently linked together, and in some instances, may contain phosphodiester bonds (e.g., a phosphodiester "backbone"). An "engineered nucleic acid" is a nucleic acid that does not occur in nature. It should be understood, however, that while an engineered nucleic acid as a whole is not naturally-occurring, it may include nucleotide sequences that occur in nature. In some embodiments, an engineered nucleic acid comprises nucleotide sequences from different organisms (e.g., from different species). For example, in some embodiments, an engineered nucleic acid includes a murine nucleotide sequence, a bacterial nucleotide sequence, a human nucleotide sequence, and/or a viral nucleotide sequence. Engineered nucleic acids include recombinant nucleic acids and synthetic nucleic acids. A "recombinant nucleic acid" is a molecule that is constructed by joining nucleic acids (e.g., isolated nucleic acids, synthetic nucleic acids or a combination thereof) and, in some embodiments, can replicate in a living cell. A "synthetic nucleic acid" is a molecule that is amplified or chemically, or by other means, synthesized. A synthetic nucleic acid includes those that are chemically modified, or otherwise modified, but can base pair with naturally-occurring nucleic acid molecules. Recombinant and synthetic nucleic acids also include those molecules that result from the replication of either of the foregoing.

In some embodiments, a nucleic acid of the present disclosure is considered to be a nucleic acid analog, which may contain, at least in part, other backbones comprising, for example, phosphoramide, phosphorothioate, phosphorodithioate, O-methylphophoroamidite linkages and/or peptide nucleic acids. A nucleic acid may be single-stranded (ss) or double-stranded (ds), as specified, or may contain portions of both single-stranded and double-stranded sequence. In some embodiments, a nucleic acid may contain portions of triple-stranded sequence. A nucleic acid may be DNA, both genomic and/or cDNA, RNA or a hybrid, where the nucleic acid contains any combination of deoxyribonucleotides and ribonucleotides (e.g., artificial or natural), and any combination of bases, including uracil, adenine, thymine, cytosine, guanine, inosine, xanthine, hypoxanthine, isocytosine and isoguanine.

Nucleic acids of the present disclosure may include one or more genetic elements. A "genetic element" refers to a particular nucleotide sequence that has a role in nucleic acid expression (e.g., promoter, enhancer, terminator) or encodes a discrete product of an engineered nucleic acid (e.g., a nucleotide sequence encoding a guide RNA, a protein and/or an RNA interference molecule).

Nucleic acids of the present disclosure may be produced using standard molecular biology methods (see, e.g., Green and Sambrook, Molecular Cloning, A Laboratory Manual, 2012, Cold Spring Harbor Press).

In some embodiments, nucleic acids are produced using GIBSON ASSEMBLY® Cloning (see, e.g., Gibson, D. G. et al. *Nature Methods,* 343-345, 2009; and Gibson, D. G. et al. *Nature Methods,* 901-903, 2010, each of which is incorporated by reference herein). GIBSON ASSEMBLY® typically uses three enzymatic activities in a single-tube reaction: 5' exonuclease, the 3' extension activity of a DNA polymerase and DNA ligase activity. The 5' exonuclease activity chews back the 5' end sequences and exposes the complementary sequence for annealing. The polymerase activity then fills in the gaps on the annealed regions. A DNA ligase then seals the nick and covalently links the DNA fragments together. The overlapping sequence of adjoining fragments is much longer than those used in Golden Gate Assembly, and therefore results in a higher percentage of correct assemblies.

Vector and Associated Genetic Elements

In some embodiments, a compressed biosynthetic pathway is delivered to a cell on a vector. A "vector" refers to a nucleic acid (e.g., DNA) used as a vehicle to artificially carry genetic material (e.g., an engineered nucleic acid construct) into a cell where, for example, it can be replicated and/or expressed. In some embodiments, a vector is an episomal vector (see, e.g., Van Craenenbroeck K. et al. *Eur. J. Biochem.* 267, 5665, 2000, incorporated by reference herein). A non-limiting example of a vector is a plasmid (e.g., FIG. 3). Plasmids are double-stranded generally circular DNA sequences that are capable of automatically replicating in a host cell. Plasmid vectors typically contain an origin of replication that allows for semi-independent replication of the plasmid in the host and also the transgene insert. Plasmids may have more features, including, for example, a "multiple cloning site," which includes nucleotide overhangs for insertion of a nucleic acid insert, and multiple restriction enzyme consensus sites to either side of the insert. Another non-limiting example of a vector is a viral vector.

Expression of compressed biosynthetic pathway is driven by a promoter operably linked to a nucleic acid containing the genes of the pathway. A "promoter" refers to a control region of a nucleic acid sequence at which initiation and rate of transcription of the remainder of a nucleic acid sequence are controlled. A promoter drives expression or drives transcription of the nucleic acid sequence that it regulates. A promoter may also contain sub-regions at which regulatory proteins and molecules may bind, such as RNA polymerase and other transcription factors. Promoters may be constitutive, inducible, activatable, repressible, tissue-specific or any combination thereof.

Herein, a promoter is considered to be "operably linked" when it is in a correct functional location and orientation in relation to a nucleic acid sequence it regulates to control ("drive") transcriptional initiation and/or expression of that sequence.

A promoter may be one naturally associated with a gene or sequence, as may be obtained by isolating the 5' non-coding sequences located upstream of the coding segment of a given gene or sequence. Such a promoter can be referred to as "endogenous."

In some embodiments, a coding nucleic acid sequence may be positioned under the control of a recombinant or heterologous promoter, which refers to a promoter that is not normally associated with the encoded sequence in its natural environment. Such promoters may include promoters of other genes; promoters isolated from any other cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR) (see U.S. Pat. No. 4,683,202 5,928,906).

In some embodiments, a promoter is an "inducible promoter," which refer to a promoter that is characterized by regulating (e.g., initiating or activating) transcriptional activity when in the presence of, influenced by or contacted by an inducer signal. An inducer signal may be endogenous or a normally exogenous condition (e.g., light), compound (e.g., chemical or non-chemical compound) or protein that contacts an inducible promoter in such a way as to be active in regulating transcriptional activity from the inducible promoter. Thus, a "signal that regulates transcription" of a nucleic acid refers to an inducer signal that acts on an inducible promoter. A signal that regulates transcription may activate or inactivate transcription, depending on the regulatory system used. Activation of transcription may involve directly acting on a promoter to drive transcription or indirectly acting on a promoter by inactivation a repressor that is preventing the promoter from driving transcription. Conversely, deactivation of transcription may involve directly acting on a promoter to prevent transcription or indirectly acting on a promoter by activating a repressor that then acts on the promoter.

The administration or removal of an inducer signal results in a switch between activation and inactivation of the transcription of the operably linked nucleic acid sequence. Thus, the active state of a promoter operably linked to a nucleic acid sequence refers to the state when the promoter is actively regulating transcription of the nucleic acid sequence (i.e., the linked nucleic acid sequence is expressed). Conversely, the inactive state of a promoter operably linked to a nucleic acid sequence refers to the state when the promoter is not actively regulating transcription of the nucleic acid sequence (i.e., the linked nucleic acid sequence is not expressed).

An inducible promoter of the present disclosure may be induced by (or repressed by) one or more physiological condition(s), such as changes in light, pH, temperature, radiation, osmotic pressure, saline gradients, cell surface binding, and the concentration of one or more extrinsic or intrinsic inducing agent(s). An extrinsic inducer signal or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof.

Inducible promoters of the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some embodiments, an inducer signal of the present disclosure is an N-acyl homoserine lactone (AHL), which is a class of signaling molecules involved in bacterial quorum sensing. Quorum sensing is a method of communication between bacteria that enables the coordination of group based behavior based on population density. AHL can diffuse across cell membranes and is stable in growth media over a range of pH values. AHL can bind to transcriptional activators such as LuxR and stimulate transcription from cognate promoters.

In some embodiments, an inducer signal of the present disclosure is anhydrotetracycline (aTc), which is a derivative of tetracycline that exhibits no antibiotic activity and is designed for use with tetracycline-controlled gene expression systems, for example, in bacteria.

Other inducible promoter systems are known in the art and may be used in accordance with the present disclosure.

In some embodiments, inducible promoters of the present disclosure function in prokaryotic cells (e.g., bacterial cells). Examples of inducible promoters for use prokaryotic cells include, without limitation, bacteriophage promoters (e.g. Pls1con, T3, T7, SP6, PL) and bacterial promoters (e.g., Pbad, PmgrB, Ptrc2, Plac/ara, Ptac, Pm), or hybrids thereof (e.g. PLlacO, PLtetO). Examples of bacterial promoters for use in accordance with the present disclosure include, without limitation, positively regulated *E. coli* promoters such as positively regulated σ70 promoters (e.g., inducible pBad/araC promoter, Lux cassette right promoter, modified lamdba Prm promote, plac Or2-62 (positive), pBad/AraC with extra REN sites, pBad, P(Las) TetO, P(Las) CIO, P(Rhl), Pu, FecA, pRE, cadC, hns, pLas, pLux), σS promoters (e.g., Pdps), σ32 promoters (e.g., heat shock) and σ54 promoters (e.g., glnAp2); negatively regulated *E. coli* promoters such as negatively regulated σ70 promoters (e.g., Promoter (PRM+), modified lamdba Prm promoter, TetR-TetR-4C P(Las) TetO, P(Las) CIO, P(Lac) IQ, RecA_DlexO_D-LacO1, dapAp, FecA, Pspac-hy, pcI, plux-cI, plux-lac, CinR, CinL, glucose controlled, modified Pr, modified Prm+, FecA, Pcya, rec A (SOS), Rec A (SOS), EmrR regulated, BetI regulated, pLac_lux, pTet_Lac, pLac/Mnt, pTet/Mnt, LsrA/cI, pLux/cI, LacI, LacIQ, pLacIQ1, pLas/cI, pLas/Lux, pLux/Las, pRecA with LexA binding site, reverse BBa_R0011, pLacI/ara-1, pLacIq, rrnB P1, cadC, hns, PfhuA, pBad/araC, nhaA, OmpF, RcnR), σS promoters (e.g., Lutz-Bujard LacO with alternative sigma factor 038), σ32 promoters (e.g., Lutz-Bujard LacO with alternative sigma factor σ32), and σ54 promoters (e.g., glnAp2); negatively regulated *B. subtilis* promoters such as repressible *B. subtilis* 6A promoters (e.g., Gram-positive IPTG-inducible, Xyl, hyper-spank) and σB promoters. Other inducible microbial promoters may be used in accordance with the present disclosure.

Cells and Cell Expression

Nucleic acids of the present disclosure may be expressed in a broad range of host cell types. In some embodiments, engineered nucleic acids are expressed in bacterial cells, yeast cells, insect cells, mammalian cells or other types of cells.

Bacterial cells of the present disclosure include bacterial subdivisions of *Eubacteria* and *Archaebacteria*. *Eubacteria* can be further subdivided into gram-positive and gram-negative *Eubacteria*, which depend upon a difference in cell wall structure. Also included herein are those classified based on gross morphology alone (e.g., cocci, bacilli). In some embodiments, the bacterial cells are Gram-negative cells, and in some embodiments, the bacterial cells are Gram-positive cells. Examples of bacterial cells of the present disclosure include, without limitation, cells from *Escherichia* spp., *Yersinia* spp., *Klebsiella* spp., *Acinetobacter* spp., *Bordetella* spp., *Neisseria* spp., *Aeromonas* spp., *Franciesella* spp., *Corynebacterium* spp., *Citrobacter* spp., *Chlamydia* spp., Hemophilus spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp., or *Lactobacillus* spp. In some embodiments, the bacterial cells are from *Bacteroides thetaiotaomicron, Bacteroidesfragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus actinobycetemcomitans, cyanobacteria, Escherichia coli, Helicobacterpylori, Selnomonas ruminatium, Shigella sonnei, Zymomonas mobilis, Mycoplasma mycoides, Treponema denticola, Bacillus thuringiensis, Staphylococcus lugdunensis, Leuconostoc oenos, Corynebacterium xerosis, Lactobacillus plantarum, Lactobacillus rhamnosus, Lactobacillus casei, Lactobacillus acidophilus, Streptococcus* spp., *Enterococcus faecalis, Bacillus coagulans, Bacillus ceretus, Bacillus popillae, Synechocystis* strain PCC6803, *Bacillus liquefaciens, Pyrococcus abyssi, Selenomonas nominantium, Lactobacillus hilgardii, Streptococcus ferus, Lactobacillus pentosus, Bacteroidesfragilis, Staphylococcus epidermidis, Zymomonas mobilis, Streptomyces phaechromogenes,* or *Streptomyces ghanaenis*. "Endogenous" bacterial cells refer to non-pathogenic bacteria that are part of a normal internal ecosystem such as bacterial flora.

In some embodiments, bacterial cells of the invention are anaerobic bacterial cells (e.g., cells that do not require oxygen for growth). Anaerobic bacterial cells include facultative anaerobic cells such as, for example, *Escherichia coli, Shewanella oneidensis* and *Listeria monocytogenes*.

Anaerobic bacterial cells also include obligate anaerobic cells such as, for example, *Bacteroides* and *Clostridium* species.

In some embodiments, the bacterial cells are *Escherichia coli* (*E. coli*) cells. *E. coli* is a Gram-negative, anaerobic, rod-shaped bacterium commonly found in the large intestine of endotherms. Frequently used as prokaryotic model organism, *E. coli* contains a circular DNA molecule of 4288 annotated protein-coding genes, seven ribosomal RNA operons, and 86 transfer RNA genes. The genome contains a number of transposable genetic elements, repeat elements, cryptic prophages, and bacteriophage remnants as well. As a host cell, *E. coli* is versatile, allowing for the production of heterologous proteins and molecular cloning into its vector plasmids.

Cells of the present disclosure, in some embodiments, are modified. A modified cell is a cell that contains an exogenous nucleic acid or a nucleic acid that does not occur in nature (e.g., an engineered nucleic acid). In some embodiments, a modified cell contains a mutation in a genomic nucleic acid. In some embodiments, a modified cell contains an exogenous independently replicating nucleic acid (e.g., an engineered nucleic acid present on an episomal vector). In some embodiments, a modified cell is produced by introducing a foreign or exogenous nucleic acid into a cell. A nucleic acid may be introduced into a cell by conventional methods, such as, for example, electroporation (see, e.g., Heiser W. C. *Transcription Factor Protocols: Methods in Molecular Biology*™ 2000; 130: 117-134), chemical (e.g., calcium phosphate or lipid) transfection (see, e.g., Lewis W. H., et al., *Somatic Cell Genet.* 1980 May; 6(3): 333-47; Chen C., et al., *Mol Cell Biol.* 1987 August; 7(8): 2745-2752), fusion with bacterial protoplasts containing recombinant plasmids (see, e.g., Schaffner W. *Proc Natl Acad Sci USA.* 1980 April; 77(4): 2163-7), transduction, conjugation, or microinjection of purified DNA directly into the nucleus of the cell (see, e.g., Capecchi M. R. *Cell.* 1980 November; 22(2 Pt 2): 479-88).

In some embodiments, a cell is modified to express a reporter molecule. In some embodiments, a cell is modified to express an inducible promoter operably linked to a reporter molecule (e.g., a fluorescent protein such as green fluorescent protein (GFP) or other reporter molecule).

In some embodiments, a cell is modified to overexpress an endogenous protein of interest (e.g., via introducing or modifying a promoter or other regulatory element near the endogenous gene that encodes the protein of interest to increase its expression level). In some embodiments, a cell is modified by mutagenesis. In some embodiments, a cell is modified by introducing an engineered nucleic acid into the cell in order to produce a genetic change of interest (e.g., via insertion or homologous recombination).

In some embodiments, a modified cell contains a gene deletion. That is, a cell may be modified to remove a gene normally expressed in nature. In some embodiments, a cell is an *Escherichia coli* cell containing one or more of the following gene deletions: ΔentD, Δ entC, ΔentE, ΔentB, ΔentA and ΔentF.

Methods of Producing Nonribosomal Molecules

Some aspects of the present disclosure are directed to methods of producing a nonribosomal molecule, the methods comprising culturing at least one modified cell comprising a compressed biosynthetic pathway, in the presence of an exogenous polyamine (e.g., diamine) linker precursor, under conditions that result in the production of a nonribosomal molecule. Other aspects of the present disclosure are directed to methods of producing a nonribosomal molecule precursor, the methods comprising culturing at least one modified cell comprising a compressed biosynthetic pathway, in the presence of an exogenous amine linker precursor, under conditions that result in the production of a nonribosomal molecule precursor.

"Conditions that result in the production of a nonribosomal molecules" may be vary and may be based on any one or more of the following conditions: type of cell used for gene expression, volume of cell culture, composition of cell culture media, length of cell culture period, and temperature at which cells are cultured.

In some embodiments, cells are cultured in minimal medium, which, in some embodiments, is optimized for production of a particular nonribosomal molecule of interest.

Minimal medium may comprise, in some embodiments, $Na_2HPO_4$ (e.g., 1 to 10 g/L, such as 4 to 6 g/L (e.g., 5.96 g/L)), $K_2HPO_4$ (e.g., 1 to 10 g/L, such as 1 to 4 g/L (e.g., 3.0 g/L)), $NH_4Cl$ (e.g., 1 to 10 g/L, such as 1 to 3 g/L (e.g., 1.0 g/L)), NaCl (e.g., 1 to 10 g/L, such as 1 to 2 g/L (e.g., 0.5 g/L)), $MgSO_4$ (0.05 to 1 g/L, such as 0.05 to 1.0 g/L (e.g., 0.058 g/L)), $C_6H_{12}O_6$ (e.g., 1 to 10 g/L, such as 4 to 6 g/L (e.g., 5.0 g/L)) and IPTG (e.g., 1 to 5 nM, such as 2 to 3 mM (e.g., 1 mM)).

In some embodiments, the cells are cultured at a pH of 4 to 8, or 4 to 10. For example, the cells may be cultured at a pH of 4, 5, 6, 7, 8, 9 or 10. In some embodiments, the cells are cultured at (e.g., the minimal medium has) a pH value of 7.0.

In some embodiments, cells (e.g., bacterial cells) are cultured in the presence of an exogenous polyamine linker precursor. A "polyamine linker precursor," as used herein, refers to an amine that has at least two amine groups with one or two hydrogen atoms. Non-limiting examples of polyamine linker precursor are shown in Table 2 and include norspermidine, cadaverine, spermidine, diaminopropane, m-xylylenediamine, N,N'-bis(2-aminoethyl)-1,3-propanediamine, N-benzylethylenediamine, 4-(2-Aminoethyl)aniline, 4,4'-oxydianiline, 4,4'-diaminodiphenylmethane, spermine, 1,5-diaminonaphthalene, 2,2'-thiobisacetamide, sulfaguanidine, p-aminobenzenesulfonamide, urea, N-phenylthiourea and putrescine. An "amine linker precursor" refers to an amine group with at least one hydrogen atom.

In some embodiments, the precursors are added to a cell culture or other reaction medium at a final concentration of 0.1 μM to 0.05 mM (e.g., 0.1, 0.2, 0.3, 0.4, 0.5, 0.6, 0.7, 0.8, 0.9, 1, 2, 5, 10, 15, 20, 25, 30, 35, 40, 45 or 50 μM), or 0.05 to 20 mM (e.g., 0.5, 1, 2, 3, 4, 5, 6, 7, 8, 9, 10, 11, 12, 13, 14, 15, 16, 17, 18, 19 or 20 mM).

In some embodiments, an iron chelator is added to a cell culture or reaction medium. For example, 2,2'-bipyridyl may be added to a cell culture or reaction medium. An iron chelator, in some embodiments, may be added to a final concentration of 0.05 to 1 mM (e.g., 0.05, 0.1, 0.15 mM).

In some embodiments, the cells are grown (e.g., cultured) for 1 to 20 days (e.g., 1, 2, 3, 4, 5, 6, 7, 8, 9, 10, 11, 12, 13, 14, 15, 16, 17, 18, 19 or 20 days), or more, with or without shaking (e.g., 200 to 250 rpm). For example, cell may be cultured for 1 to 5, 1 to 10, or 1 to 15. In some embodiments, cells are cultured for 5 days.

Compositions and Molecules

Also provided herein are compositions comprising nonribosomal molecules (e.g., nonribosomal peptide) produced by the methods of the present disclosure. A composition may comprise any one or more of the nonribosomal molecules listed in Table 2, or an analog thereof.

TABLE 2

| Formula | Name | Structure |
|---|---|---|
| I | N-(4-(2,3-dihydroxy-benzamido)butyl)-2-(2,3-dihydroxyphenyl)-5-methyl-4,5-dihydrooxazole-4-carboxamide<br>Exact Mass: 486.21 | 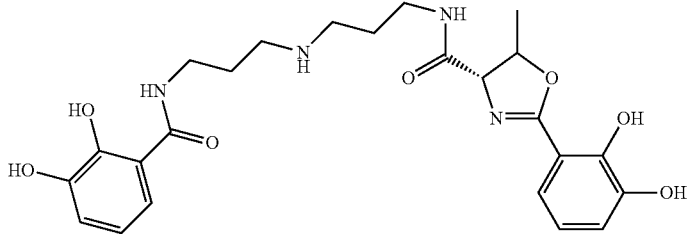 [SMILES: CC1OC(c2cccc(O)c2O)=N[C@@H]1C(=O)NCCCNCCCNC(=O)c1cccc(O)c1O] |
| II | (2R,3S)-3-amino-4-((4-(2,3-dihydroxybenzamido)butyl)amino)-4-oxobutan-2-yl 2,3-dihydroxybenzoate<br>Exact Mass: 504.22 | 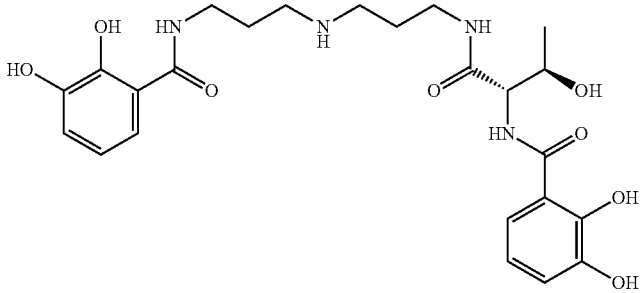 [SMILES: C[C@@H](O)[C@H](NC(=O)c1cccc(O)c1O)C(=O)NCCCNCCCNC(=O)c1cccc(O)c1O] |
| | Precursor for I and II: Norspermidine | 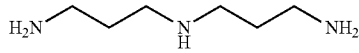 |
| III | N-(5-(2,3-dihydroxy-benzamido)pentyl)-2-(2,3-dihydroxyphenyl)-5-methyl-4,5-dihydrooxazole-4-carboxamide<br>Exact Mass: 457.18 | 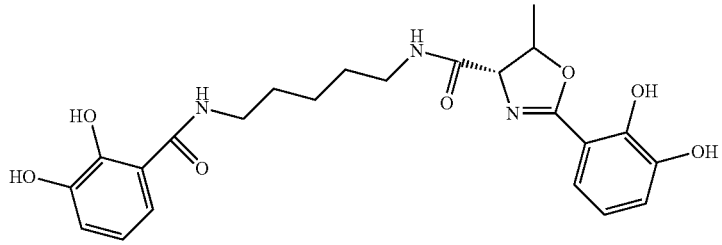 [SMILES: CC1OC(c2cccc(O)c2O)=N[C@@H]1C(=O)NCCCCCNC(=O)c1cccc(O)c1O] |
| IV | (2R,3S)-3-amino-4-((5-(2,3-dihydroxybenzamido)pentyl)amino)-4-oxobutan-2-yl 2,3-dihydroxybenzoate<br>Exact Mass: 475.20 | 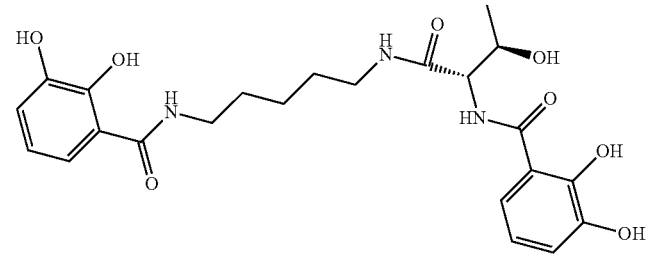 [SMILES: C[C@@H](O)[C@H](NC(=O)c1cccc(O)c1O)C(=O)NCCCCCNC(=O)c1cccc(O)c1O] |
| | Precursor for III and IV: Cadaverine | 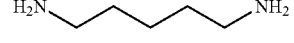 |
| V | (4S)-N-(4-((3-(2,3-dihydroxybenzamido)propyl)amino)butyl)-2-(2,3-dihydroxyphenyl)-5-methyl-4,5-dihydrooxazole-4-carboxamide<br>Exact Mass: 500.23 | 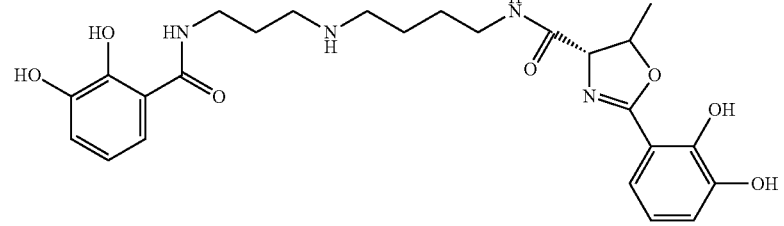 |

TABLE 2-continued

Nonribosomal molecules

| Formula | Name | Structure |
|---|---|---|
| VI | N-(3-((4-((2S,3R)-2-(2,3-dihydroxybenzamido)-3-hydroxybutanamido)butyl)amino)propyl)-2,3-dihydroxybenzamide<br>Exact Mass: 518.24 | 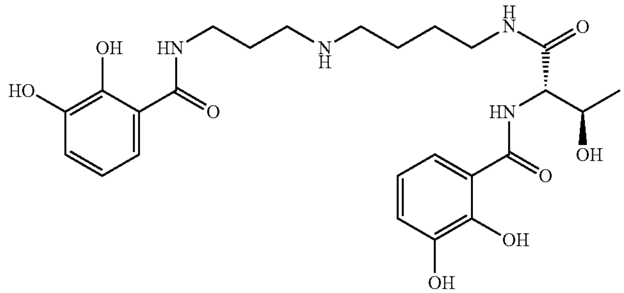 [SMILES: C[C@@H](O)[C@H](NC(=O)c1cccc(O)c1O)C(=O)NCCCCNCCCNC(=O)c1cccc(O)c1O] |
| | Precursor for V and VI: Spermidine | |
| VII | N-(3-(2,3-dihydroxy-benzamido)propyl)-2-(2,3-dihydroxy-phenyl)-5-methyl-4,5-dihydrooxazole-4-carboxamide<br>Exact Mass: 429.15 | 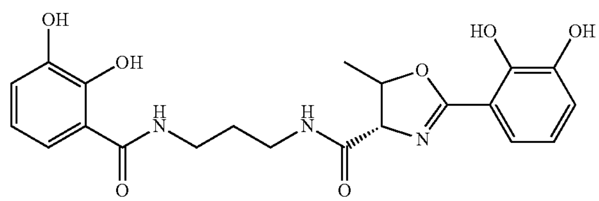 [SMILES: CC1OC(c2cccc(O)c2O)=N[C@@H]1C(=O)NCCCNC(=O)c1cccc(O)c1O] |
| VIII | (2R,3S)-3-amino-4-((3-(2,3-dihydroxybenzamido)propyl)amino)-4-oxobutan-2-yl 2,3-dihydroxybenzoate<br>Exact Mass: 447.16 | 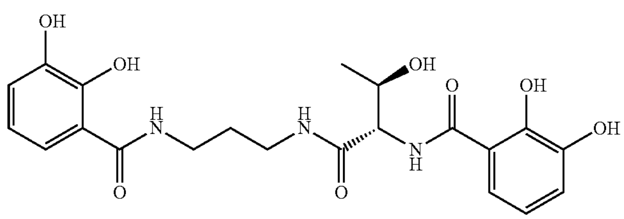 [SMILES: C[C@@H](O)[C@H](NC(=O)c1cccc(O)c1O)C(=O)NCCCNC(=O)c1cccc(O)c1O] |
| | Precursor for VII and VIII: Diaminopropane | |
| IX | N-(3-((2,3 dihydroxy-benzamido)methyl)benzyl)-2-(2,3-dihydroxyphenyl)-5-methyl-4,5-dihydrooxazole-4-carboxamide<br>Exact Mass: 491.17 | 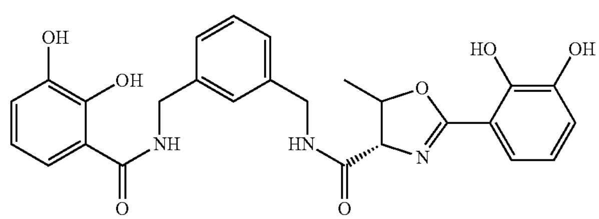 [SMILES: CC1OC(c2cccc(O)c2O)=N[C@@H]1C(=O)NCc1cccc(CNC(=O)c2cccc(O)c2O)c1] |
| X | (2R,3S)-3-amino-4-((3-((2,3-dihydroxybenzamido)methyl)benzyl)amino)-4-oxobutan-2-yl 2,3-dihydroxybenzoate<br>Exact Mass: 5091.8 | 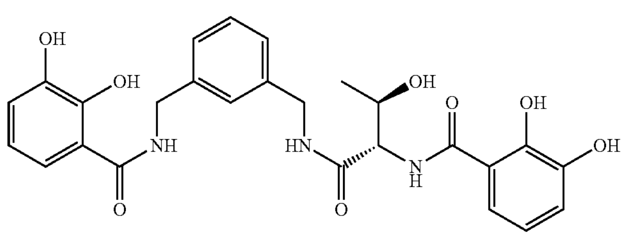 [SMILES: C[C@@H](O)[C@H](NC(=O)c1cccc(O)c1O)C(=O)NCc1cccc(CNC(=O)c2cccc(O)c2O)c1] |
| | Precursor for IX and X: m-Xylylenediaminee | |

TABLE 2-continued

Nonribosomal molecules

| Formula | Name | Structure |
|---|---|---|
| XI | N-(2-((3-((2-(2,3-dihydroxybenzamido)ethyl)amino)propyl)amino)ethyl)-2-(2,3-dihydroxyphenyl)-5-methyl-4,5-dihydrooxazole-4-carboxamide<br>Exact Mass: 515.24 | 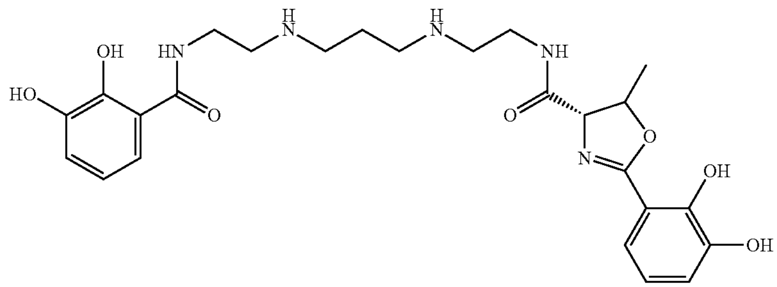 [SMILES: CC1OC(c2cccc(O)c2O)=N[C@@H]1C(=O)NCCNCCCNCCNC(=O)c1cccc(O)c1O] |
| XII | (14S,15R)-14-amino-1-(2,3-dihydroxyphenyl)-1,13-dioxo-2,5,9,12-tetraazahexadecan-15-yl 2,3-dihydroxybenzoate<br>Exact Mass: 533.25 | 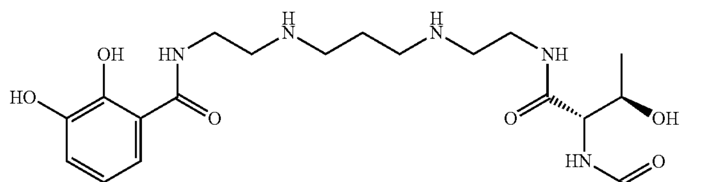 |
| | Precursor for XI and XII: N,N'-Bis(2-aminoethyl)-1,3-propanediamine | |
| XIII | N-(2-(N-benzyl-2,3-dihydroxy-benzamido)ethyl)-2-(2,3-dihydroxyphenyl)-5-methyl-4,5-dihydrooxazole-4-carboxamide<br>Exact Mass: 505.18 | 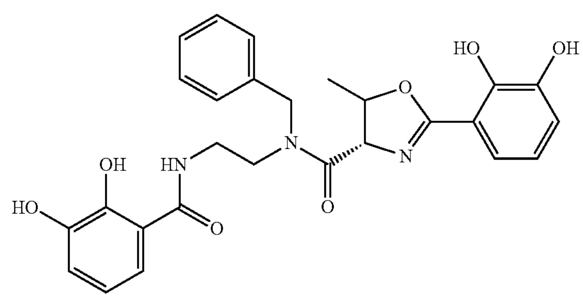 [SMILES: CC1OC(c2cccc(O)c2O)=N[C@@H]1C(=O)N(CCNC(=O)c1cccc(O)c1O)Cc1ccccc1] |
| XIV | (2R,3S)-3-amino-4-(benzyl(2-(2,3-dihydroxy-benzamido)ethyl)amino)-4-oxobutan-2-yl 2,3-dihydroxybenzoate<br>Exact Mass: 523.20 | 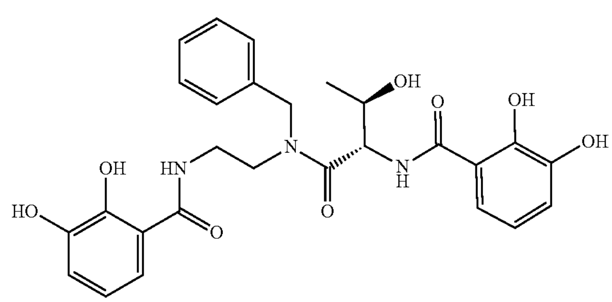 [SMILES: C[C@@H](O)[C@H](NC(=O)c1cccc(O)c1O)C(=O)N(CCNC(=O)c1cccc(O)c1O)Cc1ccccc1] |
| | Precursor for XIII and XIV: N-Benzylethylene-diamine | |

TABLE 2-continued

Nonribosomal molecules

| Formula | Name |
|---|---|
| XV | N-(4-(2,3-dihydroxybenzamido)phenethyl)-2-(2,3-dihydroxyphenyl)-5-methyl-4,5-dihydrooxazole-4-carboxamide<br>Exact Mass: 491.17 |
| XVI | (2R,3S)-3-amino-4-((4-(2-(2,3-dihydroxybenzamido)ethyl)phenyl)amino)-4-oxobutan-2-yl 2,3-dihydroxybenzoate<br>Exact Mass: 509.18 |
| | Precursor for XV and XVI:<br>4-(2-Aminoethyl)aniline |
| XVII | N-(4-(4-(2,3-dihydroxybenzamido)phenoxy)phenyl)-2-(2,3-dihydroxyphenyl)-5-methyl-4,5-dihydrooxazole-4-carboxamide<br>Exact Mass: 555.16 |
| XVIII | (2R,3S)-3-amino-4-((4-(4-(2,3-dihydroxybenzamido)phenoxy)phenyl)amino)-4-oxobutan-2-yl 2,3-dihydroxybenzoate<br>Exact Mass: 573.17 |
| | Precursor for XVII and XVIII:<br>4,4'-Oxydianiline |

TABLE 2-continued

Nonribosomal molecules

| Formula | Name | Structure |
|---|---|---|
| XIX | N-(4-(4-(2,3-dihydroxybenzamido)benzyl)phenyl)-2-(2,3-dihydroxyphenyl)-5-methyl-4,5-dihydrooxazole-4-carboxamide<br>Exact Mass: 553.18 | 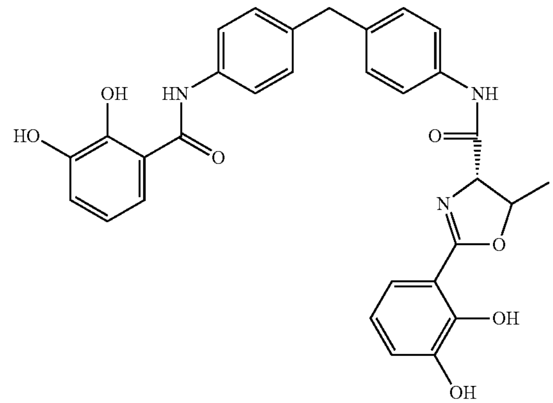 [SMILES: CC1OC(c2cccc(O)c2O)=N[C@@H]1C(=O)Nc1ccc(Cc2ccc(NC(=O)c3cccc(O)c3O)cc2)cc1] |
| XX | (2R,3S)-3-amino-4-((4-(4-(2,3-dihydroxybenzamido)benzyl)phenyl)amino)-4-oxobutan-2-yl 2,3-dihydroxybenzoate<br>Exact Mass: 571.20 | 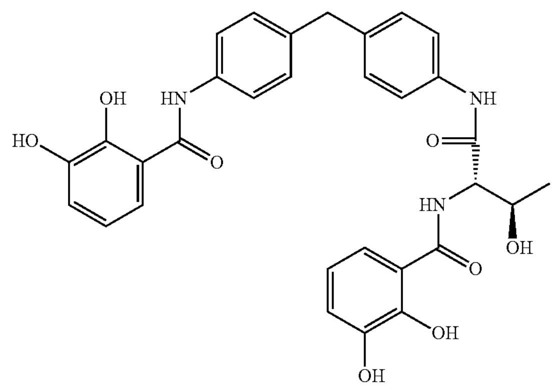 [SMILES: C[C@@H](O)[C@H](NC(=O)c1cccc(O)c1O)C(=O)Nc1ccc(Cc2ccc(NC(=O)c3cccc(O)c3O)cc2)cc1] |
| | Precursor for XIX and XX:<br>4,4'-Diamino-diphenylmethane | |
| XXI | (4S)-N-(3-((4-((2-(2,3-dihydroxybenzamido)ethyl)amino)butyl)amino)propyl)-2-(2,3-dihydroxyphenyl)-5-methyl-4,5-dihydrooxazole-4-carboxamide<br>Exact Mass: 557.28 | 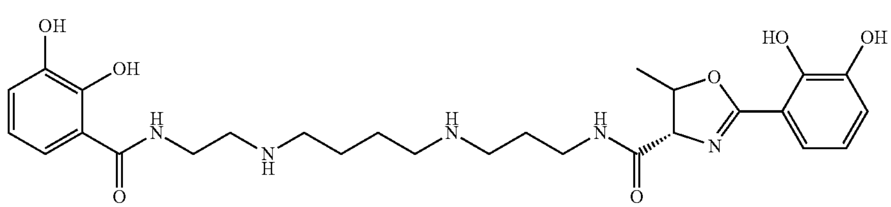 [SMILES: CC1OC(c2cccc(O)c2O)=N[C@@H]1C(=O)NCCCNCCCCNCCNC(=O)c1cccc(O)c1O] |
| XXII | (19S,20R)-19-amino-1-(2,3-dihydroxyphenyl)-1,18-dioxo-3,7,12,16-tetraazahenicosan-20-yl 2,3-dihydroxybenzoate<br>Exact Mass: 603.33 | 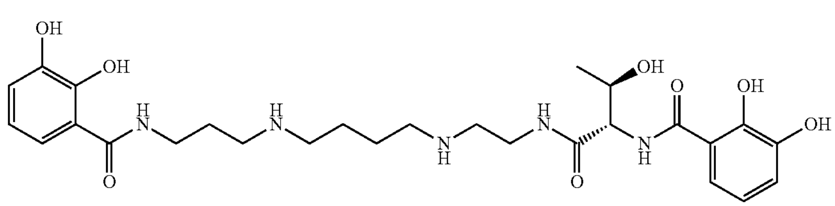 [SMILES: C[C@@H](O)[C@H](NC(=O)c1cccc(O)c1O)C(=O)NCCNCCCCNCCCNC(=O)c1cccc(O)c1O] |
| | Precursor for XXI and XXII: Spermine | |

TABLE 2-continued

Nonribosomal molecules

| Formula | Name | Structure |
|---|---|---|
| XXIII | N-(5-(2,3-dihydroxybenzamido)naphthalen-1-yl)-2-(2,3-dihydroxyphenyl)-5-methyl-4,5-dihydrooxazole-4-carboxamide<br>Exact Mass: 513.15 | 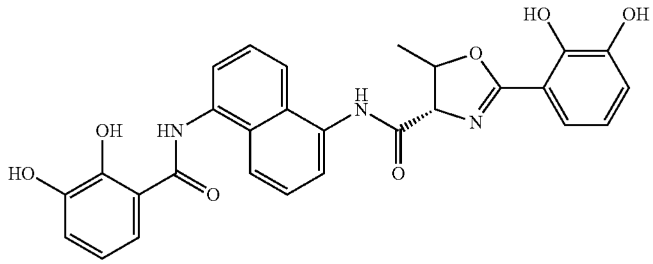 [SMILES: CC1OC(c2cccc(O)c2O)=N[C@@H]1C(=O)Nc1cccc2c(NC(=O)c3cccc(O)c3O)cccc12] |
| XXIV | (2R,3S)-3-amino-4-((5-(2,3-dihydroxybenzamido)naphthalen-1-yl)amino)-4-oxobutan-2-yl 2,3-dihydroxybenzoate<br>Exact Mass: 531.16 | 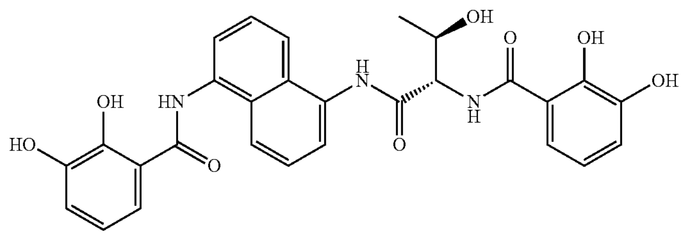 [SMILES: C[C@@H](O)[C@H](NC(=O)c1cccc(O)c1O)C(=O)Nc1cccc2c(NC(=O)c3cccc(O)c3O)cccc12] |
| | Precursor for XXIII and XXIV:<br>1,5-Diaminoaphthalene | |
| XXV | N-(2-((2-(2,3-dihydroxybenzamido)-2-oxoethyl)thio)acetyl)-2-(2,3-dihydroxyphenyl)-5-methyl-4,5-dihydrooxazole-4-carboxamide<br>Exact Mass: 503.10 | 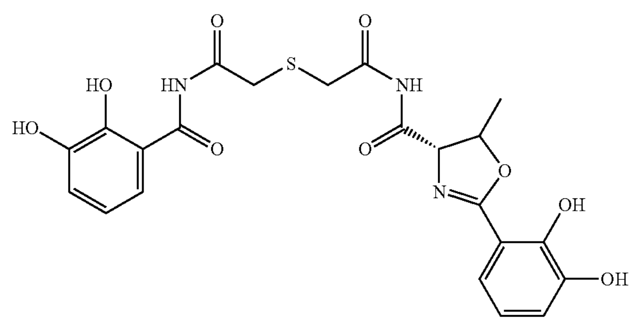 [SMILES: CC1OC(c2cccc(O)c2O)=N[C@@H]1C(=O)NC(=O)CSCC(=O)NC(=O)c1cccc(O)c1O] |
| XXVI | (2R,3S)-3-amino-4-(2-((2-(2,3-dihydroxybenzamido)-2-oxoethyl)thio)acetamido)-4-oxobutan-2-yl 2,3-dihydroxybenzoate<br>Exact Mass: 521.11 | 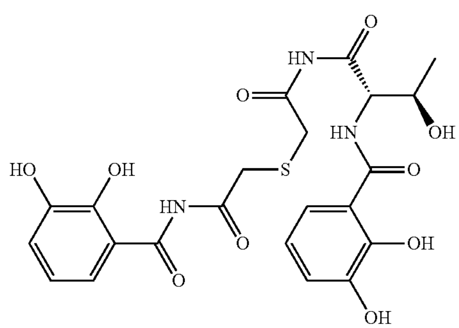 [SMILES: C[C@@H](O)[C@H](NC(=O)c1cccc(O)c1O)C(=O)NC(=O)CSCC(=O)NC(=O)c1cccc(O)c1O] |
| | Precursor for XXV and XXVI:<br>2,2'-Thiobisacetamide | |

TABLE 2-continued

Nonribosomal molecules

| Formula | Name | Structure |
|---|---|---|
| XXVII | N-(N-((4-(2,3-dihydroxybenzamido)phenyl)sulfonyl)carbamimidoyl)-2-(2,3-dihydroxyphenyl)-5-methyl-4,5-dihydrooxazole-4-carboxamide<br>Exact Mass: 569.12 | 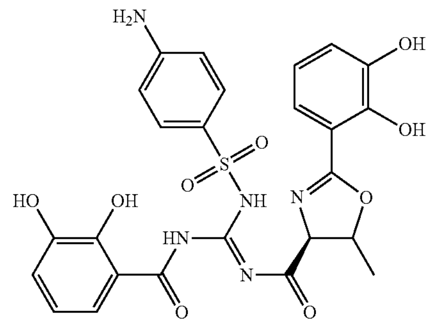 [SMILES: CC1OC(c2cccc(O)c2O)=N[C@@H]1C(=O)/N=C(/NC(=O)c1cccc(O)c1O)NS(=O)(=O)c1ccc(N)cc1] |
| XXVIII | (2R,3S)-3-amino-4-((4-(N-((Z)-N'-(2,3-dihydroxybenzoyl)carbamimidoyl)sulfamoyl)phenyl)amino)-4-oxobutan-2-yl 2,3-dihydroxybenzoate<br>Exact Mass: 587.13 | 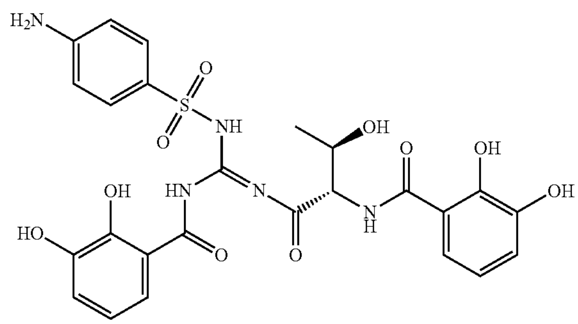 [SMILES: C[C@@H](O)[C@H](NC(=O)c1cccc(O)c1O)C(=O)N=C(NC(=O)c1cccc(O)c1O)NS(=O)(=O)c1ccc(N)cc1] |
| | Precursor for XXVII and XXVIII:<br>Sulfaguanidine | |
| XXIX | N-((4-(2,3-dihydroxybenzamido)phenyl)sulfonyl)-2-(2,3-dihydroxyphenyl)-5-methyl-4,5-dihydrooxazole-4-carboxamide<br>Exact Mass: 527.10 | 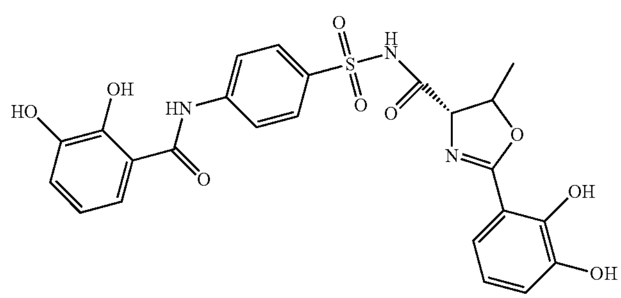 [SMILES: CC1OC(c2cccc(O)c2O)=N[C@@H]1C(=O)NS(=O)(=O)c1ccc(NC(=O)c2cccc(O)c2O)cc1] |
| XXX | (2R,3S)-3-amino-4-((4-(N-(2,3-dihydroxybenzoyl)sulfamoyl)phenyl)amino)-4-oxobutan-2-yl 2,3-dihydroxybenzoate<br>Exact Mass: 545.11 | 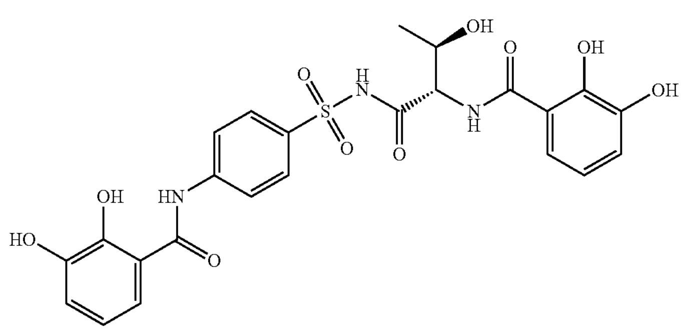 [SMILES: C[C@@H](O)[C@H](NC(=O)c1cccc(O)c1O)C(=O)NS(=O)(=O)c1ccc(NC(=O)c2cccc(O)c2O)cc1] |
| | Precursor for XXIX and XXX;<br>p-Aminobenzenesulfonamide | |

TABLE 2-continued

Nonribosomal molecules

| Formula | Name | Structure |
|---|---|---|
| XXXI | N-((2,3-dihydroxybenzoyl)carbamoyl)-2-(2,3-dihydroxyphenyl)-5-methyl-4,5-dihydrooxazole-4-carboxamide<br>Exact Mass: 415.10 | 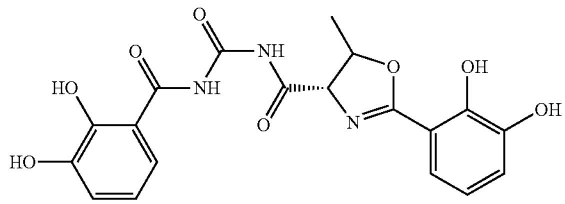 [SMILES: CC1OC(c2cccc(O)c2O)=N[C@@H]1C(=O)NC(=O)NC(=O)c1cccc(O)c1O] |
| XXXII | (2R,3S)-3-amino-4-(3-(2,3-dihydroxybenzoyl)ureido)-4-oxobutan-2-yl 2,3-dihydroxybenzoate<br>Exact Mass: 433.11 | 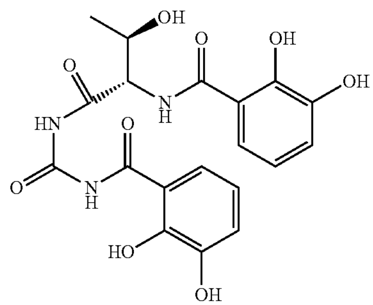 [SMILES: C[C@@H](O)[C@H](NC(=O)c1cccc(O)c1O)C(=O)NC(=O)NC(=O)c1cccc(O)c1O] |
| | Precursor for XXXI and XXXII: Urea | |
| XXXIII | N-((2,3-dihydroxybenzoyl)(phenyl)carbamothioyl)-2-(2,3-dihydroxyphenyl)-5-methyl-4,5-dihydrooxazole-4-carboxamide<br>Exact Mass: 507.11 | 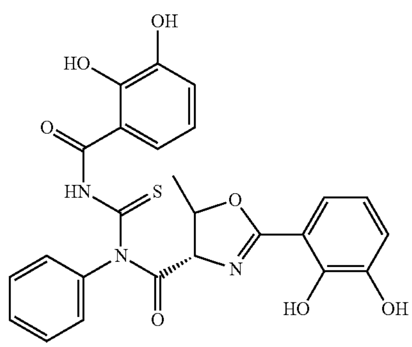 [SMILES: CC1OC(c2cccc(O)c2O)=N[C@@H]1C(=O)N(C(=S)NC(=O)c1cccc(O)c1O)c1ccccc1] |
| XXXIV | (2R,3S)-3-amino-4-(3-(2,3-dihydroxybenzoyl)-1-phenylthioureido)-4-oxobutan-2-yl 2,3-dihydroxybenzoate<br>Exact Mass: 525.12 | 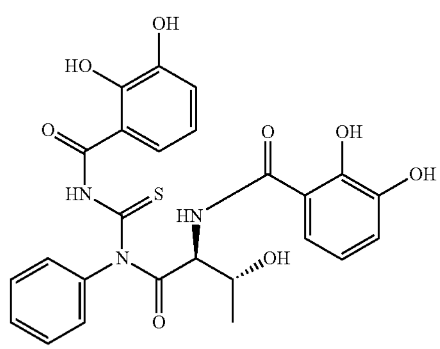 [SMILES: C[C@@H](O)[C@H](NC(=O)c1cccc(O)c1O)C(=O)N(C(=S)NC(=O)c1cccc(O)c1O)c1ccccc1] |
| | Precursor for XXXIII and XXXIV: N-Phenylthiourea | |

TABLE 2-continued

Nonribosomal molecules

| Formula | Name | Structure |
|---|---|---|
| XXXV | N-(4-(2,3-dihydroxy-benzamido)butyl)-2-(2,3-dihydroxyphenyl)-5-methyl-4,5-dihydrooxazole-4-carboxamide<br>Exact Mass: 443.17 | 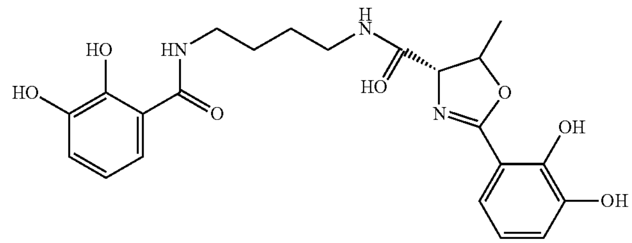 [SMILES: CC1OC(c2cccc(O)c2O)=N[C@@H]1C(=O)NCCCCNC(=O)c1cccc(O)c1O] |
| XXXVI | (2R,3S)-3-amino-4-((4-(2,3-dihydroxybenzamido)butyl)amino)-4-oxobutan-2-yl 2,3-dihydroxybenzoate<br>Exact Mass: 461.18 | 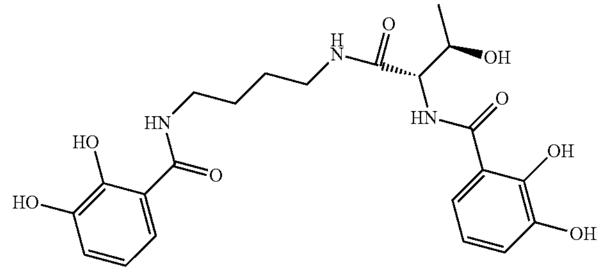 [SMILES: C[C@@H](O)[C@H](NC(=O)c1cccc(O)c1O)C(=O)NCCCCNC(=O)c1cccc(O)c1O] |
| XXXVII | Precursor for XXXV and XXXVI:<br>Putrescine | 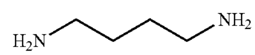 |
| XXXVIII | (2R)-2-(2,3-dihydroxybenzamido)-3-(((2R)-2-(2,3-dihydroxybenzamido)-3-(((2R)-2-(2,3-dihydroxybenzamido)-3-hydroxybutanoyl)oxy)butanoyl)oxy)butanoic acid<br>Exact Mass: 729.2017 | 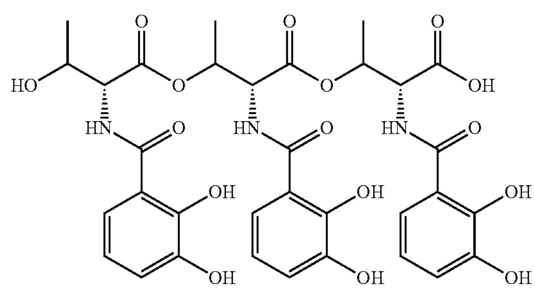 [SMILES: CC(O)[C@@H](NC(=O)c1cccc(O)c1O)C(=O)OC(C)[C@@H](NC(=O)c1cccc(O)c1O)C(=O)OC(C)[C@@H](NC(=O)c1cccc(O)c1O)C(=O)O] |
| XXXIX | (2R)-2-(2,3-dihydroxybenzamido)-3-(((2R)-2-(2,3-dihydroxybenzamido)-3-hydroxybutanoyl)oxy)butanoic acid<br>Exact Mass: 492.1380 | 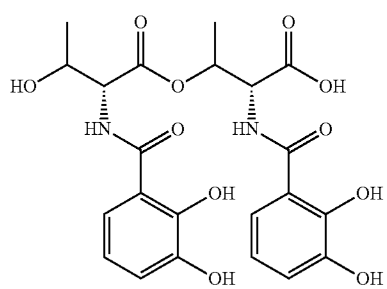 [SMILES: CC(O)[C@@H](NC(=O)c1cccc(O)c1O)C(=O)OC(C)[C@@H](NC(=O)c1cccc(O)c1O)C(=O)O] |
| XL | (2R)-2-(2,3-dihydroxybenzamido)-3-hydroxybutanoic acid<br>Exact Mass: 255.0743 | 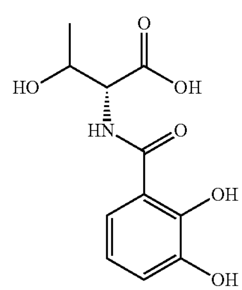 [SMILES: CC(O)[C@@H](NC(=O)c1cccc(O)c1O)C(=O)O] |

No precursor added for XXXVIII-XL

TABLE 2-continued

Nonribosomal molecules

| Formula | Name | Structure |
|---|---|---|
| XLI | N-(3-aminopropyl)-2,3-dihydroxybenzamide<br>Exact Mass: 210.1004 | 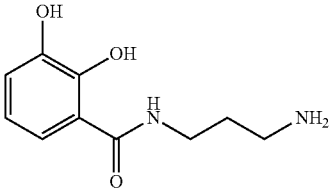 [SMILES: NCCCNC(=O)c1cccc(O)c1O] |
| | Precursor added:<br>1,3-Diaminopropane | 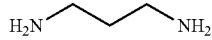 |
| XLII | N-(3-((4-aminobutyl)amino)propyl)-2,3-dihydroxybenzamide<br>Exact Mass: 281.1739 | 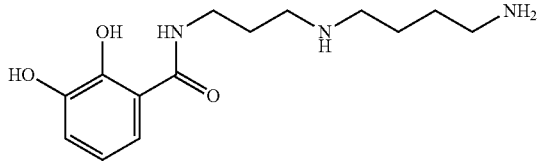 [SMILES: NCCCCNCCCNC(=O)c1cccc(O)c1O] |
| XLIII | (S)-N-(3-((4-(2-(2,3-dihydroxybenzamido)-3-hydroxypropanamido)butyl)amino)propyl)-2,3-dihydroxy-benzamide<br>Exact Mass: 504.2220 | 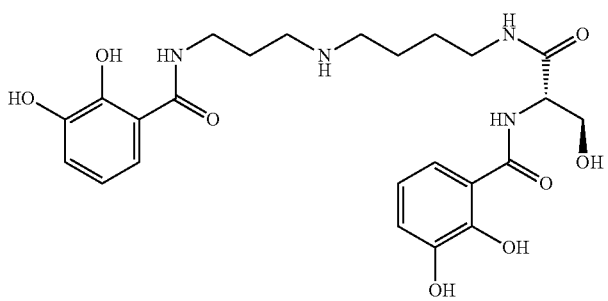 |
| | Precursor added for XLII and XLIII: N-(3-Aminopropyl)-1,4-diaminobutane | 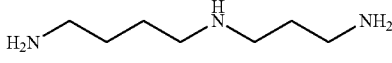 |
| XLIV | (S)-N-(2-((4-((3-(2,3-dihydroxybenzamido)propyl)amino)butyl)amino)ethyl)-2-(2,3-dihydroxyphenyl)-4,5-dihydrooxazole-4-carboxamide<br>Exact Mass: 529.2536 | 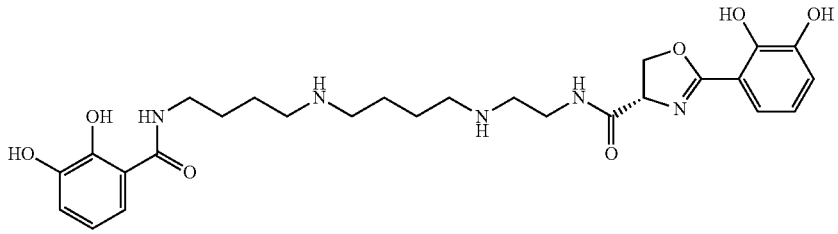 [SMILES: O=C(NCCCCNCCCCNCCNC(=O)[C@@H]1COC(c2cccc(O)c2O)=N1)c1cccc(O)c1O] |
| XLV | (S)-N-(1-(2,3-dihydroxyphenyl)-17-hydroxy-1,15-dioxo-2,6,11,14-tetraazaheptadecan-16-yl)-2,3-dihydroxybenzamide<br>Exact Mass: 547.2642 | 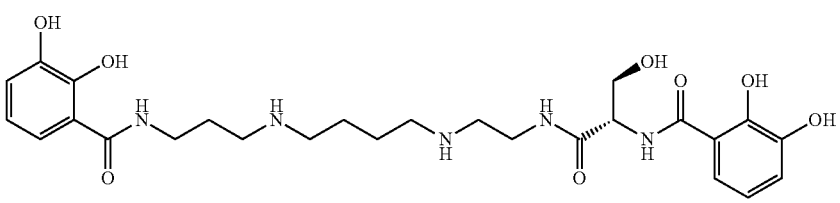 |
| | Precursor added for XLIV and XLV:<br>N,N'-Bis(3-aminopropyl)-1,4-diaminobutane | 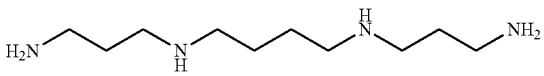 [SMILES: NCCCNCCCCNCCCN] |

TABLE 2-continued

Nonribosomal molecules

| Formula | Name | Structure |
|---|---|---|
| XLVI | N-(5-aminopentyl)-2,3-dihydroxybenzamide<br>Exact Mass: 238.1317 | 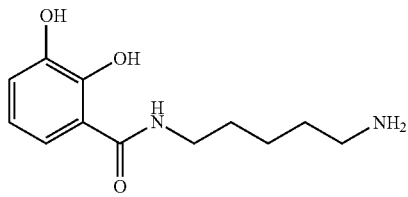 [SMILES: NCCCCCNC(=O)c1cccc(O)c1O] |
| | Precursor added for XLVI: 1,5-Diaminopentane | |
| XLVII | N-(4-aminobutyl)-2,3-dihydroxybenzamide (Aminochelin)<br>Exact Mass: 224.1161 | 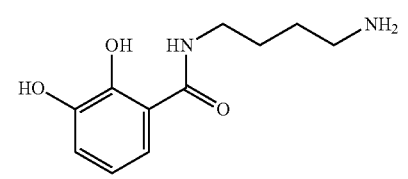 [SMILES: NCCCCNC(=O)c1cccc(O)c1O] |
| | Precursor added for XLVII: 1,4-Butanediamine dihydrochloride | |
| XLVIII | N-(3-((3-aminopropyl)amino)propyl)-2,3-dihydroxybenzamide<br>Exact Mass: 267.1583 | 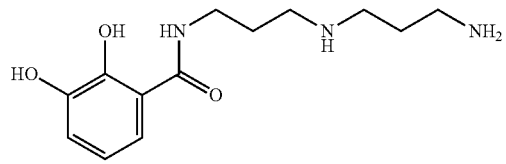 [SMILES: NCCCNCCCNC(=O)c1cccc(O)c1O] |
| | Precursor added for XLVIII: Bis(3-aminopropyl)amine (norspermidine) | |
| XLIX | N-(3-(aminomethyl)benzyl)-2,3-dihydroxybenzamide<br>Exact Mass: 272.1161 | 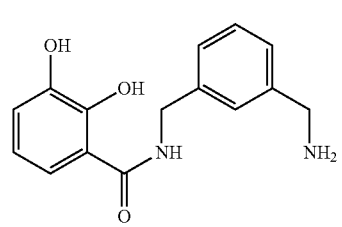 [SMILES: NCc1cccc(CNC(=O)c2cccc(O)c2O)c1] |
| | Precursor added for XLIX: m-Xylylenediamine | |
| L | N-(2-(benzylamino)ethyl)-2,3-dihydroxybenzamide<br>Exact Mass: 286.1317 | 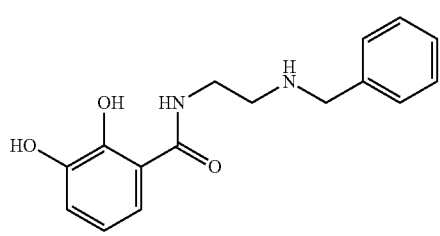 [SMILES: O=C(NCCNCc1ccccc1)c1cccc(O)c1O] |

TABLE 2-continued

Nonribosomal molecules

| Formula | Name | Structure |
|---|---|---|
| LI | (S)-N-benzyl-N-(2-(2,3-dihydroxybenzamido)ethyl)-2-(2,3-dihydroxyphenyl)-4,5-dihydrooxazole-4-carboxamide<br>Exact Mass: 491.1693 | 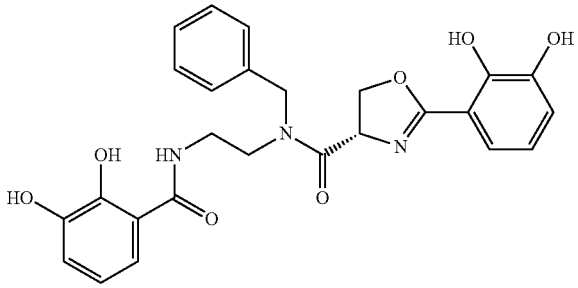 [SMILES: O=C(NCCN(Cc1ccccc1)C(=O)[C@@H]1COC(c2cccc(O)c2O)=N1)c1cccc(O)c1O] |
| | Precursor added for L and LI: N-Benzylethylenediamine | 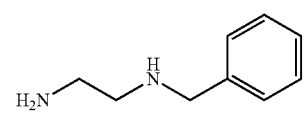 |
| LII | N-(4-(aminomethyl)phenyl)-2,3-dihydroxybenzamide<br>Exact Mass: 258.1004 | 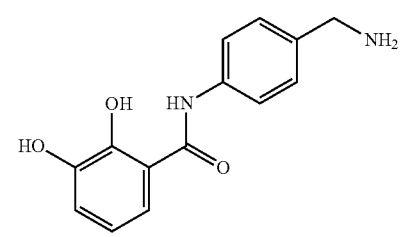 [SMILES: NCc1ccc(NC(=O)c2cccc(O)c2O)cc1] |
| | Precursor added for LII: 4-Aminobenzylamine | 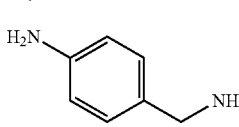 |
| LIII | N-(4-(2-aminoethyl)phenyl)-2,3-dihydroxybenzamide<br>Exact Mass: 272.1161 | 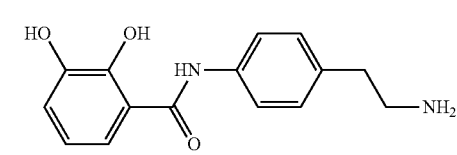 [SMILES: NCCc1ccc(NC(=O)c2cccc(O)c2O)cc1] |
| | Precursor added for LIII: 4-(2-Aminoethyl)aniline | 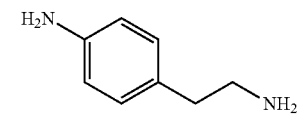 |
| LIV | N-(4-(4-aminophenoxy)phenyl)-2,3-dihydroxybenzamide<br>Exact Mass: 336.1110 | 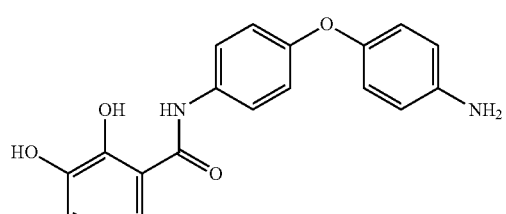 |
| | Precursor added for LIV: 4,4'-Oxydianiline | 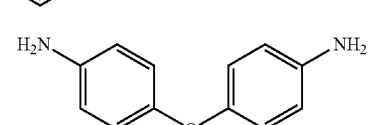 |
| LV | N-(8-aminooctyl)-2,3-dihydroxybenzamide<br>Exact Mass: 280.1787 | 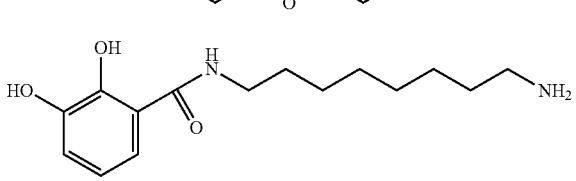 |

TABLE 2-continued

Nonribosomal molecules

| Formula | Name | Structure |
|---|---|---|
| | Precursor added for LV: 1,8-Diaminooctane | 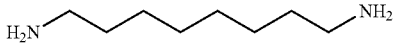 |

Microorganisms display an extraordinary ability to synthesize molecules that can target cancer cells, parasites, iron overload and bacterial infections. For this, they have evolved sets of very large enzymes that harmoniously interact to assemble acyl-CoA or peptide-based molecules, polyketides or nonribosomal peptides, respectively. The genes encoding these enzymes are modular and each module is responsible for the incorporation of one unit.

Tapping this proficiency has nonetheless posed a great challenge to researchers. Besides the difficulties in cultivating some of the producer organisms, it can be also challenging to find the conditions that lead to molecule production, or to engineer the pathway for inducible or constitutive expression. More frequently than not, attempts to alter these pathways for production of new molecules, or even a mere attempt at their heterologous expression, results in a complete shutdown of molecule production.

Provided herein are methods for effective production and structural diversification of nonribosomal molecules, for example. Using these methods, biosynthetic pathways containing ancestral biosynthetic genes were successfully constructed and used in a heterologous and programmable fashion to produce serratiochelins, for example, and their new analog molecules, in demand.

The enterobactin and vibriobactin biosynthetic pathways were constructed to create a single hybrid pathway, comprised of genes involved only in the biosynthesis of each of the molecules. More specifically, entABCDE and vibFH were cloned in a single operon, driven by a lower-expression version of the IPTG-inducible ptrc99a, pDSW204, as discussed below. Expression occurred from an enterobactin-deficient E. coli strain (E. coli Ent) that was generated to lack entABCDEF.

An assortment of structurally diverse nonribosomal peptides were produced by supplementing the iron-deprived growth medium with different small molecule precursors, the substrate of VibH. These molecules were analogs of serratiochelin and its intermediate. Additional structural diversity was generated due to the capacity of VibF to activate not only L-threonine, but L-serine as well, for incorporation into the nascent molecule. In vivo VibF activation of L-serine has never been reported before. Nonetheless, not all precursors could serve as a substrate to VibF or VibH, and even when they could, there seemed to be a slight preference for L-threonine over L-serine activation as well.

The new molecules generated result, in part, from the precursor added to the medium. Thus, the structure of the resulting molecule can be predicted. Nonetheless, if there is a specific moiety that one desires to include in a nascent molecule, the corresponding precursor can be supplied to the medium for incorporation, if it contains at least one amine group. Although, the enzymes active sites can further limit molecule diversity.

Nearly half of the precursors tested herein were incorporated into the nascent molecule and over half of these led to additional new structures, as detected by LC-MS/MS. An algorithm-based analysis of molecular bioactivity on clinically relevant targets also revealed that several of these molecules (particularly the smaller ones) showed promising scores and can potentially be developed into useful drugs.

Besides producing molecules in demand, the synthetic pathways of the present disclosure were used to assembled the cyclic and linear versions of enterobactin, as well as its monomer and its dimer. The synthetic pathways also assembled a new version of linear enterobactin, and its dimer and monomers, containing not L-serine but L-threonine.

Such observation sheds insight onto the evolution of gene collectives, which are thought to be sets of genes that co-evolved quickly to lead to new molecules with the least effort. The following Examples show that the combination of genes from independent pathway can produce new molecules, and known molecules, assembled by different enzymes.

The methods described herein may be expanded to other nonribosomal pathways for which the heterologous expression has posed a problem or when diversification of the structure of the molecules being produced is desired. Using these methods, molecular diversification can be achieved and altered by means of heterologous expression and precursor supplementation, for example.

In silico molecule design and its in vivo assembly may also be implemented using microfluidics systems for consistent, streamlined and on demand production of programmed molecules The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teachings that are referenced herein.

EXAMPLES

Example 1

Figure 1B:
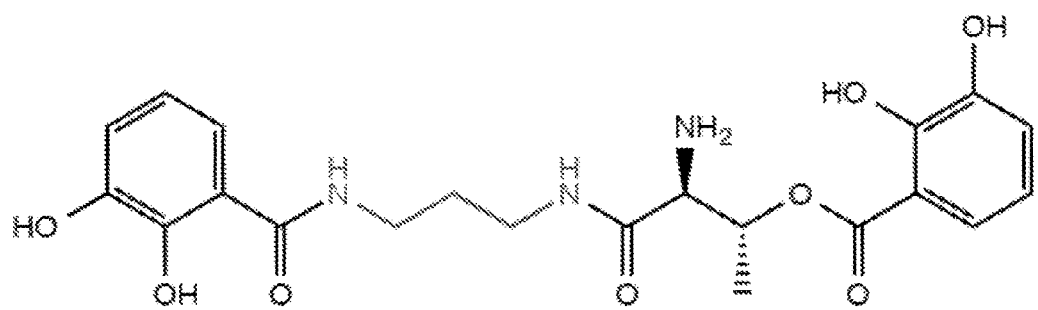
FIG. 1B shows the open-ring chemical structure of serratiochelin.

The present study directed to the production of new molecules based on, but structurally and functionally distinct from, dihydroxybenzoate. This was achieved, ultimately, by providing VibH with different substrates (e.g., polyamine linkers) to condense dihydroxybenzoate (FIG. 1, circled). The polyamine linkers were selected based on the availability of at least two amines groups with one or two hydrogen atoms (see examples in Table 2, "precursors").

Figure 2A:
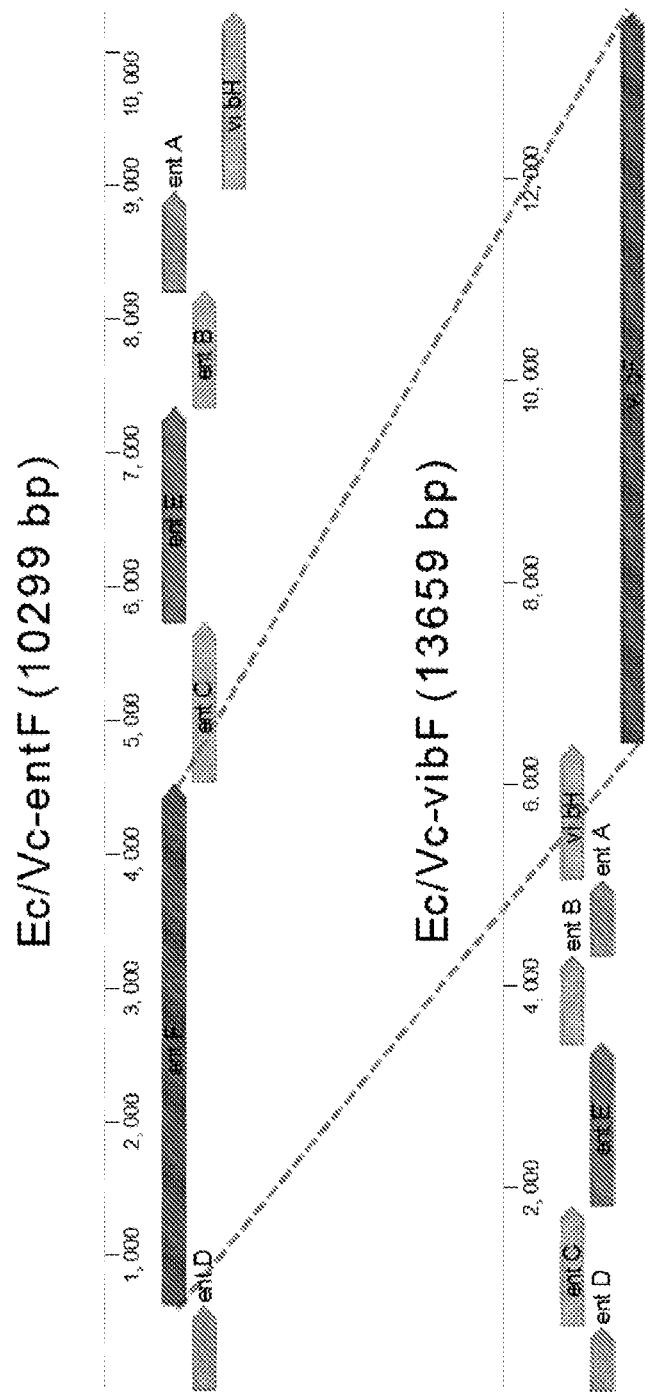
FIG. 2A depicts compressed pathways Ec/Vc-entF (top) and Ec/Vc-vibF (bottom). The Ec/Vc-entF pathway includes the following genes: entD, entF, entC, entE, entB, entA and vibH. The Ec/Vc-vibF pathway includes the following genes: entD, entC, entE, entB, entA, vibH and vibF.
Figure 2B:
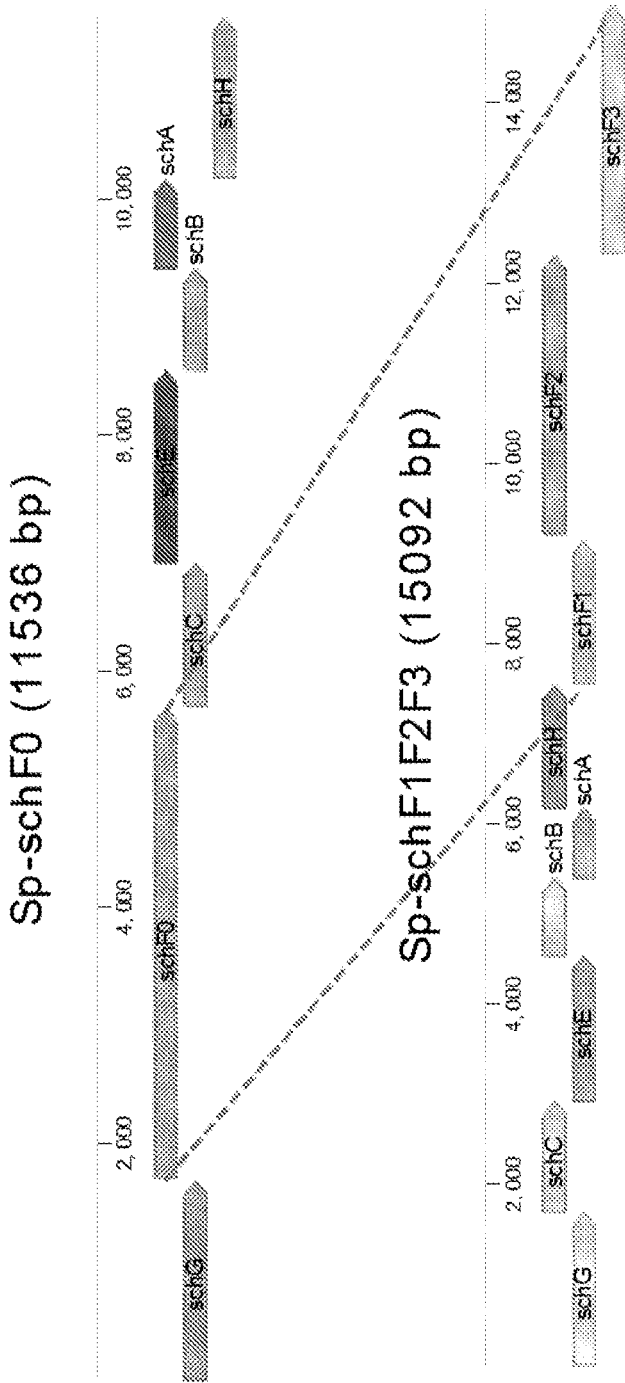
FIG. 2B depicts compressed pathways Sp-schF0 (top) and Sp-schF1F2F3 (bottom). The Sp-schF1F2F3 pathway includes the following genes: schG, schF0, schC, schE, schB, schA and schH. The Sp-schF0 pathway includes the following genes: schG, schC, schE, schB, schA, schH, schF1, schF2, and schF3.

Four different constructs, each containing a "compressed pathway," were prepared for the initial biosynthesis of dihydroxybenzoate (FIGS. 2A-2B). These biosynthetic genes were amplified by PCR using 5'-3' primers that added the E. coli ribosomal binding site GAGGAGA to the region upstream of the translation initiation codon, when required. Genes schCEBA were amplified together having a ribosomal binding site (RBS) been only added upstream of schC. The native RBSs, when existent, were maintained for schEBA (in some cases the genes (e.g., in operons) overlapped (e.g., the 3' of the upstream gene with the 5' of the downstream gene) to promote polycistronic expression).

The first compressed pathway included the following genes: entD, entF, entC, entE, entB, entA and vibH (FIG. 2A, top). The second compressed pathway included the following genes: entC, entD, entE, entB, entA, vibH and vibF (FIG. 2A, bottom). The third compressed pathway included the following genes: schG, schF0, schC, schE, schB, schA and schH (FIG. 2B, top). The fourth compressed pathway included the following genes: schG, schC, schE, schB, schA, schH, schF1, schF2, and schF3 (FIG. 2B, bottom). Serratia plymuthica V4 was the donor for the serratiochelin (sch) genes. Escherichia coli MG1655 was the donor for the enterobactin (ent) genes entCEBA, entD and entF, while Vibrio cholera El Tor A1552 was the donor for the vibriobactin (vib) genes vibF and vibH.

Unexpectedly, the only compressed pathway capable of producing the iron chelating molecules required for survival of the strain in the growth conditions used was the second compressed pathway (FIG. 2A, bottom, and FIG. 3), which contained both vibH and vibF. This pathway was used to generate molecules with structural and functional diversity relative to dihydroxybenzoate.

This compressed pathway was cloned into a medium copy plasmid pDSW204 (E. coli) (FIG. 3). The biosynthetic genes (e.g., entD, entC, entE, entB, entA, vibH and vibF) were cloned into a single operon, using their native or standard E. coli. ribosomal binding site (RBS). The isopropyl 3-D-1-thiogalactopyranoside (IPTG)-inducible trc promoter was used to drive expression of the compressed pathway. Given the size of the compressed pathway, a cos site was cloned in for stability.

E. coli MG1655 was selected as a host, given its robustness. In order to avoid the potential noise created by the enterobactin pathway in the chromosome of E. coli, endogenous genes entD, entF and entCEBA were deleted from its chromosome (via Lambda Red Recombination). entD was replaced with a chloramphenicol-resistance cassette, entCEBA was replaced with kanamycin-resistance cassette, and entF was replaced with gentamicin-resistance cassette. The removal of the enterobactin biosynthetic genes disabled this organism's capacity to assemble this siderophore. The assembly of the genes in a single pathway was assessed in yeast by amplifying by PCR the junctions (e.g., forward primer on one region, reverse primer on the next region). With such method, a correct product size is indicative of proper assembly. Thus, the genes entF, entD, entCEBA, vibF, vibH, schF0, schF1, schF2F3, schH, schG and schCEBA were PCR-amplified with overhangs homologous to the genes located up and downstream in the compressed pathway. The genes at the beginning and end of each pathway were amplified with 5' or 3' primers, respectively, which added a SpeI restriction site and homology to the YAC pYES-1L (Life Technologies). The amplicons were transformed into, and assembled into full pathways, by S. cerevisiae using the Geneart® High Order Genetic Assembly kit (Life Technologies). The compressed pathways were released from pYes-1L by digestion with the restriction enzyme SpeI. The expression vector derived from pDSW205 was digested with the same enzyme, downstream of the trc promoter, and the compressed pathway cloned in.

All strains were maintained on Lysogeny Broth (Miller) medium, supplemented with 15% agar. Seeking to activate all iron uptake native mechanisms, the E. coli MG1655 ΔentBΔentCEBAΔentF carrying the compressed pathway was grown in iron-deprived medium: minimal medium (e.g., 3.0 $K_2HPO_4$, 5.96 $Na_2HPO_4$, 5.0 g/L glucose, 1.0 g/L $NH_4Cl$, 0.5 g/L NaCl, and 0.058 g/L $MgSO_4$, at pH 7.0) supplemented with 1 mM IPTG, 100 µg/L ampicillin and 0.1 mM bipyridyl. The growth medium was supplemented with precursors (also referred to as polyamine linkers) to a final concentration of 0.05 µM to 10 mM. The cells were grown in a 250 mL of medium in a 1 L Erlenmeyer flask, shaking at 250 rpm, for 5 days ($OD_{610\ nm} \approx 0.500$) at 30° C. (surprisingly, the growth rate was slower, and survival poorer, at 37° C.). After incubation for 5 days the cultures were spun-down (5000 rpm, 5 min, 4° C.), the supernatant was filter sterilized, the sterile supernatant was loaded into C18 Reversed-phase Sep-Pac columns, and the molecules of interest were eluted with 100% acetonitrile. The panoply of precursors was selected based on the presence of at least two amine groups having one or two free hydrogen atoms. The precursors were also selected based on their potential to endow the molecule with alternative or additional functionalities.

The various precursors used and molecules (in closed chain form and open chain form) produced are shown in Table 2.

Example 2

Serratiochelins are catechol siderophores produced by Serratia plymuthica V4. These siderophores utilize catechol moieties for iron coordination, obtaining them from the conversion of endogenous chorismate to dihydroxybenzoate (DHB). This pathway appears to be extremely conserved among catechol siderophores. Additional enzymes can then use this precursor to form a wide diversity of catechol-based molecules, such as enterobactin, fluvibactin, vibriobactin, photobactin, petrobactin and vulnibactin.

The experiments described in this example address whether E. coli is capable of producing enterobactin as well as serratiochelins by testing (1) whether the machinery responsible for the import and export of siderophores in E. coli would recognize serratiochelins and its catechol moieties; (2) whether E. coli can uptake polyamines (Table 3), (3) whether S. plymuthica genes would be functional in E. coli (Table 4), and (4) whether expressing the DHB pathway proteins in a different organism and supplementing the media in which the organisms with a desired precursor would result in the generation of new analogs.

TABLE 3

List of precursors, reference number and final working concentration.

| | Polyamine Precursor | Sigma-Aldrich product number | Concentration in medium |
|---|---|---|---|
| 1 | 1,3-Diaminopropane | D23602 | 8 mM |
| 2 | N-(3-Aminopropyl)-1,4-diaminobutane | S0266 | 8 mM |
| 3 | N,N'-Bis(3-aminopropyl)-1,4-diaminobutane | S4264 | 1 mM |
| 4 | 1,5-Diaminopentane | D22606 | 1 mM |
| 5 | 1,4-Butanediamine dihydrochloride | P5780 | 2.5 mM |
| 6 | Bis(3-aminopropyl)amine (norspermidine) | I1006 | 10 mM |

TABLE 3-continued

List of precursors, reference number and final working concentration.

| | | | |
|---|---|---|---|
| 7 | m-Xylylenediamine | X1202 | 2.5 mM |
| 8 | N,N'-Bis(2-aminoethyl)-1,3-propanediamine | 333131 | 5 mM |
| 9 | N-Benzylethylenediamine | 462292 | 2.5 mM |
| 10 | 4-Aminobenzylamine | 368466 | 2.5 mM |
| 11 | 4-(2-Aminoethyl)aniline | 123056 | 0.5 mM |
| 12 | 4,4'-Oxydianiline | 248398 | 0.05 mM |
| 13 | 4,4'-Diaminodiphenylmethane | 32950 | 0.01 mM |
| 14 | 1,5-Diaminonaphthalene | D21200 | 5 mM |
| 15 | 2,2'-Thiobisacetamide | S365033 | 0.02 mM |
| 16 | Sulfaguanidine | S8751 | 2.5 µM |
| 17 | p-Aminobenzenesulfonamide | S9251 | 0.05 µM |
| 18 | Urea | U5378 | 5 mM |
| 19 | N-Phenylthiourea | P7629 | 5 mM |
| 20 | 3,3'-Diamino-N-methyldipropylamine | 188441 | 5 mM |
| 21 | 1,8-Diaminooctane | D22401 | 5 mM |

| | Dipeptides | Company | Concentration in medium |
|---|---|---|---|
| 22 | Dipeptide KR | Biomatik USA | 0.01 mM |
| 23 | Dipeptide KK | | |
| 24 | Dipeptide KQ | | |
| 25 | Dipeptide QN | | |

TABLE 4

Levels of similarity between homologous proteins involved in the assembly of siderophores in E. coli, V. cholerae and S. plymuthica.

| Comparison | Max Score | Total Score | Query Coverage | E value | Identity |
|---|---|---|---|---|---|
| EntA vs. SchA | 431 | 431 | 98% | $7 \times 10^{-159}$ | 72% |
| EntB vs. SchB | 335 | 335 | 99% | $4 \times 10^{-122}$ | 67% |
| EntC vs. SchC | 421 | 421 | 98% | $3 \times 10^{-151}$ | 57% |
| EntE vs. SchE | 781 | 781 | 99% | 0.0 | 70% |
| EntF vs. SchF0 | 1452 | 1452 | 98% | 0.0 | 58% |
| VibF vs. SchF1F2F3 | 899 | 2131 | 96% | 0.0 | 51% |
| EntD vs. SchG | 19.6 | 52.0 | 58% | 0.11 | 24% |
| VibH vs. SchH | 207 | 222 | 95% | $2 \times 10^{-66}$ | 32% |

Figure 4A:
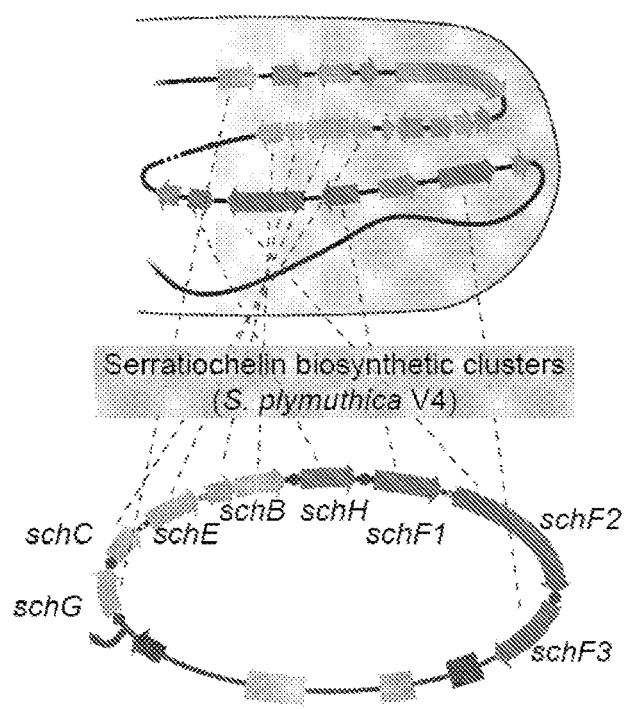
FIGS. 4A-4B show examples of compressed synthetic pathways for heterologous expression of natural and unnatural nonribosomal peptides. Heterologous expression of serratiochelins in *E. coli* Ent-cells was initially attempted by cloning their biosynthetic genes into a single operon, driven by pDSW204 promoter (FIG. 4A). Genes from *E. coli* MG1655 and *V. cholerae* A1552, which are homologous to those involved in the biosynthesis of serratiochelins, were then cloned into a single operon (FIG. 4B). The enzymes responsible for activating an amino acid and incorporating it into the nascent molecule differ slightly in their core motif: VibF DMFVAGLI (SEQ ID NO: 8) Ser/Thr; SchF2 DMFCAGLI (SEQ ID NO: 9) Ser/Thr; EntF DVWHFSLV (SEQ ID NO: 10) Ser; and MbtB DMLNAGLV (SEQ ID NO: 11) Ser/Thr. Based on its core motif, VibF, similar to serratiochelin SchF2 and mycobactin MbtB, should activate L-serine and L-threonine.

The precursor 1,3-diaminopropane (diaminopropane) is required for the assembly of serratiochelins and is naturally produced by S. plymuthica but not by E. coli. In order to produce serratiochelins using E. coli, diaminopropane was added to the growth medium. The S. plymuthica genes involved in the biosynthesis of serratiochelins were cloned in a single operon and were driven by an inducible promoter pDSW204 (pSP_S), a weaker version of ptrc99A. This synthetic operon is a compressed version of the 2-cluster pathway responsible for biosynthesizing serratiochelins (FIG. 4A). It contains only (1) genes schABCEG, which are homologous to the genes entABCDE involved in the biosynthesis of enterobactin, (2) genes schF1F2F3, which together are homologous to vibF, and (3) schH, a vibH homolog. Genes vibF and vibH are involved in the biosynthesis of vibriobactin, a siderophore obtained from V. cholerae.

The constructs were transformed into a strain of E. coli Ent from which genes entABCDEF (homologous to schAB-CEG) had been removed. The E. coli strain Ent, carrying either pSP_S or empty vector, were grown in the presence or absence of diaminopropane under iron-deprived conditions at 30° C. with agitation. Growth was not observed in either case. Without being bound by theory, the lack of growth may reflect the incapacity of the E. coli transcriptional and translational machinery to operate on S. plymuthica genes, or the resulting enzymes might not have found in E. coli conditions favorable to their activation and processing. The enzymes responsible for assembling nonribosomal peptides function as assembly lines. This suggests that if one single enzyme is not present or is non-functional, the target molecule might not be made.

Example 3

As noted above, the biosynthetic pathway in Example 1 includes genes homologous to E. coli and V. cholerae genes. In E. coli and V. cholerae, these homologs form part of the biosynthetic pathways that produce enterobactin and vibriobactin, respectively. The following experiments tested whether these genes could replace the S. plymuthica homologs to produce serratiochelins. Thus, an additional pathway was constructed for the biosynthesis of serratiochelins and new analogs.

Figure 4B:
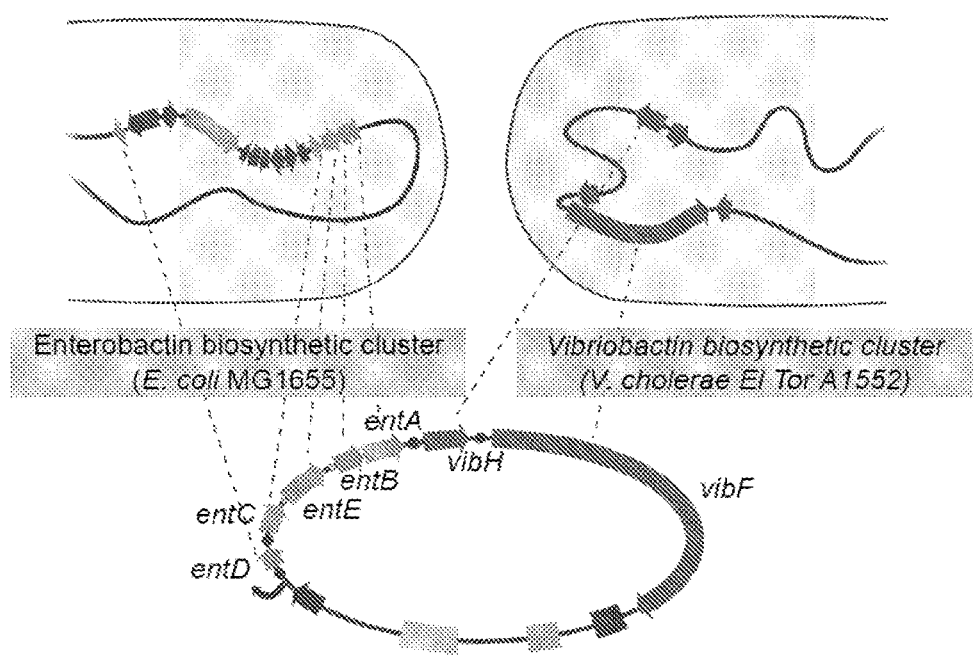

E. coli genes entABCDE and V. cholerae gene vibFH, ancestral homologs to S. plymuthica V4 genes, were cloned into the same empty plasmid backbone, the plasmid was introduced into E. coli Ent, and the resulting construct was designated pEV_S (FIG. 4B, bottom). Holo-EntB, acylated with DHB by EntE, serves as a substrate for the activity of VibH, similarly to VibB. pEV_S enabled the growth of E. coli Ent-under iron-limited conditions in the presence of diaminopropane. The production of both a serratiochelin precursor (FIG. 5, M1) and serratiochelin (FIG. 6, M1) was confirmed upon analysis of the tC18-purified supernatant.

Figure 7A:
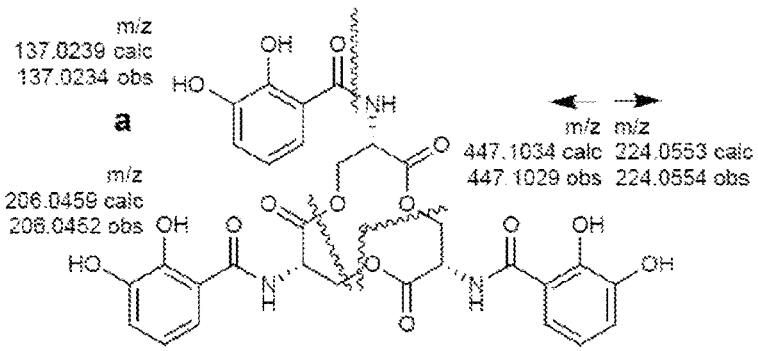
FIGS. 7A-7D show the calculated and observed mass (left) and structure and observed versus calculated fragmentation pattern (right) of indicated molecules produced using the methods of the present disclosure.
Figure 7B:
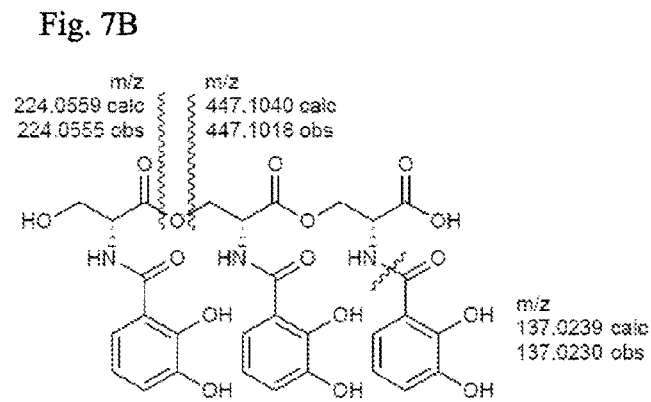
Figure 7C:
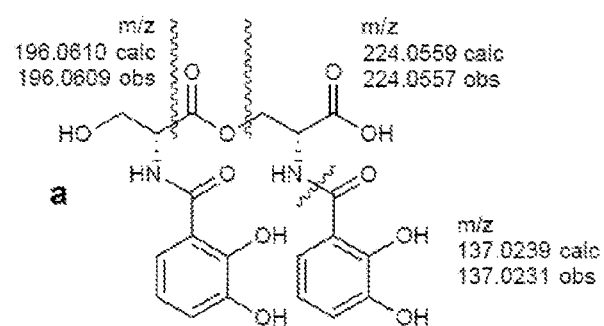
Figure 7D:
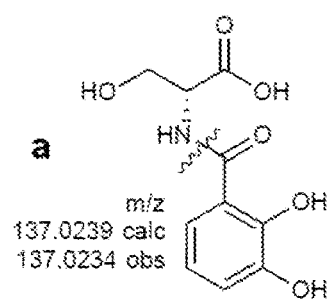

Unexpectedly, growth for E. coli Ent carrying pEV_S was also observed in the absence of diaminopropane, indicating that another siderophore, independent of the polyamine, could be assembled by enzymes encoded by the biosynthetic pathway. This unexpected observation was investigated, and upon analysis of the tC18-purified supernatant, the production of enterobactin was detected (FIG. 7A) as well as linear enterobactin (FIG. 7B) and its dimers (FIG. 7C) and monomers (FIG. 7D). These results shows that VibF can replace EntF to assemble this enterobactin, independent of any precursors. Enterobactin was detected in all samples analyzed, except those to which norspermidine or sulfaguanidine had been added. Linear enterobactin and its dimers and monomers were also found in most samples. E. coli Ent-, which is the empty strain, could not grow under the same conditions.

Figure 8A:
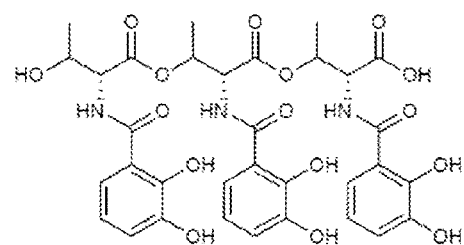
FIGS. 8A-8C show the calculated and observed mass (left) and structure and fragmentation pattern (right) of indicated molecules produced using the methods of the present disclosure.
Figure 8B:
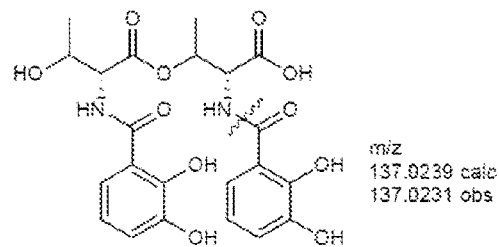
Figure 8C:
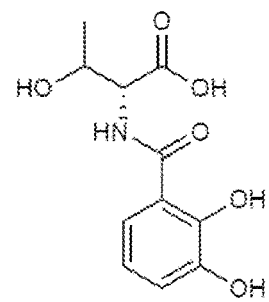

Based on the results above, experiments were designed to investigate whether this pathway could produce thr-enterobactin analogs. Only linear thr-enterobactin (FIG. 8A), its dimers (FIG. 8B) and monomers (FIG. 8C) were detected, and only in a reduced number of samples. These results, however, do not exclude the possibility that thr-enterobactin was produced at levels too low to be detected.

This study demonstrates in vivo VibF activation of L-serine to produce enterobactin, and L-threonine activation to produce a new linear thr-enterobactin. The alternative pathway to enterobactin removed the selective pressure exerted on the compressed pathway to condense polyamines and generate serratiochelin analogs.

Example 4

Having established a hybrid pathway capable of producing molecules, as a function of the precursor added, experiments were then designed to determine the extent of the hybrid pathway's programming capabilities. Polyamines with a varying number of carbons and amine groups, with and without other moieties, as well as 4 dipeptides, were added to the growth medium (see Table 3). The concentration used was determined as the highest concentration that would not inhibit the growth of the producer strain, in the absence of iron.

Figure 5:
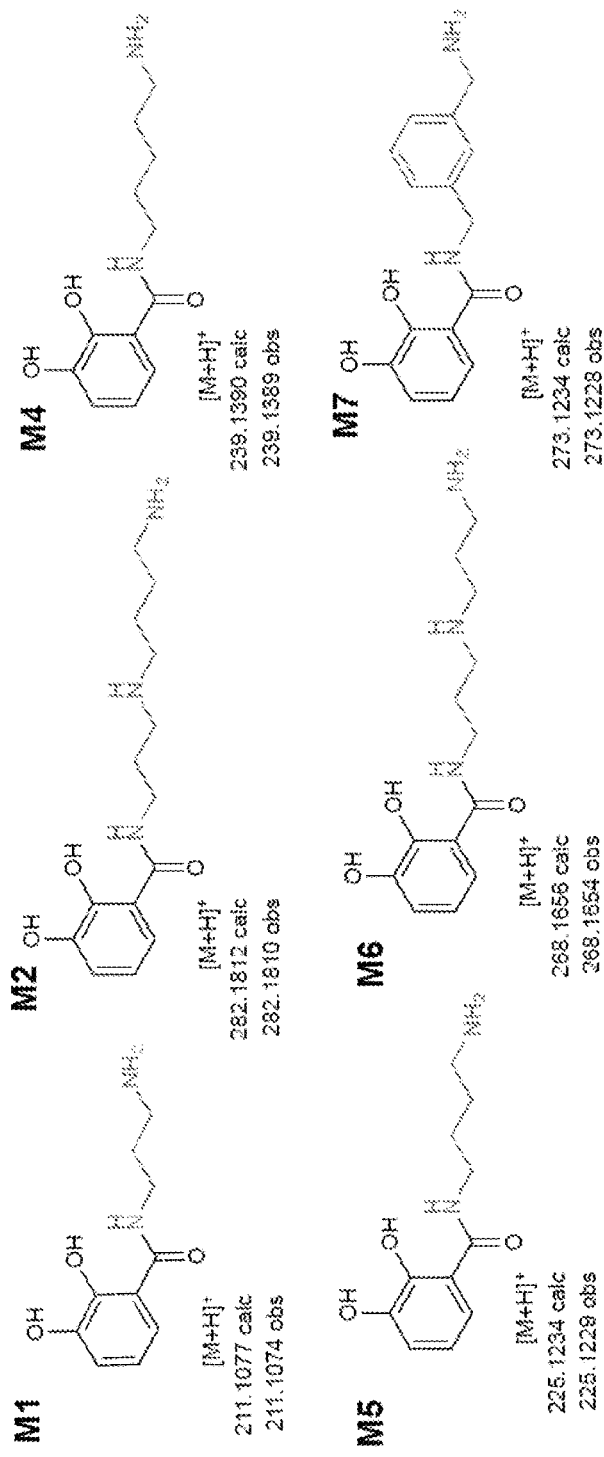
FIG. 5 shows structures for the DHB-polyamine intermediates assembled by the compressed pathway. By adding other polyamines to the growth medium, VibH was found to catalyze the reaction between foreign free polyamines and the tethered DHB. Each molecule is identified by the letter "M" and a number, corresponding to the polyamine added to the medium.
Figure 5:
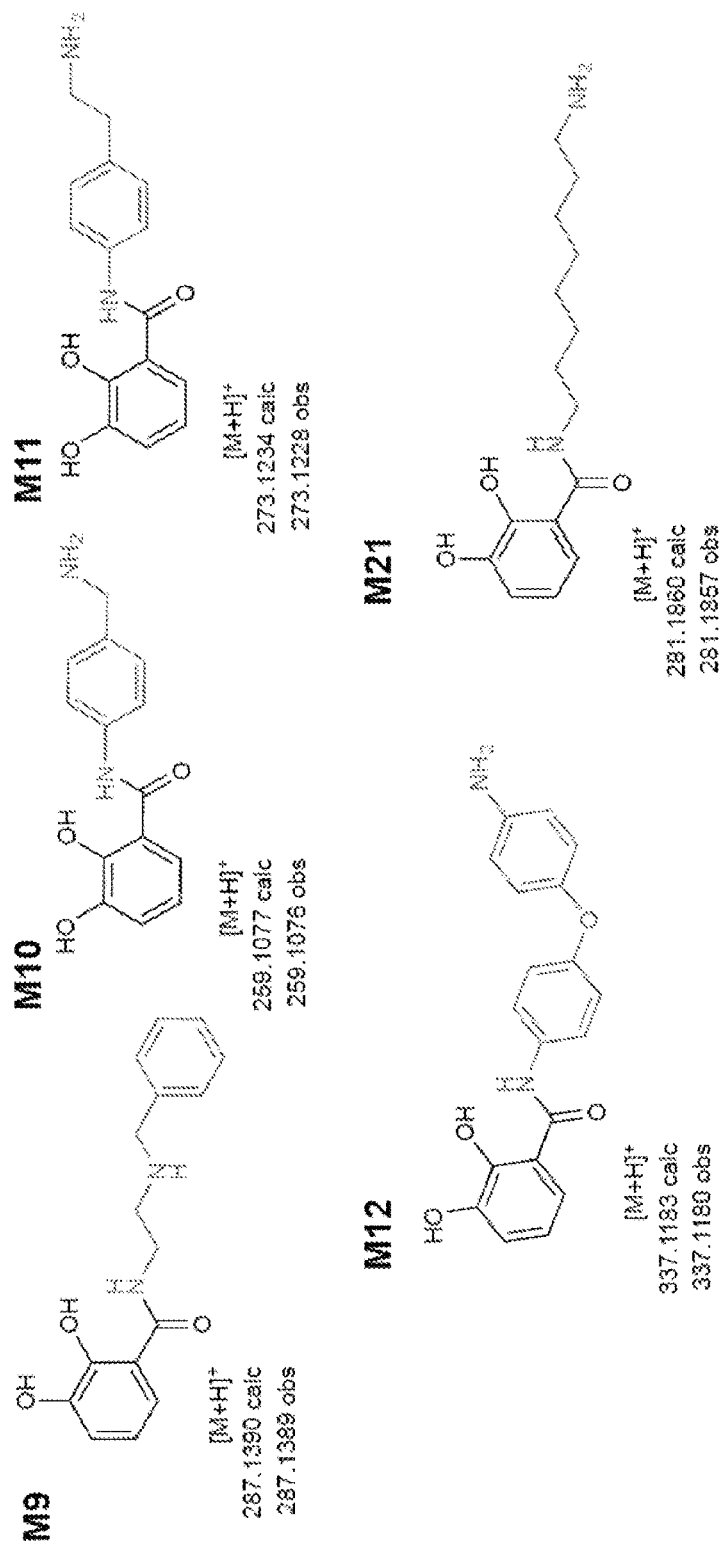
Figure 9A:
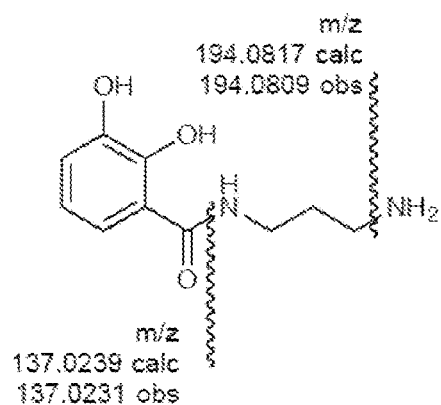
FIGS. 9A-9W show the calculated and observed mass (left) and structure and fragmentation pattern (right) of indicated molecules produced using the methods of the present disclosure. So: serine incorporation, open configuration; Sc: serine incorporation, closed configuration; To: threonine incorporation, open configuration; Tc: threonine incorporation, closed configuration.
Figure 9B:
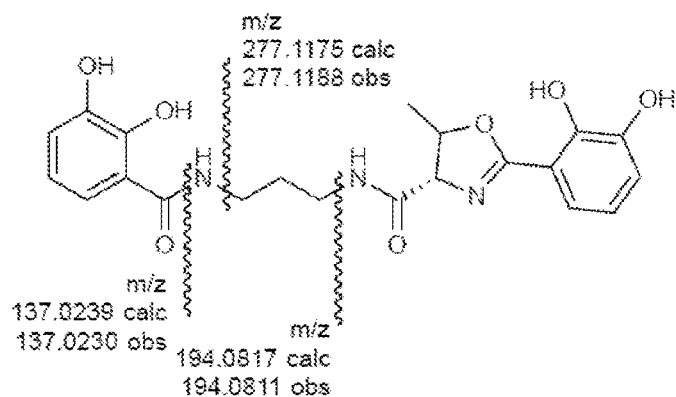
Figure 9C:
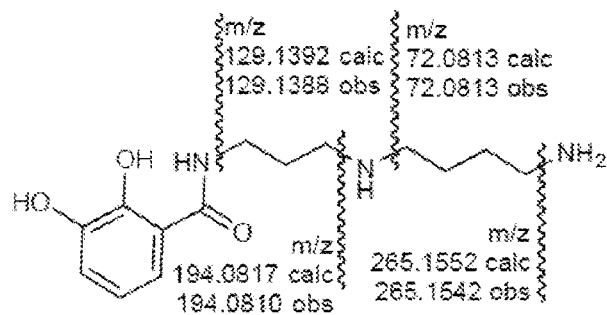
Figure 9D:
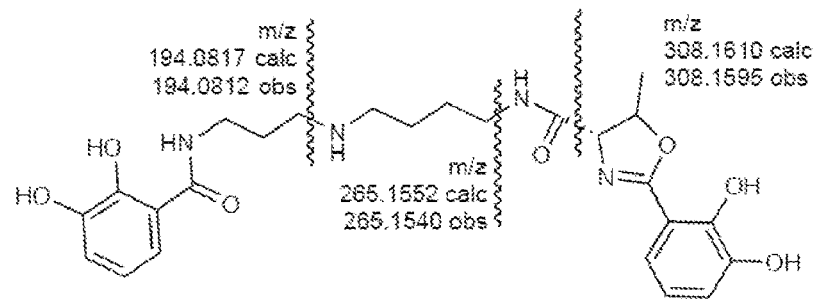
Figure 9E:
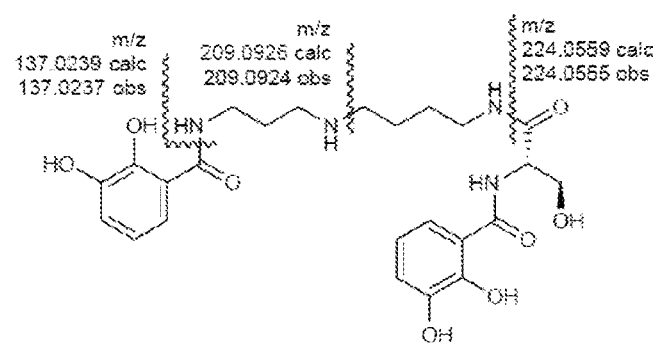
Figure 9F:
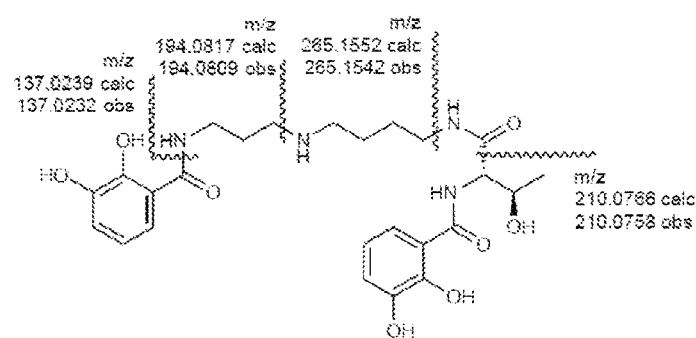
Figure 9G:
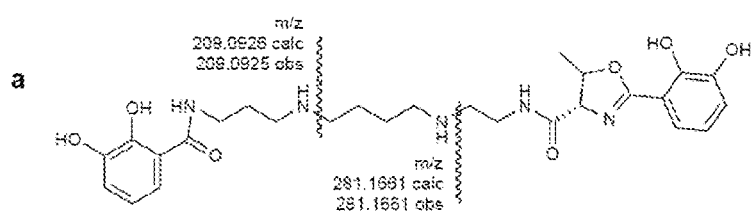
Figure 9H:
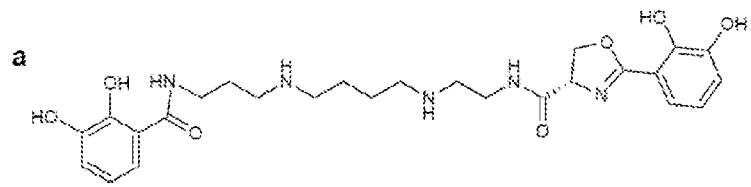
Figure 9I:
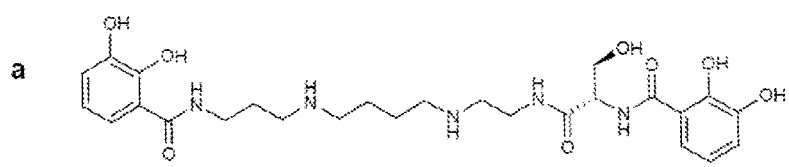
Figure 9J:
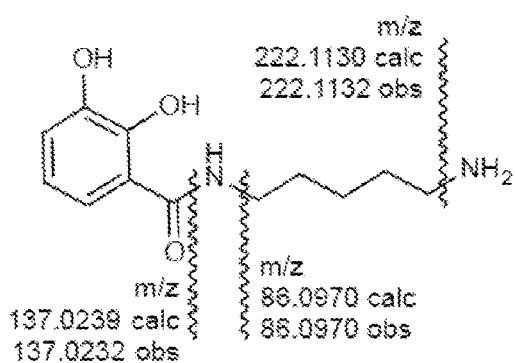
Figure 9K:
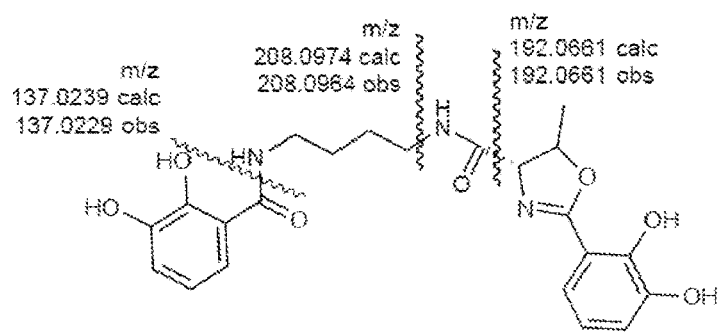
Figure 9L:
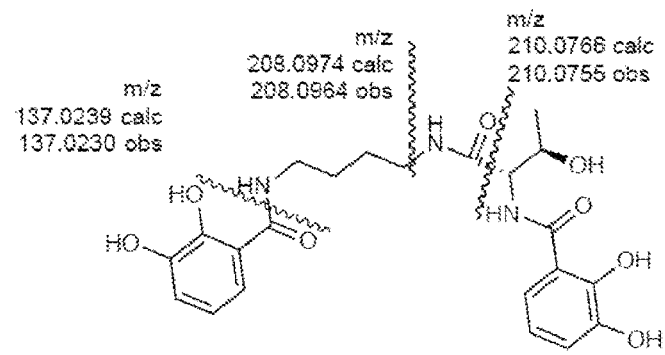
Figure 9M:
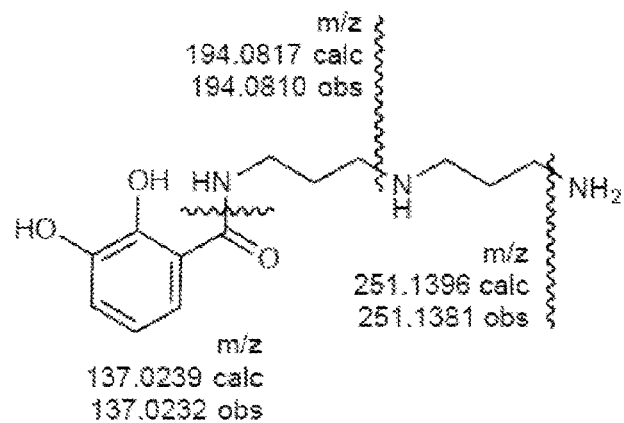
Figure 9N:
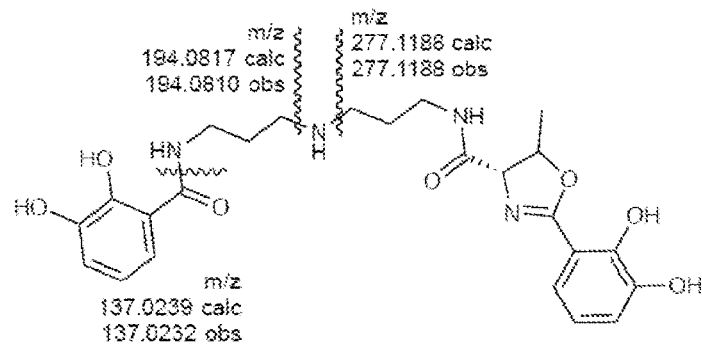
Figure 9O:
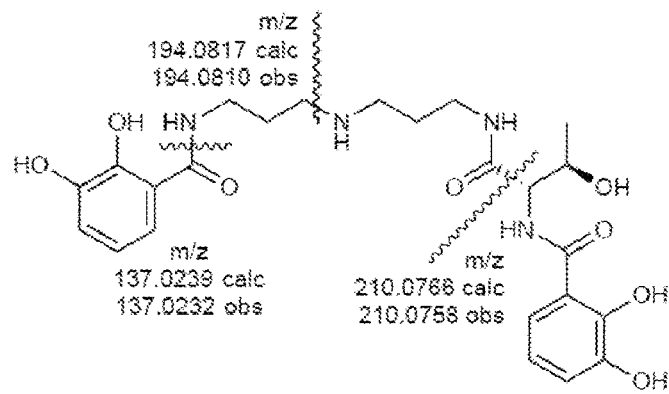
Figure 9P:
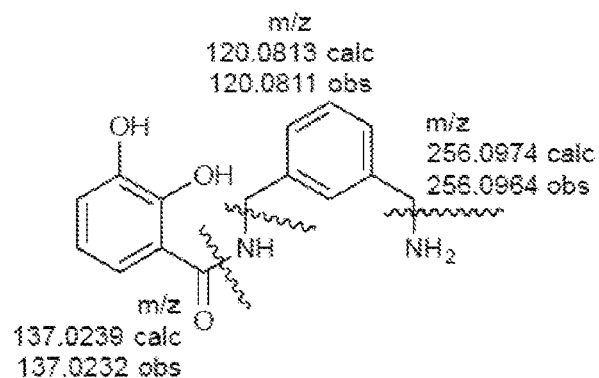
Figure 9Q:
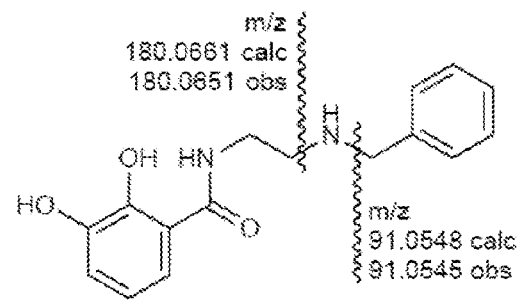
Figure 9R:
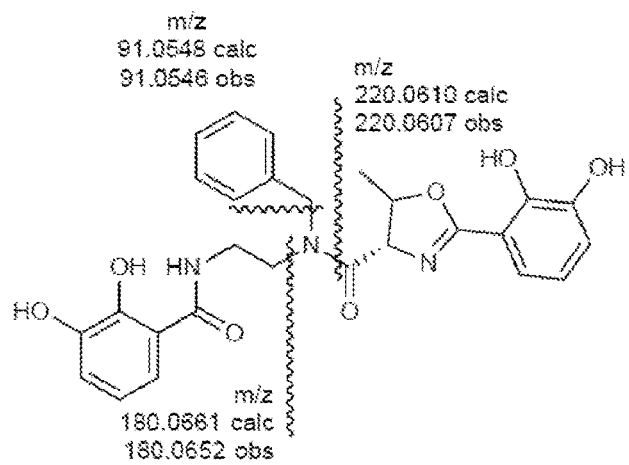
Figure 9S:
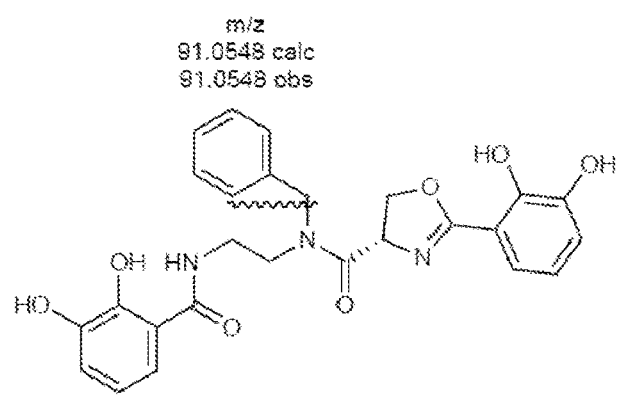
Figure 9T:
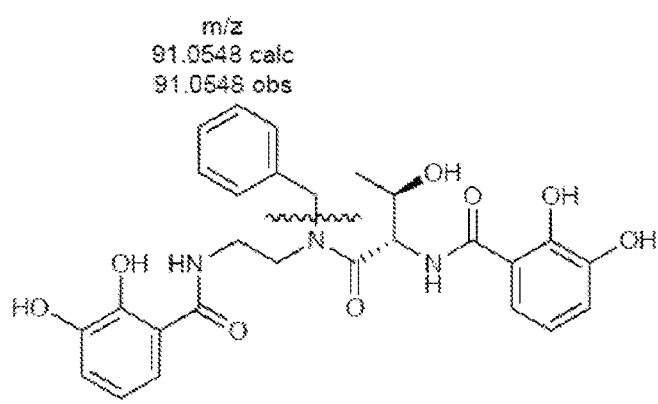
Figure 9U:
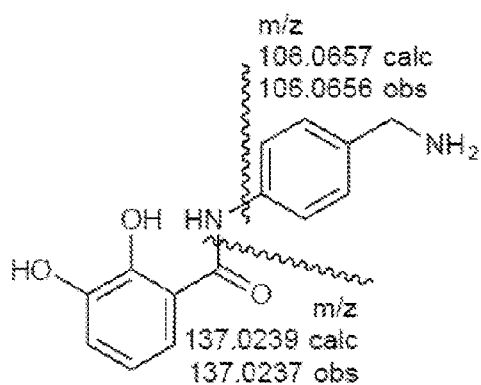
Figure 9V:
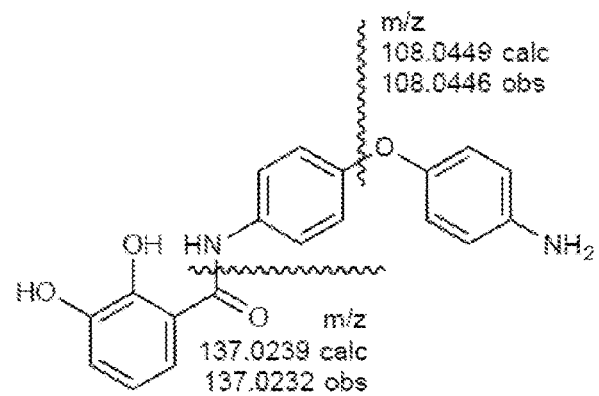
Figure 9W:
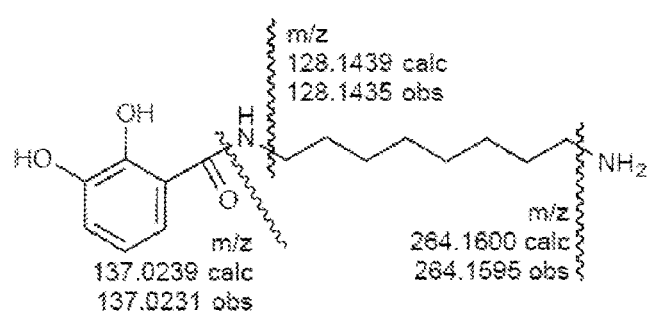

The biosynthetic and programmable pathway was capable of generating, on demand, several of the predicted intermediate nonribosomal peptides, where a polyamine was condensed with DHB (FIG. 5). VibH condense linear polyamines as well as aromatic polyamines, such as aminobenzylamine (FIG. 5, M10 and FIG. 9U) and oxydianiline (FIG. 5, M21 and FIG. 9W). The annotated MS/MS spectra for the structures shown in FIG. 9 were also obtained.

Figure 6:
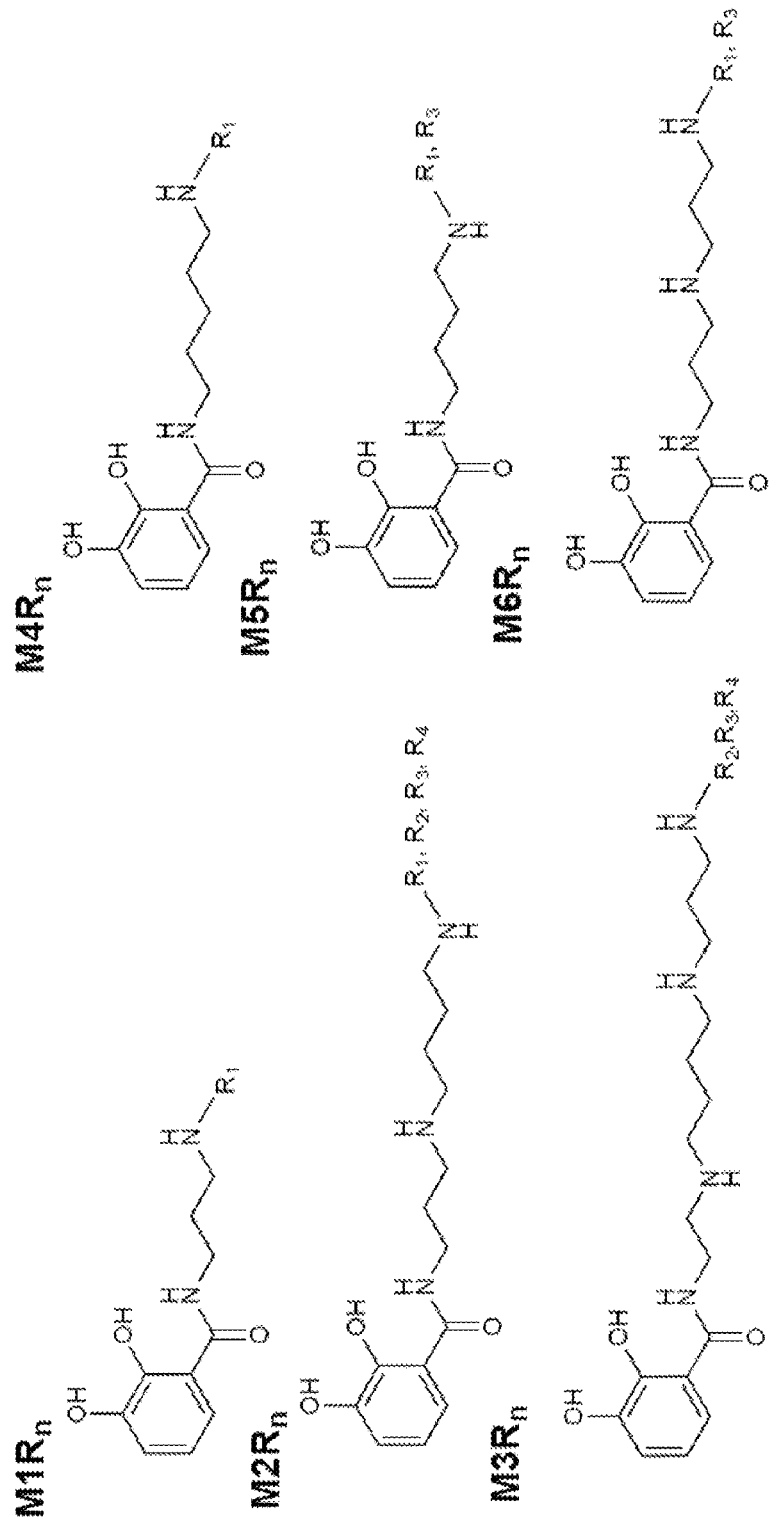
FIG. 6 shows structures for new serratiochelin analogs. The acylation of the remaining primary amine by VibF occurs with a 2-(2,3-dihydroxyphenyl)-5-methyloxazolinyl and a 2-(2,3-dihydroxyphenyl)-oxazolinyl. In some samples, the amino acid incorporated in the intermediate did not go through an additional cyclization, thus remaining in the open conformation as dihydroxybenzoyl-L-threonine and as dihydroxybenzoyl-L-serine. The second acylation of a primary amine occurred only for the intermediates depicted with up to four alternative radicals. Each molecule is identified by the letter "M" and a number, corresponding to the polyamine number, as well as the amino acid incorporated and its conformation. $R_n$ indicates the alternative radicals for the structures proposed and detected in the samples.
Figure 6:
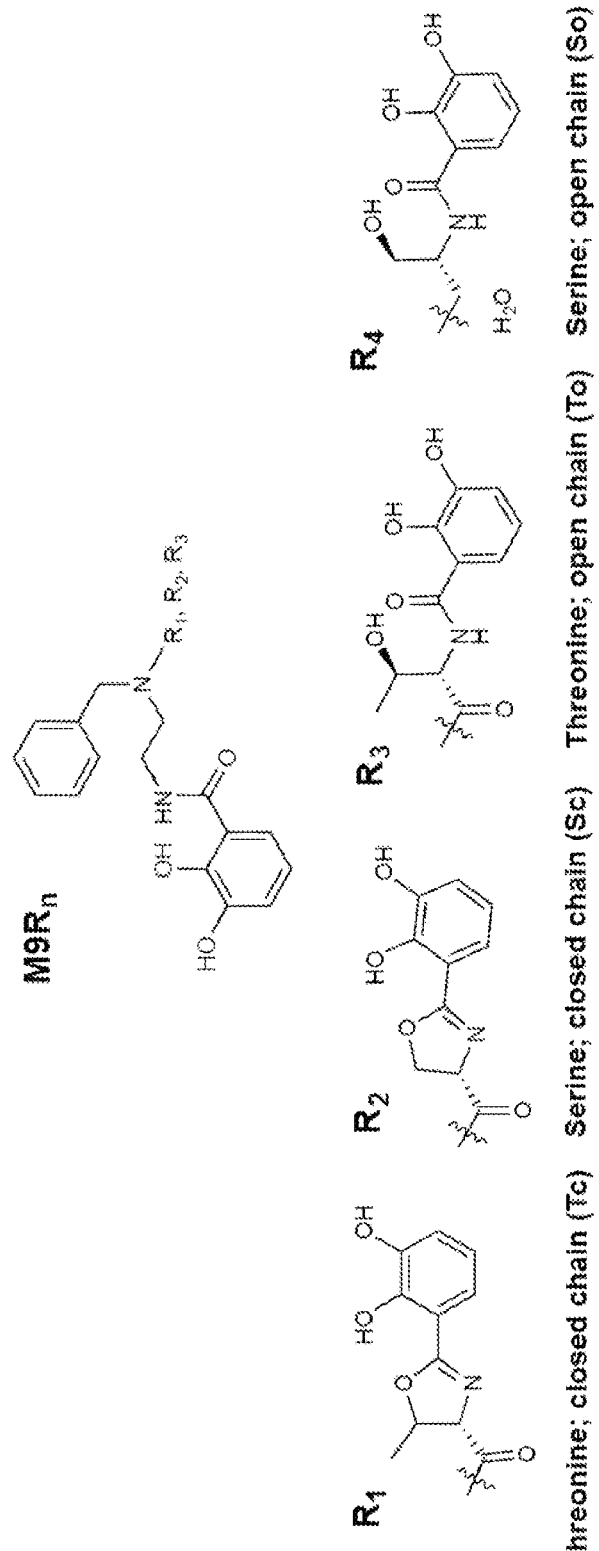

The capacity of the pathway to generate fully-assembled serratiochelin mutasynthons seemed to be mostly restricted to linear polyamines, containing up to 4 amine groups and 10 carbons (Table 3, polyamine 3, FIG. 6, M3R$_n$). Nonetheless, VibF incorporated L-serine or L-threonine in the molecules and, for some molecules, depending on the precursor supplemented, cyclized the molecule (see FIGS. 9A-9W). VibH was flexible in the substrate it can act upon, transferring the activated DHB from EntB to a diversity of acceptors amines (FIG. 5 and FIGS. 9A-9W).

While vibriobactin was not assembled in the presence of norspermidine in the medium (Table 3, polyamine 6), its intermediate with only the primary amines acylated (FIG. 9N, M6Tc) and an additional analog (FIG. 9O, M6To) was detected.

A factor limiting the diversity of molecules generated appeared to be VibF. Given that several of the intermediates were detected in the supernatant, VibF seems incapable of condensing dihydroxyphenyl-5-methoxyxazoline (and L-serine-containing derivative) with the polyamine-containing intermediate. Several approaches could potentially extend the performance of this synthetic pathway in terms of assembly full-sized molecules. For example, VibF may be subjected to directed evolution and other VibF/SchF1F2F3 homologs tested. It is also possible that the molecules were indeed assembled but could not be exported to the external milieu.

Results also showed a preferential orientation for condensing asymmetrical polyamines using the entB-tethered DHB. For molecules M9 (FIG. 5 and FIG. 9Q), M3Sc (FIG. 9G), M3To (FIG. 9H), M3So (FIG. 9I) and M9Tc (FIG. 9R), a single fragmentation pattern, corresponding to that of a single orientation, was found. Nonetheless, the alternative conformation could exist at lowers levels.

M5 corresponds to aminochelin (FIG. 5), a molecule that can act as a siderophore and can be incorporated into azotochelin, both produced by *Azotobacter vinelandii*. Thus, novel intermediated generated via this programmable pathway may possess metal chelating abilities similar to their larger counterparts.

To investigate whether the engineered non-natural siderophores could serve other therapeutically-relevant purposes, the Simplified Molecular-Input Line-Entry System (SMILES) specifications were run using three online tools that compute the likelihood of the submitted structure having particular activities of biological interest. The SMILES of the new molecules assembled on demand by the programmable pathway provided herein were run using these algorithms, and the scores were compiled in Table 5. Bioactivity prediction was calculated using the web-based platform Molinspiration. Target prediction was calculated with the Swiss Target Prediction web-based tool. Drug-likeness was calculated using MolSoft, a web-based algorithm.

TABLE 5

Algorithm-based bioactivity, ligand target and drug-likeness prediction.

| | Bioactivity | | | | | | | |
|---|---|---|---|---|---|---|---|---|
| M | GPRC ligand (0 < S < 0.80) | Ion channel modulator (0 < S < 1.00) | Kinase inhibitor (0.10 < S < 1.25) | Nuclear receptor ligand (0 < S < 1.25) | Protease inhibitor (0.25 < S < 1.25) | Enzyme inhibitor (0.25 < S < 1.25) | Target 2D | Drug Likeness |
| 1 | −0.08 | 0.23 | −0.18 | −0.72 | −0.21 | 0.05 | Catechol O-methyltransferase (0.86) | 1.23 |
| 2 | 0.28 | 0.30 | 0.19 | −0.23 | 0.18 | 0.22 | Melanin-concentrating hormone receptor 1 (0.77) | 1.54 |
| 4 | 0.08 | 0.26 | −0.03 | −0.41 | 0.00 | 0.16 | Muscleblind-like protein 1 (0.75) | 1.15 |
| 5 | 0.00 | 0.25 | −0.10 | −0.53 | −0.10 | 0.11 | Muscleblind-like protein 1 (0.77) | 1.15 |
| 6 | 0.22 | 0.31 | 0.15 | −0.3 | 0.12 | 0.20 | Catechol O-methyltransferase (0.86) | 1.63 |
| 7 | 0.07 | 0.13 | 0.07 | −0.34 | 0.15 | 0.14 | 22 kDa interstitial collagenase (0.75) | 1.34 |
| 9 | 0.07 | 0.07 | 0.02 | −0.18 | −0.02 | 0.05 | D(2) dopamine receptor (0.80) | 1.63 |
| 10 | −0.05 | 0.02 | 0.07 | −0.52 | −0.02 | 0.06 | Telomerase reverse transcriptase (0.89) | 1.31 |
| 11 | 0.09 | 0.05 | 0.13 | −0.31 | −0.02 | 0.08 | Arachidonate 5-lipoxygenase (0.80) | 1.24 |
| 12 | 0.04 | −0.01 | 0.20 | −0.06 | 0.07 | 0.08 | Microtubule-associated protein tau (0.82) | 1.26 |
| 21 | 0.21 | 0.23 | 0.12 | −0.19 | 0.16 | 0.20 | Melanin-concentrating hormone receptor 1 (0.77) | 1.15 |

TABLE 5-continued

Algorithm-based bioactivity, ligand target and drug-likeness prediction.

| | Bioactivity | | | | | | | |
|---|---|---|---|---|---|---|---|---|
| M | GPRC ligand (0 < S < 0.80) | Ion channel modulator (0 < S < 1.00) | Kinase inhibitor (0.10 < S < 1.25) | Nuclear receptor ligand (0 < S < 1.25) | Protease inhibitor (0.25 < S < 1.25) | Enzyme inhibitor (0.25 < S < 1.25) | Target 2D | Drug Likeness |
| 1Tc | 0.23 | −0.12 | −0.19 | −0.23 | 0.15 | 0.15 | D(2) dopamine receptor (0.59) | 1.09 |
| 2Tc | 0.25 | −0.09 | −0.13 | −0.19 | 0.17 | 0.15 | D(2) dopamine receptor (0.59) | 1.39 |
| 2To | 0.21 | −0.03 | −0.05 | −0.05 | 0.27 | 0.10 | Dipeptidyl peptidase 4 membrane form (0.68) | 0.83 |
| 2So | 0.25 | 0.10 | 0.04 | −0.11 | 0.28 | 0.15 | D(2) dopamine receptor (0.63) | 0.78 |
| 3Tc | 0.24 | −0.20 | −0.14 | −0.21 | 0.16 | 0.11 | (Not significant) | 1.39 |
| 3Sc | 0.27 | −0.15 | −0.16 | −0.20 | 0.16 | 0.20 | D(2) dopamine receptor (0.57) | 1.43 |
| 3So | 0.22 | −0.11 | −0.03 | −0.16 | 0.25 | 0.06 | DDOST 48 kDa subunit (0.66) | 0.78 |
| 5Tc | 0.23 | −0.11 | −0.19 | −0.19 | 0.16 | 0.15 | D(2) dopamine receptor (0.60) | 1.01 |
| 5To | 0.18 | −0.01 | −0.09 | −0.04 | 0.27 | 0.10 | Caspase-1 subunit p20 (0.71) | 0.50 |
| 6Tc | 0.24 | −0.08 | −0.14 | −0.20 | 0.16 | 0.15 | D(2)dopamine receptor (0.59) | 1.47 |
| 6To | 0.20 | 0.00 | −0.05 | −0.06 | 0.26 | 0.10 | K$^+$ voltage-gated channel (0.63) | 0.93 |
| 9Tc | 0.22 | −0.18 | −0.12 | −0.19 | 0.14 | 0.12 | D(2)dopamine receptor (0.61) | 1.58 |
| 9Sc | 0.27 | −0.08 | −0.13 | −0.19 | 0.15 | 0.23 | D(2)dopamine receptor (0.59) | 1.61 |
| 9To | 0.19 | −0.13 | −0.04 | −0.07 | 0.24 | 0.06 | µ-type opioid receptor (0.72) | 0.90 |

Three of the 21 intermediate, and all but three full-sized molecules, were predicted to bind GPRCs (Score>0.20) (Table 5). GPRCs are the largest class of Eukaryotic cell-surface receptors involved over 30 human diseases, such as retinitis pigmentosa and nephrogenic diabetes insipidus. More than 60% of all prescribed drugs target these receptors. The molecules with a score over the threshold were those that contained linear polyamines.

Six intermediates containing linear polyamines (Table 5, M1-6, M21), but none of the full molecules, were predicted to target ion channel modulators. These modulators are membrane proteins that control de passage of ions (e.g., $Ca^{2+}$, $K^+$, $H^+$ and $Cl^-$) across the cell membrane. They are involved in the treatment of multiple human diseases, such as epilepsy, coronary heart disease and chronic pain.

A single molecule (Table 5, M12) was predicted to inhibit kinases. These enzymes phosphorylate proteins altering their activity and are important to restore aberrant phosphorylation associated with disease.

Seven full-sized molecules (Table 5, M2Tc, M2So, M3To, M3So, M5Sc, M6To and M9To) were predicted to inhibit proteases, a feature typical of anti-viral molecules, such as antiretrovirals.

A total of seven molecules were predicted to act as enzyme inhibitors (Table 5, M2, M6, M21, M1Sc, M2Sc, M3Sc and M9Sc), such as anti-cancer molecules that inhibit telomerases.

The Swiss Target Prediction algorithm returns instead a target and the associated 2D fingerprint-based similarity score, for each molecule submitted. 2D-based similarity is based on structural similarity of fragments of the molecules. The SMILES of several molecules submitted returned similar hits, though with different scores as shown on Table 5. Those with the highest score were predicted to target the catechol O-methyltransferase (Table 5, M1, M6, S=0.86). This enzyme degrades catecholamines and its impaired activity is connected to psychiatric disorders. Other molecules were determined to potentially target: telomerase reverse transcriptase (Table 5, M10, S=0.89), which is responsible for telomere maintenance and genome stability; microtubule-associated tau protein (Table 5, M12, S=0.82), which stabilizes microtubules and is thought to be associated with neurodegenerative diseases; arachidonate 5-lipoxygenase (Table 5, M11, S=0.80), whose polymorphism is thought to be connected with Alzheimer's disease; D(2) dopamine receptor (Table 5, M9, S=0.80), associated with addiction; melanin-concentrating hormone receptor 1 (Table 5, M2, M21, S=0.77), associated with obesity; muscle blind-like protein 1 (Table 5, M5, S=0.77; M4, S=0.75), involved in mRNA maturation in mammals and associated with myotonic dystrophy; and opioid receptors (Table 5, M9Tc, S=0.72), involved in addiction. Despite sharing some of these predicted targets, all full-sized molecules had lower scores than their smaller counterparts (S<70), though their values are still significant (S>0.5).

The overall non target-specific drug-likeness of each molecule (Table 5), was significant for all structures (S>0), varying between 0.50 (Table 5, M5Sc) and 1.63 (Table 5, M6 and M9). These results highlight the potential clinical relevance of the molecules generated.

The Lipinski Rule of Five aims to be a straightforward method for prediction of the solubility, absorption and permeation of any molecule, in the human body (Lipinski C A et al. *Adv. Drug Deliv. Rev.* 64, 4-17, 2012). At most, 10% of the drugs in the dataset did not respect these rules, when combined in any pairs. If two parameters do not respect the rules, "poor absorption or permeability" is possible, and in the many thousand drugs tested, only a minute number falls outside these parameters. Based on this calculation (Table 6), none of the intermediate molecules of the present disclosure, and only 8 out of the 17 full-sized molecules synthesized on demand, could potentially be poorly absorbed (Table 6). The most common types of violation, for the latter molecules, were the Topological Polar Surface Area (TPSA>140 Å), their molecular weight (MW>450) and the number of H-bond donors (OHNH≤5).

addition a to the PPTase-encoding entD. By supplementing exogenously dihydroxybenzoates, genes entCA are no longer necessary, as they convert chorismate to 2,3-dihydroxybenzoate. entB is still required, as it is a bifunctional protein. Its N-terminus contains the isochorismate lyase, which converts isochorismate to (2S,3S)-2,3-dihydroxy-2,3-dihydrobenzoate, whereas its C-terminus contains the aryl-carrier protein domain. This domain is phosphopantetheinylated by EntD.

By removing entC and entA, the autonomy of *E. coli* for the production of 2,3-Dihydroxybenzoate was removed. The growth medium was supplemented with 2,3-Dihydroxybenzoate and similar molecules, to be taken up by the cell. Vanillic acid, gallic acid, caffeic acid, 5-Bromo-2,4-Dihydroxybenzoic acid and 3,4-Dihydroxy-5-methoxybenzoic acid as alternatives to 2,3-Dihydroxybenzoate were also used as supplements used.

TABLE 6

Lipinski's Rule of Five, number of Rule violations, rotatable bond number and molecular volume of all molecules produced.

| Molecule | MLogP | TPSA (Å) | Atoms (N) | MW | ON (N) | OHNH (N) | Violations (N) | RBN (N) | Volume (Å$^3$) |
|---|---|---|---|---|---|---|---|---|---|
| 1 | −0.01 | 95.58 | 15 | 210.23 | 5 | 5 | 0 | 4 | 193.16 |
| 2 | −0.03 | 107.6 | 20 | 281.36 | 6 | 6 | 1 | 9 | 272.77 |
| 4 | 0.77 | 95.58 | 17 | 238.29 | 5 | 5 | 0 | 6 | 226.76 |
| 5 | 0.26 | 95.58 | 16 | 224.26 | 5 | 5 | 0 | 5 | 209.96 |
| 6 | −0.3 | 107.6 | 19 | 267.33 | 6 | 6 | 1 | 8 | 255.97 |
| 7 | 1.48 | 95.58 | 20 | 272.3 | 5 | 5 | 0 | 4 | 247.77 |
| 9 | 2.1 | 81.58 | 21 | 286.33 | 5 | 4 | 0 | 6 | 265.68 |
| 10 | 1.8 | 95.58 | 19 | 258.28 | 5 | 5 | 0 | 3 | 230.96 |
| 11 | 1.6 | 95.58 | 20 | 272.3 | 5 | 5 | 0 | 4 | 247.77 |
| 12 | 3.44 | 104.81 | 25 | 336.35 | 6 | 5 | 0 | 4 | 294.56 |
| 21 | 2.28 | 95.58 | 20 | 280.37 | 5 | 5 | 0 | 9 | 277.17 |
| 1Tc | 1.24 | 160.71 | 31 | 429.43 | 10 | 6 | 1 | 7 | 372.32 |
| 2Tc | 1.22 | 172.73 | 36 | 500.55 | 11 | 7 | 3 | 12 | 451.93 |
| 2To | 0.59 | 200.46 | 37 | 518.57 | 12 | 9 | 3 | 14 | 469.93 |
| 2So | 0.23 | 200.46 | 36 | 504.54 | 12 | 9 | 3 | 14 | 453.34 |
| 3Tc | 0.65 | 184.76 | 39 | 543.62 | 12 | 8 | 3 | 15 | 497.94 |
| 3Sc | 0.56 | 184.76 | 39 | 543.62 | 12 | 8 | 3 | 16 | 498.15 |
| 3So | −0.07 | 212.49 | 40 | 561.64 | 13 | 10 | 3 | 18 | 516.15 |
| 5Tc | 1.51 | 160.71 | 32 | 443.46 | 10 | 6 | 1 | 8 | 389.12 |
| 5To | 0.88 | 188.43 | 33 | 461.47 | 11 | 8 | 2 | 10 | 407.12 |
| 6Tc | 1.24 | 160.71 | 31 | 429.43 | 10 | 6 | 1 | 7 | 372.32 |
| 6To | 0.32 | 200.46 | 36 | 504.54 | 12 | 9 | 3 | 13 | 453.13 |
| 9Tc | 2.62 | 151.92 | 37 | 505.53 | 10 | 5 | 1 | 8 | 444.11 |
| 9Sc | 2.52 | 151.92 | 36 | 491.50 | 10 | 5 | 0 | 8 | 427.52 |
| 9To | 1.99 | 179.65 | 38 | 523.54 | 11 | 7 | 3 | 10 | 462.11 |

MLogP, Moriguchi's logP, octanol/water partition coefficient, under 4.15
TPSA, Molecular Polar Surface Area, prediction of passive transport of drugs in vivo, no higher than 140 Å
Atoms, number of atoms between 20 and 70 (Ghose-Viswanadhan-Wendoloski CMC drug-like index at 80%)
MW, molecular weight, between 200 and 450
ON, number of H-bond acceptors (N + O), up to 10
OHNH, number of H-bond donors, up to 5
Violations, calculated number of unmet criteria
RBN, rotatable bond number, is a measure of molecular flexibility, which is related with membrane permeability, from 1 to 9
Volume, molecular volume, impacts the ability of molecules to be transported Example 5

This examples addresses whether use of a condensed pathway would result in further diversity by supplying polyhydroxybenzoates exogenously, permitting control over two parts of the nascent molecules.

To achieve control over the selection of (di)hydroxybenzoates to be tethered to the thiol group of EntE, a new biosynthetic pathway was built. This pathway contained solely the biosynthetic genes entB, entE, vibF and vibH, in Methods
Strains, Plasmids and General Growth Media

*Serratia plymuthica* V4, the original producer of serratiochelins donated the serratiochelin biosynthetic genes (schCEBA, schF1F2F3, schG and schH) and clusters. *Escherichia coli* MG1655 (ID NC_000913.3) was the donor of the enterobactin genes entCEBA (IDs 945511, 947426, 946178 and 945284) and entD (ID 945194), while *Vibrio cholerae* El Tor A1552 (ID N16961) donated genes vibF (ID 2614958) and vibH (ID 2615318) (Table 7).

TABLE 7

List of bacterial strains and their genotype and/or phenotype, and respective source and of plasmids, their characteristics and source.

| Strain/Plasmid | Genotype/Phenotype/Description | Source |
| --- | --- | --- |
| Escherichia coli Top10 | Large plasmid cloning strain, F- mcrA Δ(mrr-hsdRMS-mcrBC) Φ80lacZΔM15 ΔlacX74 recA1 araD139 Δ(ara leu) 7697 galU galK rpsL (StrR) endA1 nupG | Geneart ™ Life Technologies |
| E. coli DH5α | Cloning strain, F- Φ80lacZΔM15 Δ(lacZYA-argF) U169 recA1 endA1 hsdR17 (rK-, mK+) phoA supE44 λ- thi-1 gyrA96 relA1 | Laboratory collection |
| E. coli K12 MG1655 | Wild type and enterobactin producer, F- lambda- ilvG- rfb-50 rph-1 | Laboratory collection |
| E. coli Ent− | MG1655, ΔentD::Cam$^r$ ΔentCEBA::Kan$^r$ ΔentF::Gent$^r$ | This study |
| Serratia plymuthica V4 | Serratiochelin producer | 15, 75 |
| Vbrio cholerae O1 El Tor A1552 | WT, O1 El Tor Inaba, vibriobactin producer | Laboratory collection |
| Saccharomyces cerevisiae MaV203 | MATa, leu2-3,112, trp1-901, his3Δ200, ade2-101, gal4Δ, gal80Δ, SPAL10::URA3, GAL1::lacZ, HIS3$_{UAS\ GAL1}$::HIS3@LYS2, can1$^R$, cyh2$^R$ | Geneart ™ Life Technologies |
| pYes-1L | Yeast Artificial Chromosome, S. cerevisiae - E. coli shuttle vector, trp−, Spec$^R$ | Geneart ™ Life Technologies |
| pDSW204 | E. coli replicative expression vector with a medium-strength promoter, IPTG inducible | 76 |
| pWEB-TNC ™ | E. coli cosmid, donor of the cos site | Epicentre ® |
| pEV_S | pDSW204 carrying genes entABCDE and vibHF and a cos site | This study |
| pSP_S | pDSW204 carrying genes schABCEF1F2F3GH and a cos site | This study |

All E. coli strains were maintained on Lysogeny Broth (Miller, Lab Express) medium, supplemented with 15% agar and antibiotic when required. V. cholerae was maintained on agar plates prepared with Marine Broth 2216 (BD Diagnostics). Saccharomyces cerevisiae was maintained on Complete Supplement Mixture medium (CSM, Sunrise Science Products) or CSM-tryptophan dropout, for selection and maintenance of the yeast artificial chromosome (YAC, pYES-1L) carrying the assembled pathways.

Construction of an E. coli Strain for Heterologous Expression of Serratiochelins The serratiochelins biosynthetic pathway shares homology with that of enterobactin. In order to guarantee that the synthetic pathway genes were indeed the ones involved in molecule biosynthesis—versus the homologous in the chromosome—genes entD, entF and entCEBA were removed from the chromosome of E. coli MG1655.

This was achieved using the Lambda Red Recombination system, having entD, entCEBA and entF been replaced with chloramphenicol, kanamycin and gentamicin-resistance cassettes, respectively.

The removal of the enterobactin biosynthetic genes disabled this organism's capacity to assemble this siderophore and grow in iron-limited conditions.

Construction of Compressed Synthetic Pathways for the Assembly of Serratiochelin Analogs From both clusters, only the genes actively involved in the bioassembly of serratiochelins were used (FIGS. 4A and 4B). These genes were amplified by PCR using 5'-3' primers that added the E. coli ribosomal binding site GAGGAGA to the region upstream of the translation initiation codon. In the particular case of genes schCEBA and schF1F2, these were amplified together having an RBS been only added upstream of schC and schF1. The native RBSs were maintained for schEBA and schF2. In the serratiochelins producer, S. plymuthica V4, the condensation-domain containing SchF0 is not involved in the assembly of these molecules, despite its high similarity to EntF. Instead, the V. cholerae VibF homologs SchFJF2F3 are indeed involved.

Given that the serratiochelins biosynthetic pathway seems to descend from the enterobactin and vibriobactin pathways, whether the ancestral genes could assemble the molecule was also investigated as well. Thus, besides building the sch-based compressed synthetic pathway, their ancestral genes, from E. coli and V. cholera, were also used to assemble a homologous pathway.

The genes entD, entCEBA, vibF, vibH, schF1, schF2F3, schH, schG and schCEBA were PCR-amplified from E. coli MG1655 (ent genes), S. plymuthica V4 (sch genes) or V. cholerae El Tor A1552 (vib genes) with overhangs homologous to the genes to be located up and downstream in the compressed pathway. The genes at the beginning and end of each pathway were amplified with 5' primers that added a SpeI restriction site and homology to the YAC pYES-1L (Life Technologies). The genes at the end of the pathways was amplified with 3' overhangs to a cos site (for large construct stability), which was amplified with a 3' primer with homology to the YAC backbone and also contained a SpeI site The amplicons were transformed, and assembled into full pathways, by S. cerevisiae using the Geneart® High Order Genetic Assembly kit (Life Technologies).

The compressed pathways (FIGS. 4A and 4B) were released from pYes-1L by digestion with the restriction enzyme SpeI and each of the inserts was cloned into the same restriction site, added to pDSW204 by PCR.

The level of similarity between the homologous proteins was assessed utilizing the BLAST® blastp suite from the National Center for Biotechnology Information (NCBI).

Criteria for Selection of Exogenously-Supplied Precursors

The substrate limits for VibH to use several amine-containing small molecules as DHB acceptors were tested. The selection of precursors aimed to generate a wide diversity of molecules with a range of chemical properties, as a proof of principle. All polyamine precursors were purchased from Sigma-Aldrich, whereas the dipeptides were synthesized by Biomatik. All precursors selected contained at least two amine groups with at least one hydrogen atom. The product references, names and concentrations used are listed on Table 3.

Putrescine and spermidine are naturally occurring polyamines in E. coli. Though their molecular functions are yet to be fully understood, it has been found that they facilitate mRNA translation. Despite being synthesized endogenously, these compounds were supplied exogenously as well to enable the strain to uptake them and use them for incorporation into the unnatural NRPs. The endogenous levels of production were predicted to be too low and unavailable for the assembly of molecules, besides their natural physiological function.

In order to test whether the compressed and hybrid pathway could assemble serratiochelin and vibriobactin, 1,3-diaminopropane (diaminopropane) and Bis(3-aminopropyl)amine (norspermidine) were added to the medium, respectively. To test whether other analogs could be generated, several different polyamines to be added to the growth medium were selected, e.g., molecules with up to 12 carbons and 4 amine groups (1,5-Diaminopentane, 1,4-Butanediamine dihydrochloride, N,N-Bis(3-aminopropyl)-1,4-diaminobutane, N-(3-Aminopropyl)-1,4-diaminobutane and N,N'-Bis(2-aminoethyl)-1,3-propanediamine), as they were the most similar to diaminopropane and norspermidine. Next, 2,2'-Thiobisacetamide was selected, as the two amides could potentially contribute for metal chelation, similarly to EDTA, as well as provide the amine groups necessary for the condensing reaction catalyzed by VibH. Siderophores are uptaken by cells through specialized transporters. Due to this easy access to the intracellular milieu, some antibiotic molecules have evolved to structurally resemble siderophores. Given the structure of the synthetic antibiotics sulfonamides, two were selected for tentatively generating sideromycins. The two sulfonamides selected, sulfaguanidine and p-aminobenzenesulfonamide, contained two amine groups that in theory VibH could use for condensing with the dihydroxybenzoyl and the threonine-containing intermediate. Next, efforts were made to enhance the fluorescence property of the analogs. In order to achieve this, we selected precursors that contained two benzene rings, in addition to the required amine groups (4,4'-Oxydianiline, 4,4'-Diaminodiphenylmethane and 1,5-Diaminonaphthalene). By providing it with fluorescent properties, it was hypothesized that these molecules could be, e.g., tracked during their export and import process across the membrane and inside the cell. They could also, for example, be used as a $Fe^{2+}$ sensor in the medium, as bacteria will only secrete the iron chelator in low soluble iron conditions.

Despite being a nonribosomal peptide, serratiochelin and other NRP siderophores incorporate natural amino acids in their structure.

Antimicrobial peptides as small as 12 amino acids long, such as KR-12, display strong activity against some bacteria. Thus, whether this pathway would be able to incorporate dipeptides in its structure was tested. Four dipeptides were selected, based on their polarity, hydrophobicity and structural conformation. It is well established how the most efficient antimicrobial peptides are positively charged, for interaction with cellular structures. Thus the incorporation of dipeptides lysine-lysine (KK), lysine-arginine (KR), lysine-glutamine (KQ) and glutamine-asparagine (QN) were tested.

Production and Purification of Hybrid Unnatural Nonribosomal Peptides

Minimal medium optimized for the production of serratiochelins was used for molecule production. It was composed of $Na_2HPO_4$ (5.96 g/L), $K_2HPO_4$ (3.0 g/L), $NH_4Cl$ (1.0 g/L), NaCl (0.5 g/L), $MgSO_4$ (0.058 g/L), $C_6H_{12}O_6$ (5.0 g/L) and IPTG (1 mM), at pH 7.0.

The precursors were added to final concentrations of 0.05 to 10 mM (Table 3). The siderophore production and related machinery was further induced by adding the iron chelator 2,2'-bipyridyl (Sigma-Aldrich D216305) to a final concentration of 0.1 mM to the growth medium.

The cultures were grown for up to 7 days at 30 C with 250 rpm shaking, to an optical density (600 nm) of ≈0.500. After growth cells were spun down and the supernatant filter-sterilized. The cell-free supernatant was loaded onto Sep-Pak tC18 (5 g) Reversed-Phase columns (Waters®). The columns were washed with water and the molecules eluted with 100% acetonitrile.

Liquid chromatography and tandem mass-spectrometry (LC-MS/MS) sample analysis was performed at the Small Molecule Mass Spectrometry core facilities at Harvard University. Two-hundred and fifty microliter-aliquots of each sample were injected into a high-resolution, accurate mass Q Exactive Plus Orbitrap, with positive ionization and mass scan ranging from 66.7 to 1000 m/z (resolution 70,000 FWHM) and operated over the course of 30 minutes at a flow rate of 3 mL/min, with a gradient of 10 ACN in $H_2O$ to 100% ACN. Molecules displaying masses matching the expected one were fragmented (35,000 FWHM) and the respective fragmentation patterns were compared against those of the predicted structures.

The predicted structures for the natural and unnatural molecules potentially produced in-demand were drawn using ChemDraw® Professional 10 (Perkin Elmer). The prediction of the structure was performed based on previous knowledge on the NRPS-based assembly of serratiochelins. As the molecule assembly process had already been elucidated, it was possible to determine the mass and possible configurations of the new, unnatural nonribosomal molecules.

In-Silico Prediction of Biological Activity

In silico tools for prediction of small molecule activity against an array of targets have matured over the course of the last few years. At the current state-of—the art, some of these can be used and reliable indicators of activity and as a first sieve through libraries containing thousands of molecules and pick out those most likely to bind to specific targets.

In order to get an insight into the potential activity of the molecules generated by our programmable compressed pathway, the corresponding SMILES in the online tools Bioactivity Score Calculator (BSC) by Molinspiration, MolSoft and the Swiss Target Prediction (STP) were run.

BSC utilizes Bayesian statistics to compare the structure of active and inactive molecules, on a particular target, to identify new possibly active molecules. Instead of computing an overall value of drug-likeness, BSC focuses on 6 drug classes: GPRC ligands, ion channel blockers, nuclear receptor ligands and protease, kinase and enzyme inhibitors.

MolSoft is an algorithm used to predict the drug-likeness score of molecules, using a set of 5000 active molecules and 10000 inactive molecules.

STP was developed by the Swiss Institute of Bioinformatics and combines 2D and 3D measures of similarity to predict bioactivity against over 2000 targets in humans, horses, mice, rat and cows.

The smaller, intermediate molecules were further analyzed for compliance with Lipinski's Rule of Five. This rule was developed in 1997 by Christopher Lipinski and colleagues, from Pfizer. It considers that an orally active drug has no more than a single violation of the following criteria: (1) 5 or less hydrogen bond donors, (2) 10 or less hydrogen bond acceptors, (3) less than 500 Da and (4) an octanol-water partition (log P) of 5 or less.

entA (SEQ ID NO: 1)
ATGGATTTCAGCGGTAAAAATGTCTGGGTAACCGGCGCAGGTAAAGGTATCGGCTACGCCACGGC

GCTGGCGTTTGTTGAGGCGGGAGCGAAAGTTACAGGTTTTGATCAAGCGTTCACTCAGGAGCAAT

ATCCCTTTGCGACCGAAGTGATGGATGTTGCCGACGCTGCGCAGGTCGCGCAAGTGTGTCAGCGAC

-continued

```
TGTTAGCTGAAACGGAGCGACTGGACGCGCTGGTCAATGCGGCGGGAATTTTACGCATGGGCGCG

ACCGATCAGCTCAGTAAAGAGGACTGGCAGCAGACTTTTGCGGTTAACGTCGGCGGTGCGTTTAA

CCTGTTCCAGCAAACCATGAACCAGTTTCGCCGTCAGCGGGGCGGGGCGATTGTCACTGTGGCGTC

CGACGCCGCGCACACGCCGCGTATTGGCATGAGTGCTTATGGCGCATCGAAAGCGGCGCTGAAAA

GCCTGGCGTTGAGCGTCGGGCTGGAACTGGCGGGTAGCGGCGTGCGCTGTAATGTGGTTTCGCCTG

GCTCCACCGACACCGATATGCAACGCACGCTGTGGGTGAGCGATGACGCCGAAGAACAGCGTATT

CGCGGCTTTGGCGAGCAGTTTAAACTCGGCATTCCGCTGGGGAAAATCGCCCGTCCACAAGAGAT

CGCCAACACGATTTTGTTCCTCGCCTCTGACCTCGCCAGCCATATTACCCTACAGGATATTGTGGTC

GATGGCGGCTCAACGCTGGGGGCATAA
``` entB (SEQ ID NO: 2)

```
ATGGCTATTCCAAAATTACAGGCTTACGCACTGCCGGAGTCTCACGATATTCCGCAGAATAAAGTT

GACTGGGCCTTTGAACCGCAACGTGCCGCGTTGTTAATCCATGATATGCAGGACTATTTTGTCAGC

TTCTGGGGCGAGAACTGCCCGATGATGGAGCAGGTGATCGCGAATATTGCTGCGCTGCGCGACTA

CTGCAAACAGCACAATATCCCGGTTTATTACACCGCCCAGCCGAAAGAGCAGAGCGATGAAGATC

GGGCGCTGTTGAATGATATGTGGGGGCCGGGCCTGACCCGCTCGCCGGAACAGCAAAAGGTGGTG

GATCGCCTGACGCCAGATGCCGACGACACGGTGCTGGTGAAGTGGCGCTACAGCGCGTTTCATCG

TTCTCCGCTGGAGCAAATGCTGAAAGAGAGTGGACGTAACCAGCTGATTATTACCGGGGTATATG

CCCACATTGGCTGTATGACCACCGCAACCGACGCATTTATGCGCGATATTAAACCGTTTATGGTGG

CGGATGCGCTGGCCGATTTCAGCCGTGACGAGCATTTGATGTCGCTGAAATATGTGGCCGGACGTT

CTGGCCGGGTGGTGATGACTGAAGAATTACTGCCAGCACCTATCCCCGCCAGCAAAGCGGCGCTG

CGTGAGGTGATCCTGCCGTTGCTGGACGAGTCCGATGAACCGTTCGATGACGACAACCTGATCGAC

TACGGTCTGGATTCGGTGCGCATGATGGCGCTGGCGGCGCGCTGGCGCAAAGTGCATGGTGATAT

CGACTTTGTCATGCTGGCGAAAAACCCGACCATCGACGCCTGGTGGAAGCTACTCTCCCGCGAGGT

GAAATAA
``` entC (SEQ ID NO: 3)

```
ATGGATACGTCACTGGCTGAGGAAGTACAGCAGACCATGGCAACACTTGCGCCCAATCGCTTTTC

TTTATGTCGCCGTACCGCAGTTTTACGACGTCAGGATGTTTCGCCCGCTTCGATGAACCGGCTGTG

AACGGGGATTCGCCCGACAGTCCCTTCCAGCAAAAACTCGCCGCGCTGTTTGCCGATGCCAAAGC

GCAGGGCATCAAAAATCCGGTGATGGTCGGGGCGATTCCCTTCGATCCACGTCAGCCTTCGTCGCT

GTATATTCCTGAATCCTGGCAGTCGTTCTCCCGTCAGGAAAAACAAGCTTCCGCACGCCGTTTCAC

CCGCAGCCAGTCGCTGAATGTGGTGGAACGCCAGGCAATTCCGGAGCAAACCACGTTTGAACAGA

TGGTTGCCCGCGCCGCCGCACTTACCGCCACGCCGCAGGTCGACAAAGTGGTGTTGTCACGGTTGA

TTGATATCACCACTGACGCCGCCATTGATAGTGGCGTATTGCTGGAACGGTTGATTGCGCAAAACC

CGGTTAGTTACAACTTCCATGTTCCGCTGGCTGATGGTGGCGTCCTGCTGGGGGCCAGCCCGGAAC

TGCTGCTACGTAAAGACGGCGAGCGTTTTAGCTCCATTCCGTTAGCCGGTTCCGCGCGTCGTCAGC

CGGATGAAGTGCTCGATCGCGAAGCAGGTAATCGTCTGCTGGCGTCAGAAAAAGATCGCCATGAA

CATGAACTGGTGACTCAGGCGATGAAAGAGGTACTGCGCGAACGCAGTAGTGAGTTACACGTTCC

TTCTTCTCCACAGCTGATCACCACGCCGACGCTGTGGCATCTCGCAACTCCCTTTGAAGGTAAAGC

GAATTCGCAAGAAAACGCACTGACTCTGGCCTGTCTGCTGCATCCGACCCCCGCGCTGAGCGGTTT

CCCGCATCAGGCCGCGACCCAGGTTATTGCTGAACTGGAACCGTTCGACCGCGAACTGTTTGGCGG

CATTGTGGGTTGGTGTGACAGCGAAGGTAACGGCGAATGGGTGGTGACCATCCGCTGCGCGAAGC
```

```
TGCGGGAAAATCAGGTGCGTCTGTTTGCCGGAGCGGGGATTGTGCCTGCGTCGTCACCGTTGGGTG

AGTGGCGCGAAACAGGCGTCAAACTTTCTACCATGTTGAACGTTTTTGGATTGCATTAA
``` entD (SEQ ID NO: 4)

```
ATGAAAACTACGCATACCTCCCTCCCCTTTGCCGGACATACGCTGCATTTTGTTGAGTTCGATCCGG

CGAATTTTTGTGAGCAGGATTTACTCTGGCTGCCGCACTACGCACAACTGCAACACGCTGGACGTA

AACGTAAAACAGAGCATTTAGCCGGACGGATCGCTGCTGTTTATGCTTTGCGGGAATATGGCTATA

AATGTGTGCCCGCAATCGGCGAGCTACGCCAACCTGTCTGGCCTGCGGAGGTATACGGCAGTATTA

GCCACTGTGGGACTACGGCATTAGCCGTGGTATCTCGTCAACCGATTGGCATTGATATAGAAGAA

TTTTTTCTGTACAAACCGCAAGAGAATTGACAGACAACATTATTACACCAGCGGAACACGAGCGA

CTCGCAGACTGCGGTTTAGCCTTTTCTCTGGCGCTGACACTGGCATTTTCCGCCAAAGAGAGCGCA

TTTAAGGCAAGTGAGATCCAAACTGATGCAGGTTTTCTGGACTATCAGATAATTAGCTGGAATAAA

CAGCAGGTCATCATTCATCGTGAGAATGAGATGTTTGCTGTGCACTGGCAGATAAAGAAAAGAT

AGTCATAACGCTGTGCCAACACGATTAA
``` entE (SEQ ID NO: 5)

```
ATGAGCATTCCATTCACCCGCTGGCCGGAAGAGTTTGCCCGTCGCTATCGGGAAAAAGGCTACTGG

CAGGATTTGCCGCTGACCGACATTCTGACGCGACATGCTGCGAGTGACAGCATCGCGGTTATCGAC

GGCGAGCGACAGTTGAGTTATCGGGAGCTGAATCAGGCGGCGGATAACCTCGCGTGTAGTTTACG

CCGTCAGGGCATTAAACCTGGTGAAACCGCGCTGGTACAACTGGGTAACGTCGCTGAATTGTATAT

TACCTTTTTCGCGCTGCTGAAACTGGGCGTTGCGCCGGTGCTGGCGTTGTTCAGCCATCAGCGTAG

TGAACTGAACGCCTATGCCAGCCAGATTGAACCCGCATTGCTGATTGCCGATCGCCAACATGCGCT

GTTTAGCGGGGATGATTTCCTCAATACTTTCGTCACAGAACATTCCTCCATTCGCGTGGTGCAACTG

CTCAACGACAGCGGTGAGCATAACTTGCAGGATGCGATTAACCATCCGGCTGAGGATTTTACTGCC

ACGCCATCACCTGCTGATGAAGTGGCCTATTTCCAGCTTTCCGGTGGCACCACCGGCACACCGAAA

CTGATCCCGCGCACTCATAACGACTACTACTACAGCGTGCGTCGTAGCGTCGAGATTTGTCAGTTC

ACACAACAGACACGCTACCTGTGCGCGATCCCGGCGGCTCATAACTACGCCATGAGTTCGCCAGG

ATCGCTGGGCGTCTTTCTTGCCGGAGGAACGGTTGTTCTGGCGGCCGATCCCAGCGCCACGCTCTG

TTTCCCATTGATTGAAAAACATCAGGTTAACGTTACCGCGCTGGTGCCACCCGCAGTCAGCCTGTG

GTTGCAGGCGCTGATCGAAGGCGAAAGCCGGGCGCAGCTTGCCTCGCTGAAACTGTTACAGGTCG

GCGGCGCACGTCTTTCTGCCACCCTTGCGGCGCGTATTCCCGCTGAGATTGGCTGTCAGTTGCAGC

AGGTGTTTGGCATGGCGGAAGGGCTGGTGAACTACACCCGACTTGATGATAGCGCGGAGAAAATT

ATCCATACCCAGGGTTACCCAATGTGTCCGGATGACGAAGTATGGGTTGCCGATGCCGAAGGAAA

TCCACTGCCGCAAGGGGAAGTCGGACGCCTGATGACGCGCGGGCCGTACACCTTCCGCGGCTATT

ACAAAAGTCCACAGCACAATGCCAGCGCCTTTGATGCCAACGGTTTTTACTGTTCCGGCGATCTGA

TCTCTATTGATCCAGAGGGTTACATCACCGTGCAGGGGCGCGAGAAAGATCAGATTAACCGTGGC

GGCGAGAAGATCGCTGCCGAAGAGATCGAAAACCTGCTGCTGCGCCACCCGGCGGTGATCTACGC

CGCACTGGTGAGCATGGAAGATGAGCTGATGGGCGAAAAAAGCTGCGCTTATCTGGTGGTAAAAG

AGCCGCTGCGCGCGGTGCAGGTGCGTCGTTTCCTGCGTGAACAGGGTATTGCCGAATTTAAATTAC

CGGATCGCGTGGAGTGTGTGGATTCACTTCCGCTGACGGCGGTCGGGAAAGTCGATAAAAACAA

TTACGTCAGTGGCTGGCGTCACGCGCATCAGCCTGA
``` vibF (SEQ ID NO: 6)

ATGAAAGAAATGACAGCAATGCAAGCGGCTTATTGGCTAGGGCGTCAACACGACTGCTTGCTCGA

TGGTGTGGCCGCGCATCTCTACGCCGAATTTGATGGTCAAGCATTAAATCGACAGGCGCTAACGGA

AGCGGTACGTGCGCTGTACGCGAAACATCCCATGTTACGTTTAGCGATCACCAAGGATGGACAGC

AGAAGATCTTGCCGCTCTCAACTTTCCATCAGCTTAAAGTGGATGACCTATCACAATGGAAGCCAG

ATGAGGTGGAGTCTTTTGTGCATACTAAGCGCCAGCGAATGACCCACCAGATGCTCGATTTAACTC

AGGGAAACCCGATTGAGATCAGCTTGACTCTGTTGCCTGAGGGCAAACACCGATTACACATTGAT

GCGGATATGATTGCGTGTGATGCACAAAGTTTTCGGCTGTTGGTGGACGATCTCACCTCACTCTAT

TTAGAGGCCATAGAGCATCGATTAGAGATCATTGAGTCTGATGTGGTGACTTTTTTCCAATATCTT

GATGCTCAGCAAGCCGATCGTGCTTTGGCAAAACGCAAAGAGGTGGATAAGAAATGGTGGCAAGA

GCGTCTTGCGACGATTCCCGCCGAGCCAAGTTTGCCTTATCAACCCGTACCAACCGACGCCGTTAG

CGCAAACAGCCAAAGGTTTGCACACTGGTTCACTCCAGTGGAGCGCAAAGGGTTGGCGGAGGTTG

CGCGGCAACATCATCTCACACTGACCCAACTGACATTGGCACTCTTTTCACAAGTGATTGCCAATG

CTTGCCAAGAGAGACAATTTCGACTCAATGTACCTACATTCCATCGCGGCAATCGCTCTTTGGATA

TTGAACACACGATCGGCGATTTTTCCAATTTGCTGATTITTAGCGCCGATGTGGGAACGACTCAGA

CCCTGTTAAGCCTGTGTCAGCAAACGGCTAACCAACTGCATCAATTACTTCGCCATGAAAG

CTATTCAGGGGTTAGCGTGATGCGCGATTTATCGCGGAAACAGGGTGGGGTGCAGCGTTCACCGA

TAGTCTTTACCTCAGGCATGGAAATGCGAGACGAGGAGATCTTTTCCGATCATGTCACTCAGCATT

TAGGGCGTATGAATTGGGTGATTTCGCAGGGAGCGCAGGTGACTCTCGATGCGCAAATTGCTCCG

GCTTATGAAGGGATTTTGCTCAATTGGGATGTGCAATGGAAAACTTCGCTGATAAGGACATCACA

GCGCTTTTCGCGCATTACGTTGATTTGATCCGCTGTGTGGCGCTGCATCCTGAGATGATGCAGCAA

AGCGTACAACAGATTGACGCGCAACTCGGTTATGCTCGCCGCGAGTCGATTCAGGAGATGCCACT

GACCCCTTTACAACAAGCTTACTTGCTAGGTCGCTCAACCCAAATTGCCTTAGGCGGCGTCGCGAT

GCATGAGTTTCGTGAGTATCGAGGTCACATCGACACTCAGTCACTGCATAGCCGTCTGCTCTATCT

CGTTGAGCATATTCCTGCCTTGAGAACTCGCATTGATCAAGAGAAATGGATTCAGTGGGTCTCTCC

TTGCATAGCGTTAAATTGGCAAGCCATCGATTTACAGCATCTTTCCCGCGAACAAGCCTTATTAGC

GGTTGAGCCAGTCAGGCAGCAATATCAGCAGCGGATGCATGATTTAACGCGCTCGCCCTGGCAAA

TCTGTGTGGTGCAACTGCCAATAGAAGAGCAAGAGGAGTTCAGCTCCATCGTATTGACCAGCTTTG

ATGCTTTGATTGTCGATGGTCGCACCCATGCACTCATTCTTGCTGCACTACTAGGAAGCGAAGAAC

CCGATATAACTCAGGTGGTGCAAAATGCTCGTGATACTCAGTCCATCTCGCCGCAATTCGCCTCCA

AAAAAGCGCAAGATGAAGCGTATTGGAAAAGCAAACTTCATCCTGATTGCCCGCCGCCAGCACTG

CCTTGGAAACAAGCATTAGAGACGATCACTACGTCTCGTTATGCTCGTGAAAGTTTGCAAATACCC

AAAGAGAGTGTCGGTAAGCTCAATCGATGCGGCATTGAAAATGGCTTATTTCTCAATTCCTTGCTG

ACAGCAACCATCTTGGACGTGCTCTCCTATTGGACAACCGAAATCGGGATGCGAGTGGGTTTTCCG

GTATTAATTCCAAGCAGTAATGCGATTGATGGCAATGAGTCATCCTTTGTGATCTTAGAGCATGAA

AAATCCACCCTGAGTTTGCTGAGCCAAGCGAGCAAGCTACAGCGTGAGATGCTAGAGGCTCTTGA

GCATCTTGCTTTTTCTGGCGTCGATCTTAACCGTCTGTTGATGAATCAAGCGCCGCAAGCTCTGGTG

CTGCCGGTTGTGTTAACCAATGGTTTGTCTTGGAAAACCCTGAATCCAGAGGACGCTGTCACTCTG

TTCGATGGGGTAACGCAAACTCCGCAGTGGCTTTAGATATTCGCTTAACTTACGACGAGCAGAAAA

ACCTCATCATCAGCTTTGATTATGCTTTAGCGGTTTTAGAGACTGAGCTTATCCGCGAGATGTTAAG

-continued

```
TGCCTTACATCATCGCTTGAGTCAGATCACTTCGTCAGCATCATTGGCCGCGCCGCTTGAGCCATGT
ATCGACCTTTCACACTACCGTTTTAATAGCGATGAGTCGGCCAGTCACGATTGCGATTTTCTTGCCA
AGTTAGCGCAGCAATTGTTTGTCCGCACAGAGGATAAAACCGCTGTGATCTGCGGTGAACAAACC
CTTTCTTATGCTCAATTGGGTGAGCAGGTTCAGCGCGTGATGTGGCAGCTCAAAGCGCGAGGGTTG
ACCACAGGAAATGTGCTCGCCATTTGCTTGCCACGCAGTGTTGAACATATCGTCATCAGTTTGGCT
TCTGCACTTTCGGGGATTATCTGGGTACCTATTGATGCTGCGTCTCCCAAAGAGCGTCTGAATTACC
TTTTAGAAAATTGTCACGCCGATCTGGTGGTGATGGATAAGCCCTGTGAGTTTGGCAATGTGATCG
CTTTTGATGCCTTGATTGAGCCTGTCTTATTCGCCGATGGAGTACCTGACGTTACACCACTCGATCA
ATTAAGCCGATTAAGCCAAAGCCAACAAACGGCTTATTATCTTTATACCTCTGGCACTACGGGCAA
ACCTAAGTGCGTGGTGGTCAATAATCAGGCGACCTCGAATGTGATTGGTCAAACTGGCCAAGCGT
GGCATCTCACCAGTGAGGATGTGGTGATGTCAGTGACGCCATTGCATCATGATATGTCGGTGTTTG
ATCTCTTTGCCACCTTGAGCTTCGGAGCGACGTTAGTTCTTCCCGCTGGGCATGAAGAAAAAGATG
CGTTGCAATGGAATCGCTTAATTGAGCGGCATCAAGTGACGATTTGGGTCTCCGTCCCCGCTATCT
TGGAGATGTTGCTCTCTTGCACTCAAGCAGGGCAATTACACTCACTTCGTCTGATTGCCCAAGGGG
GGGATTACATCAAACCTGCCACCATCGCCCAATTACGCGCTGGTTCAAATCCGCCGCGGTTGATCT
CTTTGGGCGGTCCTACCGAGACGACGATTTGGAGCATCTGGCATGAGCTGACGGCAGATGATGTC
AGCGTGATCCCATATGGTCGGCCGTTGGCGGGAAACCGTTATTTCATTATGGATGAGATACAACGC
CATGTACCGCAAGGTGTGGTCGGCCGTATCTTCACCTCTGGGGTCAATTTAGCGCAAGGTTATCTT
GAAGACGGCGAACTGAAACAAACCGATTTTGTCACCGTATTGGATGAGCATGGCCACCCTGTGCG
CGCGTTTCGAACGGGCGATCAAGGCTACTACCGCGCGGACGGCAATATCATTTTTGCTAGCCGCAT
CAATGGTTATGTGAAAGTTCGTGGGGTACGAGTGTCACTGCCGGATATCGAAAAGCAGCTGCAAA
CTCATCCGGCGCTCGCGAGCGTGGTGGTGGTCGATTATGCGGATACTAATGGAGATACCGCTTTAG
CCGCATTATTTAGCGTTAAACCTCAGCAATCAGCATCGAGTCAGGCGTTACGAGAGTTTGCCAAAC
AATCGCTACCGTCTTCGCATATTCCGAGTCGGTTTATTGCTTTAGAGGCTTTACCGCTTTCTGCGAA
TGGTAAAGTGGATCGCAAACAGTGCCAAGCGCATGTTCAGCGACAATCGATCTCTGTTGAACCAG
TAGGTCAACCGAATCAAAGTCAACCTCTCTCACCACCTACCTTGTCATCGGCTTCCTTGAGTGAGTT
TGAACAGCGAGTCTGGCGACAGCATCAACGACATGGTGACGGACGCAATCAATATGCGACCGCTT
ATCGATTGAGCGGAAAAGTGAATATCGCGCGCTTAATCACAGCGCTCAGTCAGTTGCCCAATCATT
TTCCAGTGTTAAACCGACGCTATGTGCTTGATGAGGCATCCGGCTTAACCTTGTACTCGGCGAAGC
CAACACCGCTTGAGATCCATTTTGAGCATGTTGAGTCAATGGATGAGGCGTTTGAACATCTTGTGC
GATGGCAAAATCAGCCGATGGATTTAGCCAAGCAAGCCACACTAAGTTTTTGCTTGTTGAGTTTGG
GGAGCGAAGAGCGAGTGCTTGGGGTGATAAGCCATCAAATTATCAGCGAGCAATGGGATTGGCGG
CGCGTATTTGAGTGCGTAACCAATGGGTATAACCAAATCGCCTGTGACATCGATCCTGTGATGGAG
GGGGAGGATCTTTCCCTCGGCTTTACCCCTGTGATGCCGCAAACGCCATTATCCCAAGCGTTGTTG
CCGTGGTTACAGCCTGCGAGCCACGCTACATGGATTGAGCAGAGCTTGCCGAGCGCAAATAGCGC
CATCAATACGCTTTGCAGTCGTAAATATCGGATTGCCCTACACAGCAGCGTACTGGCGGAGCATGG
TTTAGCGCAGCCGGATAAGCAGGAAGTGCTTGCACTGATCGCCGCGTTATTTGCTCGCTACCTTGC
CGCAAGTGCGAAACTTGGCCAATTTGAGCTTTACGTTCCGCATGATGTGGAGCGCAAAACGCGTG
AGTTGAATGGTTCTATGATTGAAAGCCAGTTGGTGCATATCGCCCTTAAAGGCTTTGAGCGTCCGC
TTTCGCAACTGAGCCAAGAGATCTTAGACGCTATGCGCCAGCCGTTAACGGGGGAGTCGCTAGC
GAAACTCACGCCTCTGCCGCAGCCTTGGTGACTTGGTTAGTGGATCCTTCAGTGCATCTACAATTG
```

```
GAGGGCTTGCGCTGCGAAAAATTACTTTTTGCAGCCATGCACCCCAAATTTGAAGTCGCCTTGGGG
GTTGGGCTTAATTGCCAAGGTGCCCTAGTACTTGAGCTGGCGTTAGATGCCACGGTTTCCCCCCAT
GTCGGAGCCTACTTGCTTGAGCAATTTGTCGCTGCGATAGGTGGGCGAACAATGCCTTCTTCGACA
ACCTCATCCTCTCATGTCTCAGCCATTGAGTTGACGTCAAACAATCCGCCGACCTCAAACAATGCG
CATGCGGCGTTGGCAGAGTCTGAGCTTGAATTGAGCGCTGTAAATTCCTCTGCGGTTGAAGAGTGC
ATTTTGGCTGAGTTTCGCTCAGCACTTGGTGTTGCCGAGATGACGGCAGAGGATGATTTCTTTGATT
TTGGCGGACATTCCCTGATCGCAACGCGAGTCATTGGTCGCTTGTTGAGCGAGCAAGGTATTGAAC
TGCACATCAATGATATGTTTAGTTTCCCTAATGCCAAGCAACTGGCGCAGCAAGCCGTACTTCACC
GTAAACCCACCAGCACATCATTCGCAGTGAGTGAGGTGGTCGAGTCGTCCAAAGCGCCTTTGTCGT
TAGCACAAGCCTCTTTATGGAAGGCGATGAGCAAATACGCCAAGTTTGGTTTGACCCACATCTTCA
ATCTTCCGTTTGCGCTTAAATTTTTAGATGAGGTCAATGAGCAAGCATTTGGTGAGGCTTTTCACTG
GCTTTTACTGCGTCATGCTGGGTTACGAACCCACTTTGGCCTAGAAGATGGGCAGCCTTACCAGCA
CGTGATCGCAGCCAGCAACATAGAACATTACCAGTGGTTCTGGACGTCTAAAGATAACGCCGCCC
AATCCGTGGCCAGACTACTGGCGCAAGAGGCCGAGCACACCTTTGACCTGAGCCAAGAATTGCCA
CTTCGACTCAATTTCGTACGTGATGAACAGACGGGGACGCAATATCTTTCACTTCTGTTCCACCAT
ATTGTGTTGGATGAGTGGTCGATCAATATTTTGATGGATGAATTAGCACAGGTGTATCAACACAGT
GTGCAAGGTACTCGTCCACAGTGGCAAACGGAACCCTTACCTTTCCATGAGTTTGCTCGCAAGCAG
CGTTCTTCGGCATTCAATCAAACGCATCTTAACTATTGGTTAACCAAGTTTGCCGGTGTGCCTTGGG
CACAGCCTCTGTTTGCTGCGGATCATCCTTTAAGTAACAGCACTGGCGTCGATCTTGGAGAAGGCG
GCTGGGTCGAAATAAAATTGCCGAAATCAACCATGGTATCGCTGTATCAATTGGCTAAAGCACGC
CATGCTTCGTTGTTTAACGTGATGTATGCGGCGATTTCTGCGTCGGTACATTGTCTCGGCGCACCAG
AAAAGCTGCTGGTTGGCACACCTGCTTCCGGTCGGCTGGATGCCGAGTTTTTCGACACAGTCGGTT
ATTTCACTACCATGGGCGTTCAGTTGGTGGATTTCACGAAAGTACAAACGGTGTGGCAACTCATCG
AGCAAGTGAAAAACAGCATTAACCAGTCGATGCCATACACAGATATTCCGATTGACCTGATTGAA
GAAGGGCTCAAAGGTGTTGAGCATGAGACGGAAGGTCACATGTTTGAGGTCTTTATACAACTGCA
TGCAAAAAATAAGCTGCATGGAGAGCTACTGTTGACAGAAGGGCATGCGATCCGCTTCCAACAAG
TCGATCCCGATAAAGTGAATCCGGCTTAGGTTTACAGTTTGAAATTTTAGAAGAGAGGATCGAGC
AAAAGCAGACGTTGAGAGTCATGATGAGTTATATGTCGAAACACTATAGCCCAGCTCAAGTCGCT
CTGTTGACCAAGGTAACCAGTGGCATGTTTGAGCGGTTTTCCGATTGTATTGCACAAGATATTGCA
CTGCCGACGCTGAAAAAGCAGGTGAGGCAGCTTGAAGATGAAGCTTGTCGCTCTCCGTCCATGGG
GTAG
vibH
                                                              (SEQ ID NO: 7)
GTGTCTATGTTATTGGCTCAAAAGCCTTTTTGGCAGCGCCATCTGGCTTATCCTCACATTAATCTCG
ACACCGTTGCCCATTCGCTACGCCTGACAGGGCCTTTAGATACCACACTTTTGCTGCGCGCATTGC
ATTTAACCGTCAGTGAGATAGATCTGTTCCGTGCTCGCTTTTCTGCGCAAGGTGAGCTGTATTGGC
ACCCATTTTCTCCGCCTATCGACTATCAAGACCTCAGCATCCACCTTGAAGCAGAACCTTTAGCTTG
GCGGCAAATAGAGCAGGATTTACAGCGCTCAAGCACACTGATTGACGCGCCAATAACGAGCCATC
AAGTGTATCGTTTGTCACACAGTGAGCACCTTATCTATACCCGTGCGCACCACATTGTGCTGGACG
GTTATGGCATGATGCTGTTTGAGCAGCGCCTCAGCCAACATTACCAATCCTTGCTCAGTGGGCAGA
CGCCAACTGCCGCGTTTAAACCTTATCAATCCTATCTGGAAGAAGAGGCGGCTTATCTTACCAGCC
```

```
-continued
ATCGCTACTGGCAAGATAAGCAGTTTTGGCAAGGCTATTTACGCGAAGCTCCCGACTTAACGCTCA

CCTCTGCAACCTATGATCCTCAACTTAGTCATGCCGTGAGCCTCTCTTACACACTCAATAGCCAACT

CAACCATTTGTTACTCAAGCTCGCTAACGCGAATCAGATTGGCTGGCCTGATGCCTTAGTCGCGCT

GTGCGCGCTCTATTTGGAATCGGCTGAACCTGATGCGCCTTGGCTGTGGCTGCCCTTTATGAACCG

ATGGGGCAGCGTGGCCGCTAATGTGCCCGGTTTAATGGTTAACTCGCTGCCCTTGCTGCGTCTTTCT

GCGCAGCAAACCTCGCTCGGCAACTACCTTAAACAGTCAGGGCAAGCGATACGCTCACTCTATTTG

CATGGCCGCTATCGAATTGAACAAATCGAACAAGATCAAGGGCTAAATGCTGAGCAAAGTTATTT

TATGAGCCCATTTATCAATATTTTGCCTTTTGAATCCCCACACTTTGCTGATTGCCAGACTGAGCTC

AAGGTGCTGGCTTCAGGCTCTGCAGAAGGGATTAATTTTACCTTTCGTGGCTCACCCCAGCATGAA

CTCTGTCTAGACATCACCGCAGATTTAGCCAGCTACCCGCAATCCCACTGGCAAAGTCATTGCGAG

CGGTTTCCACGTTTTTTCGAGCAGTTACTCGCCCGTTTCCAACAGGTGGAGCAAGATGTTGCACGC

CTACTCGCAGAGCCTGCGGCATTGGCAGCCACCACCTCCACACGGGCTATCGCCAGTTGA
```

REFERENCES, INCORPORATED HEREIN

1. Bérdy, J. Bioactive Microbial Metabolites—A Personal View. *J. Antibiot.* (Tokyo). 58, 1-26 (2005).
2. Walsh, C. T. Polyketide and nonribosomal peptide antibiotics: modularity and versatility. *Science* (80-.). 303, 1805-1810 (2004).
3. Fischbach, M. A. & Walsh, C. T. Assembly-line enzymology for polyketide and nonribosomal Peptide antibiotics: logic, machinery, and mechanisms. *Chem. Rev.* 106, 3468-3496 (2006).
4. Walsh, C. T. Insights into the chemical logic and enzymatic machinery of NRPS assembly lines. *Nat. Prod. Rep.* 00, 1-9 (2015).
5. Ando, H. et al. *Synthetic Biology and Therapies for Infectious Diseases. Novel Antimicrobial Agents and Strategies* (Wiley-VCH Verlag GmbH & Co. KGaA, 2015).
6. Hopwood, D. A. et al. Production of 'hybrid' antibiotics by genetic engineering. *Nature* 314, 642-644 (1985).
7. Thaker, M. N. et al. Identifying producers of antibacterial compounds by screening for antibiotic resistance. *Nat. Biotechnol.* 31, 922-927 (2013).
8. Katsuyama, Y., Funa, N., Miyahisa, I. & Horinouchi, S. Synthesis of Unnatural Flavonoids and Stilbenes by Exploiting the Plant Biosynthetic Pathway in *Escherichia coli*. *Chem. Biol.* 14, 613-621 (2007).
9. Nguyen, K. T. et al. Genetically engineered lipopeptide antibiotics related to A54145 and daptomycin with improved properties. *Antimicrob. Agents Chemother.* 54, 1404-1413 (2010).
10. Weissman, K. J. The structural biology of biosynthetic megaenzymes. *Nat. Chem. Biol.* 11, 660-670 (2015).
11. Chu, B. C. et al. Siderophore uptake in bacteria and the battle for iron with the host; a bird's eye view. *Biometals* 23, 601-11 (2010).
12. Brot, N., Goodwin, J. & Fales, H. In vivo and in vitro formation of 2,3-dihydroxybenzoylserine by *Escherichia coli* K12. *Biochem. Biophys. Res. Commun.* 25, 454-461 (1966).
13. Griffiths, G. L., Sigel, S. P., Payne, S. M. & Neilands, J. B. Vibriobactin, a siderophore from *Vibrio cholerae*. *J. Biol. Chem.* 259, 383-385 (1984).
14. Ehlert, G., Taraz, K. & Budzikiewicz, H. Serratiochelin, a New Catecholate Siderophore from *Serratia marcescens*. *Zeitschrift fur Naturforsch.—Sect. C J. Biosci.* 49, 11-17 (1994).
15. Seyedsayamdost, M. R. et al. Mixing and matching siderophore clusters: structure and biosynthesis of serratiochelins from *Serratia* sp. V4. *J. Am. Chem. Soc.* 134, 13550-3 (2012).
16. Fischbach, M. a, Walsh, C. T. & Clardy, J. The evolution of gene collectives: How natural selection drives chemical innovation. *Proc. Natl. Acad. Sci. U.S.A* 105, 4601-4608 (2008).
17. Budzikiewicz, H. *Fortschritte der Chemie organischer Naturstoffe/Progress in the Chemistry of Organic Natural Products, Vol. 92. Fortschritte Der Chemie Organischer Naturstoffe* 92, (Springer Vienna, 2010).
18. Gehring, A. M., Bradley, K. A. & Walsh, C. T. Enterobactin biosynthesis in *Escherichia coli*: Isochorismate lyase (EntB) is a bifunctional enzyme that is phosphopantetheinylated by EntD and then acylated by ente using ATP and 2,3-dihydroxybenzoate. *Biochemistry* 36, 8495-8503 (1997).
19. Wyckoff, E. E., Stoebner, J. A., Reed, K. E. & Payne, S. M. Cloning of a *Vibrio cholerae* vibriobactin gene cluster: identification of genes required for early steps in siderophore biosynthesis. Cloning of a *Vibrio cholerae* Vibriobactin Gene Cluster: Identification of Genes Required for Early Steps in Siderophor. 179, 7055-7062 (1997).
20. Wyckoff, E. E., Smith, S. L. & Payne, S. M. VibD and VibH are required for late steps in vibriobactin biosynthesis in *Vibrio cholerae*. *J. Bacteriol.* 183, 1830-1834 (2001).
21. Keating, T. A., Marshall, C. G. & Walsh, C. T. Vibriobactin biosynthesis in *Vibrio cholerae*: VibH is an amide synthase homologous to nonribosomal peptide synthetase condensation domains. *Biochemistry* 39, 15513-21 (2000).
22. Voss, J. J. De, Rutter, K., Schroeder, B. G., Iii, C. E. B. & Voss, J. J. D. E. Iron Acquisition and Metabolism by Iron Acquisition and Metabolism by Mycobacteria. *J. Bacteriol.* 181, 4443-4451 (1999).
23. Gobin, J., Wong, D. K., Gibson, B. W. & Horwitz, M. A. Characterization of exochelins of the *Mycobacterium bovis* type strain and BCG substrains. *Infect. Immun.* 67, 2035-2039 (1999).
24. Snow, G. a. Mycobactins: iron-chelating growth factors from mycobacteria. *Bacteriol. Rev.* 34, 99-125 (1970).
25. Keating, T. A., Marshall, C. G. & Walsh, C. T. Reconstitution and characterization of the *Vibrio cholerae* vibriobactin synthetase from VibB, VibE, VibF, and VibH. *Biochemistry* 39, 15522-15530 (2000).

26. Marshall, C. G., Burkart, M. D., Keating, T. a. & Walsh, C. T. Heterocycle formation in vibriobactin biosynthesis: Alternative substrate utilization and identification of a condensed intermediate. *Biochemistry* 40, 10655-10663 (2001).

27. Page, W. J. & Tigerstrom, M. V. Aminochelin, a Catecholamine Siderophore Produced by *Azotobacter vinelandii*. *Microbiology* 134, 453-460 (1988).

28. Cornish, A. S. & Page, W. J. Role of molybdate and other transition metals in the accumulation of protochelin by *Azotobacter vinelandii*. *Appl. Environ. Microbiol.* 66, 1580-1586 (2000).

29. Bergeron, R. J. & Brittenham, G. M. *The Development of Iron Chelators for Clinical Use*. (CRC Press, 1993).

30. Olivieri, N. & Brittenham, G. M. Iron-Chelating Therapy and the Treatment of Thalassemia. *Blood* 94, 837-845 (2015).

31. WHO 19th Model List of Essential Medicines. at who.int/medicines/publications/essentialmedicines/en/

32. Ahmed, E. & Holmström, S. J. M. Siderophores in environmental research: Roles and applications. *Microb. Biotechnol.* 7, 196-208 (2014).

33. Hickford, S. J. H. et al. Petrobactin sulfonate, a new siderophore produced by the marine bacterium *Marinobacter hydrocarbonoclasticus*. *J. Nat. Prod.* 67, 1897-9 (2004).

34. Zheng, Tengfei, E. M. N. Siderophore-based detection of Fe (iii) and microbial pathogens. *Metallomics* 4, 866-880 (2012).

35. Molsoft—molecules in silico. (2016). at molsoft.com/mprop/

36. Molinspiration. at molinspiration.com/cgi-bin/properties

37. Schöneberg, T. et al. Mutant G-protein-coupled receptors as a cause of human diseases. *Pharmacol. Ther.* 104, 173-206 (2004).

38. Birch, P. J., Dekker, L. V., James, I. F., Southan, A. & Cronk, D. Strategies to identify ion channel modulators: Current and novel approaches to target neuropathic pain. *Drug Discov. Today* 9, 410-418 (2004).

39. Ion Channel Drug Discovery. (The Royal Society of Chemistry, 2015). doi:10.1039/9781849735087

40. Patterson, H., Nibbs, R., Mcinnes, I. & Siebert, S. Protein kinase inhibitors in the treatment of inflammatory and autoimmune diseases. *Clin. Exp. Immunol.* 176, 1-10 (2014).

41. Patick, a K. & Potts, K. E. Protease Inhibitors as Antiviral Agents Protease Inhibitors as Antiviral Agents. 11, 614-627 (1998).

42. Griffith, D., Parker, J. P. & Marmion, C. J. Enzyme inhibition as a key target for the development of novel metal-based anti-cancer therapeutics. *Anticancer. Agents Med. Chem.* 10, 354-370 (2010).

43. Willett, P., Barnard, J. M. & Downs, G. M. Chemical Similarity Searching. *J. Chem. Inf. Model.* 38, 983-996 (1998).

44. Craddock, N., Owen, M. J. & O'Donovan, M. C. The catechol-O-methyl transferase (COMT) gene as a candidate for psychiatric phenotypes: Evidence and lessons. *Mol. Psychiatry* 11, 446-458 (2006).

45. Autexier, C. & Lue, N. F. The structure and function of telomerase reverse transcriptase. *Annu. Rev. Biochem.* 75, 493-517 (2006).

46. Iqbal, K., Gong, C.-X. & Liu, F. Microtubule-associated protein tau as a therapeutic target in Alzheimer's disease. *Expert Opin. Ther. Targets* 18, 307-318 (2014).

47. Šerý, O. et al. Arachidonate 5-lipoxygenase (ALOX5) gene polymorphism is associated with Alzheimer's disease and body mass index. *J. Neurol. Sci.* 362, 27-32 (2016).

48. Nutt, D. J., Lingford-Hughes, A., Erritzoe, D. & Stokes, P. R. A. The dopamine theory of addiction: 40 years of highs and lows. *Nat Rev Neurosci* 16, 305-312 (2015).

49. An, S. et al. Identification and characterization of a melanin-concentrating hormone receptor. *Proc. Natl. Acad. Sci. U.S.A* 98, 7576-7581 (2001).

50. Konieczny, P., Stepniak-Konieczna, E. & Sobczak, K. MBNL proteins and their target RNAs, interaction and splicing regulation. *Nucleic Acids Res* 42, 10873-10887 (2014).

51. Contet, C., Kieffer, B. L. & Befort, K. Mu opioid receptor: A gateway to drug addiction. *Curr. Opin. Neurobiol.* 14, 370-378 (2004).

52. Lipinski, C. A., Lombardo, F., Dominy, B. W. & Feeney, P. J. Experimental and computational approaches to estimate solubility and permeability in drug discovery and development settings. *Adv. Drug Deliv. Rev.* 64, 4-17 (2012).

53. Felnagle, E. A. et al. Nonribosomal peptide synthetases involved in the production of medically relevant natural products. *Mol. Pharm.* 5, 191-211 (2008).

54. Demain, A. Pharmaceutically active secondary metabolites of microorganisms. *Appl. Microbiol. Biotechnol.* 52, 455-463 (1999).

55. Walsh, C. Antibiotics: actions, origins, resistance. (ASM Press, 2003). at books.google.com/books?id=6syC2OsTW0AC&pgis=1

56. Gao, X., Wang, P. & Tang, Y. Engineered polyketide biosynthesis and biocatalysis in *Escherichia coli*. 55 *Appl. Microbiol. Biotechnol.* 88, 1233-1242 (2010).

57. Khosla, C., Herschlag, D., Cane, D. E. & Walsh, C. T. Assembly Line Polyketide Synthases: Mechanistic Insights and Unsolved Problems. *Biochemistry* 53, 2875-2883 (2014).

58. Winn, M., Fyans, J. K., Zhuo, Y. & Micklefield, J. Recent advances in engineering nonribosomal peptide assembly lines. *Nat. Prod. Rep.* 317-347 (2016). doi:10.1039/C5NP00099H 59. Wyckoff, E. E., Stoebner, J. A., Reed, K. E. & Payne, S. M. Cloning of a *Vibrio cholerae* vibriobactin gene cluster: identification of genes required for early steps in siderophore biosynthesis. *J. Bacteriol.* 179, 7055-7062 (1997).

60. Datsenko, K. A. & Wanner, B. L. One-step inactivation of chromosomal genes in *Escherichia coli* K-12 using PCR products. *Proc. Natl. Acad. Sci. U.S.A* 97, 6640-5 (2000).

61. Altschul, S. F., Gish, W., Miller, W., Myers, E. W. & Lipman, D. J. Basic local alignment search tool. *J. Mol. Biol.* 215, 403-10 (1990).

62. Altschul, S. F. et al. Protein database searches using compositionally adjusted substitution matrices. *FEBS J.* 272, 5101-5109 (2005).

63. Altschul, S. F. et al. Gapped BLAST and PS I-BLAST: a new generation of protein database search programs. *Nucleic Acids Res* 25, 3389-3402 (1997).

64. Tabor, C. W. & Tabor, H. Polyamines in microorganisms. *Microbiol. Rev.* 49, 81-99 (1985).

65. Abraham, K. Studies on DNA-Dependent RNA Polymerase from *Escherichia coli*. *Eur. J. Biochem.* 5, 143-146 (1968).

66. Frydman, L. et al. Interactions between natural polyamines and tRNA: An 15N NMR analysis. *Proc. Natl. Acad. Sci.* 89, 9186-9190 (1992).

67. Huang, S.-C., Panagiotidis, C. A. & Canellakis, E. S. Transcriptional effects of polyamines on ribosomal proteins and on polyamine-synthesizing enzymes in *Escherichia coli*. *Biochemistry* 87, 3464-3468 (1990).
68. Sakamoto, A. et al. Three Members of Polyamine Modulon under Oxidative Stress Conditions: Two Transcription Factors (SoxR and EmrR) and a Glutathione Synthetic Enzyme (GshA). *PLoS One* 10, e0124883 (2015).
69. Mercado, G., Tello, M., Marin, M., Monasterio, O. & Lagos, R. The production in vivo of microcin E492 with antibacterial activity depends on salmochelin and EntF. *J. Bacteriol.* 190, 5464-5471 (2008).
70. Wang, G. Structures of Human Host Defense Cathelicidin LL-37 and Its Smallest Antimicrobial Peptide KR-12 in Lipid Micelles. *J. Biol. Chem.* 283, 32637-32643 (2008).
71. Cheng, T., Li, Q., Zhou, Z., Wang, Y. & Bryant, S. H. Structure-based virtual screening for drug discovery: a problem-centric review. *AAPS J.* 14, 133-41 (2012).
72. Storrs, C. Screening Goes In Silico. The Scientist (2015). at the-scientist.com/?articles.view/articleNo/41979/title/Screening-Goes-In-Silico/
73. Gfeller, D. et al. SwissTargetPrediction: A web server for target prediction of bioactive small molecules. *Nucleic Acids Res.* 42, 1-7 (2014).
74. Gfeller, D., Michielin, O. & Zoete, V. Shaping the interaction landscape of bioactive molecules. *Bioinformatics* 29, 3073-3079 (2013).
75. Lipinski, C. a, Lombardo, F., Dominy, B. W. & Feeney, P. J. Experimental and computational approaches to estimate solubility and permeability in drug discovery and developmental settings. *Adv. Drug Deliv. Rev.* 23, 3-25 (1997).
76. Ertl, P., Rohde, B. & Selzer, P. Fast Calculation of Molecular Polar Surface Area as a Sum of Fragment Based Contributions and Its Application to the Prediction of Drug Transport Properties. *J. Med. Chem.* 43, 3714-3717 (2000).
77. Ghose, A. K., Viswanadhan, V. N. & Wendoloski, J. J. A Knowledge-Based Approach in Designing Combinatorial or Medicinal Chemistry Libraries for Drug Discovery. 1. A Qualitative and Quantitative Characterization of Known Drug Databases. *J. Comb. Chem.* 1, 55-68 (1999).
78. Cleto, S. et al. Genome Sequence of *Serratia plymuthica* V4. *GenomeA* 2, 5-6 (2014).
79. Weiss, D. S., Chen, J. C., Ghigo, J. M., Boyd, D. & Beckwith, J. Localization of FtsI (PBP3) to the septal ring requires its membrane anchor, the Z ring, FtsA, FtsQ, and FtsL. *J. Bacteriol.* 181, 508-520 (1999).

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of producing a nonribosomal molecule, the method comprising culturing a modified bacterial cell in the presence of an exogenous polyamine linker precursor, under conditions that results in the production of the nonribosomal molecule, wherein the modified bacterial cell is transformed with a compressed biosynthetic pathway that comprises:
    (a) *Escherichia coli* biosynthetic genes comprising an entA gene, an entB gene, an entC gene, an entD gene and an entE gene encoding a 2,3-dihydro-2,3-dihydroxybenzoate dehydrogenase, a 2,3-dihydro-2,3-dihydroxybenzoate synthase, an isochorismate synthase, an Sfp-type phosphopantetheinyl transferase, and 2,3-dihydroxybenzoate-AMP ligase, respectively;
    (b) *Vibrio cholera* biosynthetic genes comprising a vibH gene, vibF gene or a combination of a vibH gene and vibF gene encoding an amide synthase and peptide synthase, respectively; and
    (c) an schH gene encoding an amide synthase.

2. The method of claim 1, wherein the modified bacterial cell is cultured in iron-deficient media.

3. The method of claim 2, wherein the polyamine linker precursor is a diamine linker precursor.

4. A method comprising culturing a modified *Escherichia coli* (*E. coli*) cell in the presence of a polyamine linker precursor to produce a nonribosomal molecule, wherein the modified *E. coli* cell is transformed with:

an entA gene, an entB gene, an entC gene, an entD gene and an entE gene encoding a 2,3-dihydro-2,3-dihydroxybenzoate dehydrogenase, a 2,3-dihydro-2,3-dihydroxybenzoate synthase, an isochorismate synthase, an Sfp-type phosphopantetheinyl transferase, and 2,3-dihydroxybenzoate-AMP ligase, respectively;

a vibF gene and a vibH gene encoding a peptide synthase and an amide synthase, respectively; and comprises a deletion in an endogenous entF gene.

5. The method of claim 4, wherein the modified *E. coli* cell is cultured in iron-deficient media.

6. The method of claim 4, wherein the polyamine linker precursor is selected from 1,3-Diaminopropane, N-(3-Aminopropyl)-1,4-diaminobutane, N,N'-Bis(3-aminopropyl)-1,4-diaminobutane, 1,5-Diaminopentane, 1,4-Butanediamine dihydrochloride, Bis(3-aminopropyl)amine, m-Xylylenediamine, N,N'-Bis(2-aminoethyl)-1,3-propanediamine, N-Benzylethylenediamine, 4-Aminobenzylamine, 4-(2-Aminoethyl)aniline, 4,4'-Oxydianiline, 4,4'-Diaminodiphenylmethane, 1,5-Diaminonaphthalene, 2,2'-Thiobisacetamide, Sulfaguanidine, p-Aminobenzenesulfonamide, Urea, N-Phenylthiourea, 3,3'-Diamino-N-methyldipropylamine, and 1, 8-Diaminooctane.

7. The method of claim 4, wherein the nonribosomal molecule is selected from the group consisting of: N-(4-(2,3-dihydroxybenzamido)butyl)-2-(2,3-dihydroxyphenyl)-5-methyl-4,5-dihydrooxazole-4-carboxamide; (2R,3S)-3-amino-4-((4-(2,3-dihydroxybenzamido)butyl)amino)-4-oxobutan-2-yl 2,3-dihydroxybenzoate; N-(5-(2,3-dihydroxybenzamido)pentyl)-2-(2,3-dihydroxyphenyl)-5-methyl-4,5-dihydrooxazole-4-carboxamide; (2R,3S)-3-amino-4-((5-(2,3-dihydroxybenzamido)pentyl)amino)-4-oxobutan-2-yl 2,3-dihydroxybenzoate; (4S)—N-(4-((3-(2,3-dihydroxybenzamido)propyl)amino)butyl)-2-(2,3-dihydroxyphenyl)-5-methyl-4,5-dihydrooxazole-4-carboxamide; N-(3-((4-((2S,3R)-2-(2,3-dihydroxybenzamido)-3-hydroxybutanamido)butyl)amino)propyl)-2,3-dihydroxybenzamide; N-(3-(2,3-dihydroxybenzamido)propyl)-2-(2,3-dihydroxyphenyl)-5-methyl-4,5-dihydrooxazole-4-carboxamide; (2R,3S)-3-amino-4-((3-(2,3-dihydroxybenzamido)propyl)amino)-4-oxobutan-2-yl 2,3-dihydroxybenzoate; N-(3-((2,3 dihydroxybenzamido)methyl)benzyl)-2-(2,3-dihydroxyphenyl)-5-methyl-4,5-dihydrooxazole-4-carboxamide; (2R,3S)-3-amino-4-((3-((2,3-dihydroxybenzamido)methyl)benzyl)amino)-4-oxobutan-2-yl 2,3-dihydroxybenzoate; N-(2-((3-((2-(2,3-dihydroxybenzamido)ethyl)amino)propyl)amino)ethyl)-2-(2,3-dihydroxyphenyl)-5-methyl-4,5-dihydrooxazole-4-carboxamide; (14S,15R)-14-amino-1-(2,3-dihydroxyphenyl)-1,13-dioxo-2,5,9,12-tetraazahexadecan-15-yl 2,3-; dihydroxybenzoate; N,N'-Bis(2-aminoethyl)-1,3-propanediamineN-(2-(N-benzyl-2,3-dihydroxybenzamido)ethyl)-2-(2,3-dihydroxyphenyl)-5-methyl-4,5-dihydrooxazole-4-carboxamide; (2R,3S)-3-amino-4-(benzyl(2-(2,3-dihydroxybenzamido)ethyl)amino)-4-oxobutan-2-yl 2,3-dihydroxybenzoate; N-(4-(2,3-dihydroxybenzamido)phenethyl)-2-(2,3-dihydroxyphenyl)-5-methyl-4,5-dihydrooxazole-4-carboxamide; (2R,3S)-3-amino-4-((4-(2-(2,3-dihydroxybenzamido)ethyl)phenyl)amino)-4-oxobutan-2-yl 2,3-dihydroxybenzoate; N-(4-(4-(2,3-dihydroxybenzamido)phenoxy)phenyl)-2-(2,3-dihydroxyphenyl)-5-methyl-4,5-dihydrooxazole-4-carboxamide; (2R,3S)-3-amino-4-((4-(4-(2,3-dihydroxybenzamido)phenoxy)phenyl)amino)-4-oxobutan-2-yl 2,3-dihydroxybenzoate; N-(4-(4-(2,3-dihydroxybenzamido)benzyl)phenyl)-2-(2,3-dihydroxyphenyl)-5-methyl-4,5-dihydrooxazole-4-carboxamide; (2R,3S)-3-amino-4-((4-(4-(2,3-dihydroxybenzamido)benzyl)phenyl)amino)-4-oxobutan-2-yl 2,3-dihydroxybenzoate; (4S)—N-(3-((4-((2-(2,3-dihydroxybenzamido)ethyl)amino)butyl)amino)propyl)-2-(2,3-dihydroxyphenyl)-5-methyl-4,5-dihydrooxazole-4-carboxamide; N-((16S,17R)-1-(2,3-dihydroxyphenyl)-17-hydroxy-1,15-dioxo-2,6,11,14-tetraazaoctadecan-16-yl)-2, 3-dihydroxybenzamide; N-(5-(2,3-dihydroxybenzamido)naphthalen-1-yl)-2-(2,3-dihydroxyphenyl)-5-methyl-4,5-dihydrooxazole-4-carboxamide; (2R,3S)-3-amino-4-((5-(2,3-dihydroxybenzamido)naphthalen-1-yl)amino)-4-oxobutan-2-yl 2,3-dihydroxybenzoate; N-(2-((2-(2,3-dihydroxybenzamido)-2-oxoethyl)thio)acetyl)-2-(2,3-dihydroxyphenyl)-5-methyl-4,5-dihydrooxazole-4-carboxamide;

(2R,3S)-3-amino-4-(2-((2-(2,3-dihydroxybenzamido)-2-oxoethyl)thio)acetamido)-4-oxobutan-2-yl 2,3-dihydroxybenzoate; N—(N-((4-(2,3-dihydroxybenzamido)phenyl)sulfonyl)carbamimidoyl)-2-2,3-dihydroxyphenyl)-5-methyl-4,5-dihydrooxazole-4-carboxamide; (2R,3S)-3-amino-4-((4-(N—((Z)—N'-(2,3-dihydroxybenzoyl)carbamimidoyl)sulfamoyl) phenyl); amino)-4-oxobutan-2-yl 2,3-dihydroxybenzoate; N-((4-(2,3-dihydroxybenzamido)phenyl)sulfonyl)-2-(2,3-dihydroxyphenyl)-5-methyl-4,5-dihydrooxazole-4-carboxamide; (2R,3S)-3-amino-4-((4-(N-(2,3-dihydroxybenzoyl)sulfamoyl)phenyl)amino)-4-oxobutan-2-yl 2,3-dihydroxybenzoate; N-((2,3-dihydroxybenzoyl)carbamoyl)-2-(2,3-dihydroxyphenyl)-5-methyl-4,5-dihydrooxazole-4-carboxamide; (2R,3S)-3-amino-4-(3-(2,3-dihydroxybenzoyl)ureido)-4-oxobutan-2-yl 2,3-dihydroxybenzoate; N-((2,3-dihydroxybenzoyl)(phenyl)carbamothioyl)-2-(2,3-dihydroxyphenyl)-5-methyl-4,5-dihydrooxazole-4-carboxamide; (2R,3S)-3-amino-4-(3-(2,3-dihydroxybenzoyl)-1-phenylthioureido)-4-oxobutan-2-yl 2,3-dihydroxybenzoate; N-(4-(2,3-dihydroxybenzamido)butyl)-2-(2,3-dihydroxyphenyl)-5-methyl-4,5-dihydrooxazole-4-carboxamide; (2R,3S)-3-amino-4-((4-(2,3-dihydroxybenzamido)butyl)amino)-4-oxobutan-2-yl 2,3-dihydroxybenzoate; (2R)-2-(2,3-dihydroxybenzamido)-3-(((2R)-2-(2,3-dihydroxybenzamido)-3-(((2R)-2-(2,3-dihydroxybenzamido)-3-hydroxybutanoyl)oxy)butanoyl)oxy)butanoic acid; (2R)-2-(2,3-dihydroxybenzamido)-3-(((2R)-2-(2,3-dihydroxybenzamido)-3-hydroxybutanoyl)oxy) butanoic acid; (2R)-2-(2,3-dihydroxybenzamido)-3-hydroxybutanoic acid; N-(3-aminopropyl)-2,3-dihydroxybenzamide; N-(3-((4-aminobutyl)amino)propyl)-2,3-dihydroxybenzamide; (S)—N-(3-((4-(2-(2,3-dihydroxybenzamido)-3-hydroxypropanamido)butyl)amino)propyl)-2,3-dihydroxybenzamide;

(S)—N-(2-((4-((3-(2,3-dihydroxybenzamido)propyl)amino)butyl)amino)ethyl)-2-(2,3-dihydroxyphenyl)-4,5-dihydrooxazole-4-carboxamide; (S)—N-(1-(2,3-dihydroxyphenyl)-17-hydroxy-1,15-dioxo-2,6,11,14-tetraazaheptadecan-16-yl)-2,3-dihydroxybenzamide; N-(5-aminopentyl)-2,3-dihydroxybenzamide; N-(4-aminobutyl)-2,3-dihydroxybenzamide (Aminochelin); N-(3-((3-aminopropyl)amino)propyl)-2,3-dihydroxybenzamide; N-(3-(aminomethyl)benzyl)-2,3-dihydroxybenzamide; N-(2-(benzylamino)ethyl)-2,3-dihydroxybenzamide; (S)—N-benzyl-N-(2-(2,3-dihydroxybenzamido)ethyl)-2-(2,3-dihydroxyphenyl)-4,5-dihydrooxazole-4-carboxamide; N-(4-(aminomethyl)phenyl)-2,3-dihydroxybenzamide; N-(4-(2-aminoethyl)phenyl)-2,3-dihydroxybenzamide; N-(4-(4-aminophenoxy)phenyl)-2,3-dihydroxybenzamide; and N-(8-aminooctyl)-2,3-dihydroxybenzamide.

8. A method comprising culturing a modified *Escherichia coli* (*E. coli*) cell in the presence of a polyamine linker precursor and a polyhydroxybenzoate to produce a nonribosomal molecule, wherein the modified *E. coli* cell is transformed with:
an entB gene, an entD gene and an entE gene encoding a 2,3-dihydro-2,3-dihydroxybenzoate synthase, an Sfp-type phosphopantetheinyl transferase, and 2,3-dihydroxybenzoate-AMP ligase, respectively;
a vibF gene and a vibH gene encoding a peptide synthase and an amide synthase, respectively; and
comprises a deletion in an endogenous entA gene, a deletion in an endogenous entC gene and a deletion in an endogenous entF gene.

9. The method of claim 8, wherein the polyhydroxybenzoate is 2,5-Dihydroxybenzoic acid (DHB).

10. The method of claim 8, wherein the modified *E. coli* cell is cultured in iron-deficient media.

11. The method of claim 1, wherein the modified bacterial cell is a modified *Escherichia coli* cell.

12. The method of claim 11, wherein endogenous entD, entC, entE, entB, entA, and entF genes are deleted from the modified bacterial cell.

\* \* \* \* \*